US007514556B2

(12) United States Patent
Besterman et al.

(10) Patent No.: US 7,514,556 B2
(45) Date of Patent: Apr. 7, 2009

(54) INHIBITORS OF β-LACTAMASE

(75) Inventors: Jeffrey M. Besterman, Baie D'Urfe (CA); Jubrail Rahil, Montreal (CA); Arkadii Vaisburg, Kirkland (CA)

(73) Assignee: Methylgene Inc., Montreal (CA)

( * ) Notice: Subject to any disclaimer, the term of this patent is extended or adjusted under 35 U.S.C. 154(b) by 0 days.

(21) Appl. No.: 11/830,305

(22) Filed: Jul. 30, 2007

(65) Prior Publication Data
US 2007/0293675 A1 Dec. 20, 2007

Related U.S. Application Data

(60) Division of application No. 10/884,435, filed on Jul. 2, 2004, now Pat. No. 7,259,172, which is a division of application No. 10/302,124, filed on Nov. 22, 2002, now Pat. No. 6,884,791, which is a continuation-in-part of application No. 10/266,213, filed on Oct. 8, 2002, now Pat. No. 7,030,103, which is a continuation of application No. 09/610,456, filed on Jul. 5, 2000, now Pat. No. 6,472,406.

(60) Provisional application No. 60/142,362, filed on Jul. 6, 1999.

(51) Int. Cl.
C07F 9/142 (2006.01)
(52) U.S. Cl. ................... 546/23; 546/25; 548/119; 558/170
(58) Field of Classification Search ................... None
See application file for complete search history.

(56) References Cited

U.S. PATENT DOCUMENTS

| 2,443,835 | A |   | 6/1948  | Pedersen |
|-----------|---|---|---------|----------|
| 3,870,771 | A |   | 3/1975  | Golburn et al. |
| 3,959,551 | A |   | 5/1976  | Golburn et al. |
| 4,031,170 | A |   | 6/1977  | Birum |
| 4,032,601 | A |   | 6/1977  | Birum |
| 4,302,448 | A | * | 11/1981 | Bickel et al. ............ 514/12 |
| 5,324,855 | A | * | 6/1994  | Morikawa et al. ......... 562/16 |
| 5,420,328 | A | * | 5/1995  | Campbell ............... 558/110 |
| 5,681,821 | A |   | 10/1997 | Powers et al. |
| 6,075,014 | A |   | 6/2000  | Weston et al. |
| 6,472,406 | B1|   | 10/2002 | Besterman et al. |

FOREIGN PATENT DOCUMENTS

| DE | 2 261 081 | 12/1972 |
|----|-----------|---------|
| EP | 261073    | 3/1988  |
| EP | 505122    | 9/1992  |
| EP | 805147    | 11/1997 |
| GB | 1367677   | 9/1974  |
| JP | 54-90160  | 7/1979  |
| JP | 62-126160 | 6/1987  |
| WO | 95/32947  | 12/1995 |
| WO | 97/29080  | 8/1997  |
| WO | 99/33850  | 7/1999  |
| WO | 00/40030  | 1/2000  |
| WO | 01/02411  | 1/2001  |

OTHER PUBLICATIONS

Staib, Arzneimittel-Forschung, Nov. 9, 1959, pp. 696-700.*
Mikolajczyk, M., et al., Tetrahedron: Asymmetry (1997), 8(24), 3991-3994.
Dai, Q and Chen, Ry. Gaodeng Xuexia Huaxue Xuebao (1997), 18(12), 1992-1994.
Chen, Ry and Dai, Q Chin. Chem., Lett. (1955), 6(7), 561-564.
Cremlyn, et al., Phosphorus Sulfur (1979), 5(3), 277-86.
Cremlyn, et al., Phosphorus (1976), 6(3-4), 207-213.
Dryjanski, et al., "Inactivation of the Enterobacter cloacae P99 β-Lactamase by a Fluorescent Phosphonate: Direct Detection of Ligand Binding at the Second Site," Biochemistry, vol. 34, No. 11, 1995, pp. 3569-3575.
Li, et al., "Structure-Activity Studies of the Inhibition of Serine .beta.-Lactamases by Phosphonate Monoesters," Bioorganic & Medicinal Chemistry, vol. 5, No. 9, 1997, pp. 1783-1788.
Rahil, J. and Pratt, RF, "Phosphate Monoester Inhibitors of class A β-lactamases," Biochem. J. (1991) 275, 793-795.
Chen, et al., "Structure of a Phosphonate-inhibited β-Lactamase: An Analog of the Tectrahedral Transition State/Intermediate of β-Lactam Hydrolysis," J. Mol. Biol. (1993) 234, 165-178.
Maveyraud, et al., "Crystal Structure of an Acylation Transition-State Analog of the TEM-1 β-Lactamase, Mechanistic Implications for Class A β-Lactamases," Biochemistry, 1998, 37, 2622-2628.
Rahil, J. and Pratt, RF, "Characterization of Covalently Bound Enzyme Inhibitors as Transition-State Analogs by Protein Stability Measurements: Phosphate Monoester Inhibitors of a β-Lactamase" Biochemistry, vol. 33, No. 1, 1994.
Rahil, J. and Pratt, RF, Kinetics and Mechanism of β-Lactamase Inhibition by Phosphonamidates: The Quest.
Jackson, et al., "Synthesis and Evaluation of Diphenyl Phosphonate Esters as Inhibitors of the Trypsin-like Granzyms A and K and Mast Cell Tryptase," Journal of Medicinal Chemistry, vol. 41, No. 13, pp. 2289-2301, 1998.
Chen, et al., "The Synthesis of Novel Phosphonodipeptides and Their Herbicidal Activity", Heteroatom Chemistry, vol. 4, No. 1, pp. 1-5, 1993.
Chen, "Study on the Mannich-Type Reaction of P-Toluenesulfonamide," Chinese Chemical Letters, vol. 6, No. 3, pp. 181-184, 1995.
Rahil, J. and Pratt, RF, "Kinetics and Mechanism of β-Lactamase Inhibition by Phosphonamidates: The Quest for a Proton", Biochemistry, vol. 32, No. 40, 1993.
Bateson, et al., "The Synthesis and Serine β-Lactamase Inhibitory Activity of Some Phosphonamidate Analogues of Dipeptides," Bioorganic & Medi. Chemistry Letters, vol. 4, No. 14, pp. 1667-1672, 1994.

(Continued)

Primary Examiner—Zinna N Davis
(74) Attorney, Agent, or Firm—McDonnell Boehnen Hulbert & Berghoff LLP

(57) ABSTRACT

The intention relates to bacterial antibiotic resistance and, in particular, to compositions and methods for overcoming bacterial antibiotic resistance. The invention provides novel β-lactamase inhibitors, which are structurally unrelated to the natural product and semi-synthetic β-lactamase inhibitors presently available, and which do not require a β-lactam pharmacophore. The invention also provides pharmaceutical compositions and methods for inhibiting bacterial growth.

6 Claims, 1 Drawing Sheet

OTHER PUBLICATIONS

Pratt, RF, "Inhibition of a Class C β-Lactamase by a Specific Phosphonate Monoester," Nov. 17, 1989, vol. 246, pp. 917-919.

Rahil, J. and Pratt, RF, "Mechanism of Inhibition of the Class C β-Lactamase of *Enterobacter cloacae* P99 by Phosphonate Monoesters," Biochemistry, vol. 31, No. 25, 1992.

Rahil, J., and Pratt, RF, Characterization of Covalently Bound Enzyme Inhibitors as Transition-State Analogs by Protein Stability Measurements: Phosphate Monoester Inhibitors of a β-Lactamase, no date given.

Rahil, J. and Pratt, RF, "Structure-Activity Relationships in the Inhibition of Serine β-Lactamases by Phosphonic Acid Derivatives," Biochem pp. 389-393, no date given.

Silvaggi, et al., "The Crystal Structure of Phosphonate-Inhibited D-Ala-D-Ala Peptidase Reveals an Analogue of a Tetrahedral Transition State," Biochem (2003).

Lobkovsky, et al., "Crystallographic Structure of a Phosphonate Derivative of the *Enterobacter cloacae* P99 Cephalosporinase: Mechanistic Interpretation of a β-Lactamase Transition-State Analog," Biochemistry 1994, 33, 3462-6772.

Dryjanski, Marek and Pratt, RF, "Steady-State Kinetics of the Binding of β-Lactams and Penicilloates to the Second Binding Site of the *Enterobacter cloacae* P99 β-Lactamase," Biochemistry 1995, 34, 3561-3568.

Rahil, J. and Pratt, RF, Intramolecular Participation of the Amide Group in Acid-and Base-Catalysed Phosphonate Monoester Hydrolysis, no date given.

Xie, Gui-Yang et al., "Synthesis of a Novel Antigen Containing Phosphorus", Chemical Journal of Chinese Universities, Gaodeng Xuexiao Huaxue Xuebao, vol. 24, No. 6, 2003, pp. 1037-1039.

Maveyraud, Laurent et al., "Crystal Structure of an Acylation Transition-State Analog of the TEM-1 β-Lactamase. Mechanistic Implications for Class A β-Lactamases", Biochemistry, vol. 37, 1998, pp. 2622-2628.

Li, Naixin et al., "Structure-Activity Studies of the Inhibition of Serine β-Lactamases by Phosphonate Monoesters", Bioorganic & Medicinal Chemistry, vol. 5, No. 9, pp. 1783-1788, 1997.

Chen, Celia C. H., et al., "Structure of a Phosphonate-Inhibited β-Lactamase. An Analog of the Tetrahedral Transition State/Intermediate of β-Lactam Hydrolysis", Journal of Molecular Biology, vol. 234, pp. 165-178, no date.

Rahil, Jubrail et al., "Characterization of Covalently Bound Enzyme Inhibitors as Transition-State Analogs by Protein Stability Measurements: Phosphonate Monoester Inhibitors of a βLactamase", Biochemistry, vol. 33, 1994, pp. 116-125.

Rahil, Jubrail et al., "Structure-Activity Relationships in the Inhibition of Serine βLactamases by Phosphonic Acid Derivatives", Biochemical Journal, vol. 296, pp. 389-393, no date given.

Rahil, Jubrail et al., "Mechanism of Inhibition of the Class C β-Lactamase of *Enterobacter cloacae* P99 by Phosphonate Monoesters", Biochemistry, vol. 31, pp. 5869-5878, no date given.

Rahil, J. et al., "Intramolecular Participation of the Amide Group in Acid- and Base-Catalysed Phosphonate Monoester Hydrolysis", Journal of the Chemical Society, Perkin Transactions 2: Physical Organic Chemistry, 1991, pp. 947-950.

International Search Report for PCT Application Serial No. PCT/US03/36929, Dated May 14, 2004.

Ovrutskii et al., Khimiko-Famatsevticheskii Zhurnal (1990), 24(4), 12-14.

Pine SH., Organic Chemistry, Fifth Edition, Inside page of cover, no date available.

Cohen, Science, 257:1051-1055 (1992).

Neu, Science, 257:1064-1073 (1992).

Coulton et al., Progress in Medicinal Chemistry, 31:297-349 (1994).

Dudley, Pharmacotherapy, 15:9S-14S (1995).

Sutherland, Trends Pharmacol. Sci., 12:227-232 (1991).

Ghysen, Prospect Biotechnol., 128:67-95 (1987).

Black et al., Current Pharmaceutical Design, 4:133-154 (1998).

Dalbey et al., Protein Science, 6:1129-1138 (1997).

Waley, The Chemistry of B-Lactamase, Page Ed., Chapman & Hall, London, 198-228 (1992).

March, Advanced Organic Chemistry, Third Edition, John Wiley & Sons, 310-316 (1985).

Nikaido and Vaara, Microbiological Review, 49:1-32 (1985).

Livermore, Scad. J. Infect. Dis., Suppl., 74:15-22 (1991).

Goodman and Gilmans, The Pharmacological Basis of Therapeutics, 8th Ed., "Biotransformation of Drugs", McGraw Hill, Int. Ed., 13-15 (1992).

Payne et al., Antimicrobial Agents and Chemotherapy, 38:767-775 (1994).

Hanaki et al., Antimicrobiol Agents and Chemotherapy, 30:1120-1126 (1995).

S.L. Graham et al., J. Med. Chem., 32:2548 (1989).

* cited by examiner

INHIBITORS OF β-LACTAMASE

CROSS-REFERENCE TO RELATED APPLICATIONS

This application is a division of U.S. application Ser. No. 10/884,435 filed Jul. 2, 2004, which is a division of U.S. application Ser. No. 10/302,124 filed Nov. 22, 2002, now U.S. Pat. No. 6,884,791, which is a continuation-in-part of a U.S. application Ser. No. 10/266,213 filed Oct. 8, 2002, now U.S. Pat. No. 7,030,103, which is a continuation of U.S. application Ser. No. 09/610,456 filed Jul. 5, 2000, now U.S. Pat. No. 6,472,406, which claims the benefit of U.S. Provisional Application No. 60/142,362 filed on Jul. 6, 1999.

BACKGROUND OF THE INVENTION

1. Field of the Invention

The invention relates to bacterial antibiotic resistance. More particularly, the invention relates to compositions and methods for overcoming bacterial antibiotic resistance 2. Brief Summary of the Related Art Bacterial antibiotic resistance has become one of the most important threats to modern health care. Cohen, Science 257: 1051-1055 (1992) discloses that infections caused by resistant bacteria frequently result in longer hospital stays, higher mortality and increased cost of treatment. Neu, Science 257: 1064-1073 (1992) discloses that the need for new antibiotics will continue to escalate because bacteria have a remarkable ability to develop resistance to new agents rendering them quickly ineffective.

The present crisis has prompted various efforts to elucidate the mechanisms responsible for bacterial resistance. Coulton et al., Progress in Medicinal Chemistry 31:297-349 (1994) teaches that the widespread use of penicillins and cephalosporins has resulted in the emergence of β-lactamases, a family of bacterial enzymes that catalyze the hydrolysis of the β-lactam ring common to numerous presently used antibiotics. More recently, Dudley, Pharmacotherapy 15: 9S-14S (1995) has disclosed that resistance mediated by β-lactamases is a critical aspect at the core of the development of bacterial antibiotic resistance.

Attempts to address this problem through the development of β-lactamase inhibitors have had limited success. Sutherland, Trends Pharmacol. Sci. 12: 227-232 (1991) discusses the development of the first clinically useful β-lactamase inhibitor, clavulanic acid, which is a metabolite of *Streptomyces clavuligerus*. Coulton et al (supra) discloses two semi-synthetic inhibitors, sulbactam and tazobactam, presently available. Coulton et al. (supra) also teaches that in combination with β-lactamase-susceptible antibiotics, β-lactamase inhibitors prevent antibiotic inactivation by β-lactamase enzymes, thereby producing a synergistic effect against β-lactamase producing bacteria Li et al., Bioorg. Med. Chem. 5 (9): 1783-1788 (1997), discloses that β-lactamase enzymes are inhibited by phosphonate monoesters. Li et al. teaches that better inhibitory activity is achieved by compounds with amido side-chains, but that such compounds suffer the disadvantage of hydrolytic instability. Li et al. discloses that benzylsulfonamidomethyl phosphonate monoesters exhibit better hydrolytic stability, but also significantly weaker potency against β-lactamase enzymes, than do the corresponding benzylamidomethyl phosphonate monoesters. Dryjanski and Pratt, Biochemistry 34:3569-3575 (1995) teaches that p-nitrophenyl[(dansylamido)methyl]phosphonate irreversibly inactivates the P99 β-lactamase enzyme, and describes its use as a mechanistic probe for studying the interaction of ligands with a second binding site of the enzyme.

The availability of only a few β-lactamase inhibitors, however, is insufficient to counter the constantly increasing diversity of β-lactamases, for which a variety of novel and distinct inhibitors has become a necessity. There is, therefore, a need for the ability to identify new β-lactamase inhibitors. The development of fully synthetic inhibitors would greatly facilitate meeting this need.

BRIEF SUMMARY OF THE INVENTION

The invention provides novel β-lactamase inhibitors, which are structurally unrelated to the natural product and semi-synthetic β-lactamase inhibitors presently available, and which do not require a β-lactam pharmacophore.

In a second aspect, the invention provides pharmaceutical compositions comprising a compound of the invention and a pharmaceutically acceptable carrier or diluent.

In a third aspect, the invention provides methods for inhibiting bacterial growth, such methods comprising administering to a bacterial cell culture, or to a bacterially infected cell culture, tissue, or organism, a β-lactamase inhibitor of the invention.

DETAILED DESCRIPTION OF THE PREFERRED EMBODIMENTS

Figure 1:
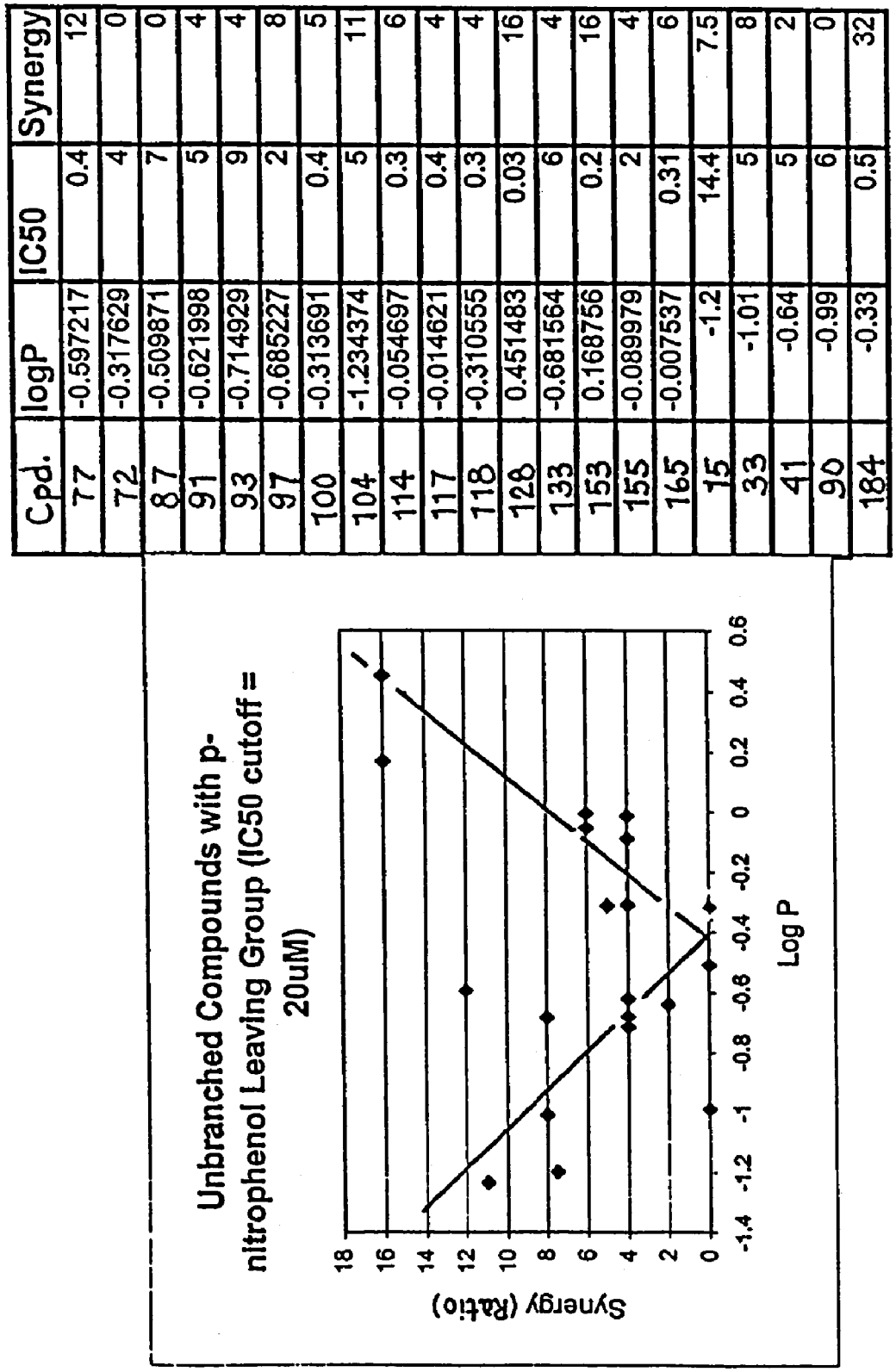
FIG. 1 is a graphical plot of the synergistic effect of β-lactamase inhibitors as a function of log P. Synergy is defined and methods for its determination are provided in the Examples.

The invention relates to bacterial antibiotic resistance. More particularly, the invention relates to compositions and methods for overcoming bacterial antibiotic resistance. The patents and publications identified in this specification indicate the knowledge in this field and are hereby incorporated by reference in their entirety. In the case of inconsistencies, the present disclosure will prevail.

The invention provides novel β-lactamase inhibitors, which are structurally unrelated to the natural product and semi-synthetic β-lactamase inhibitors presently available, and which do not require a β-lactam pharmacophore. Certain embodiments of these new inhibitors may also bind bacterial DD-peptidases, and thus may potentially act both as β-lactamase inhibitors and as antibiotic agents.

Li et al., Bioorg. Med. Chem. 5 (9):1783-1788 (1997), and Dryjanski and Pratt, Biochemistry 34:3569-3575 (1995), teach that β-lactamase enzymes are inactivated by 4-nitrophenyl N-(phenylmethylsulfonyl)aminomethylphosphonate and p-nitro-phenyl[(dansylamido)methyl]-posphonate, respectively. Despite the enzyme inhibitory activity of these compounds, however, neither compound is effective in producing a synergistic effect when co-administered with an antibiotic agent to a bacterially infected cell culture (see Table 1, compounds 1 and 72). By contrast, the present inventors have surprisingly discovered that aryl- and (heteroaryl)-sulfonamidomethylphosphonate monoesters both inhibit enzymatic activity in vitro and enhance the potency of antibiotic agents in cell culture.

For purposes of the present invention, the following definitions will be used:

As used herein, the term "β-lactamase inhibitor" is used to identify a compound having a structure as defined herein, which is capable of inhibiting β-lactamase activity. Inhibiting β-lactamase activity means inhibiting the activity of a class A, B, C, or D β-lactamase. Preferably, for antimicrobial applications such inhibition should be at a 50% inhibitory concentration below 100 micrograms/mL, more preferably below 30 micrograms/mL and most preferably below 10 micrograms/mL. The terms "class A", "class B", "class C", and "class D" β-lactamases are understood by those skilled in the art and can be found described in Waley, *The Chemistry of β-Lactamase*, Page Ed., Chapman & Hall, London, (1992) 198-228

In some embodiments of the invention, the β-lactamase inhibitor may also be capable of acting as an antibiotic agent by inhibiting bacterial cell-wall cross-linking enzymes. Thus, the term β-lactamase inhibitor is intended to encompass such dual-acting inhibitors. In certain preferred embodiments, the β-lactamase inhibitor may be capable of inhibiting D-alanyl-D-alanine-carboxypeptidases/transpeptidases (hereinafter DD-peptidases). The term "DD-peptidase" is used in its usual sense to denote penicillin-binding proteins involved in bacterial cell wall biosynthesis (see, e.g., Ghysen, Prospect. Biotechnol. 128:67-95 (1987)). In certain particularly preferred embodiments, the D-alanyl-D-alanine-carboxypeptidase/transpeptidase, which may be inhibited is the *Streptomyces* R61 DD-peptidase. This enzyme has conservation of active site mechanism with bacterial signal peptidases (see, e.g., Black et al., Current Pharmaceutical Design 4:133-154 (1998); Dalbey et al., Protein Science 6:1129-1138 (1997)). It is, therefore, possible that the β-lactamase inhibitors of the invention may also be capable of inhibition of bacterial signal peptidases As used herein, the term "β-lactamase" denotes a protein capable of inactivating a β-lactam antibiotic. In one preferred embodiment, the β-lactamase is an enzyme which catalyzes the hydrolysis of the β-lactam ring of a β-lactam antibiotic. In certain preferred embodiments, the β-lactamase is microbial. In certain other preferred embodiments, the β-lactamase is a serine β-lactamase. Examples of such preferred β-lactamases are well known and are disclosed in, e.g., Waley, *The Chemistry of β-Lactamase, Page Ed., Chapman & Hall, London, (1992) 198-228*. In particularly preferred embodiments, the β-lactamases is a class C β-lactamase of *Enterobacter cloacae* P99 (hereinafter P99 lactamase), or a class A β-lactamase of the TEM-2 plasmid (hereinafter TEM β-lactamase).

As used herein, the term "organism" refers to any multicellular organism. Preferably, the organism is an animal, more preferably a mammal, and most preferably a human For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B-, wherein a is 0 or 1. In such instances, when a is 0 the moiety is B- and when a is 1 the moiety is A-B-. Also, a number of moieties disclosed herein exist in multiple tautomeric forms, all of which are intended to be encompassed by any given tautomeric structure.

The term "alkyl" as employed herein refers to straight and branched chain aliphatic groups having from 1 to 12 carbon atoms, preferably 1-8 carbon atoms, more preferably 1-6 carbon atoms, which is optionally substituted with one, two or three substituents. Unless otherwise specified, the alkyl group may be saturated, unsaturated, or partially unsaturated. As used herein, therefore, the term "alkyl" is specifically intended to include alkenyl and alkynyl groups, as well as saturated alkyl groups. Preferred alkyl groups include, without limitation, methyl, ethyl, propyl, isopropyl, butyl, tert-butyl, isobutyl, pentyl, hexyl, vinyl, allyl, isobutenyl; ethynyl, and propynyl.

As employed herein, a "substituted" alkyl, cycloalkyl, aryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "cycloalkyl" as employed herein includes saturated and partially unsaturated cyclic hydrocarbon groups having 3 to 12, preferably 3 to 8 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $C_{1-6}$alk($C_{6-10}$)aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methylnaphthyl.

A "heterocyclic" group is a ring structure having from about 3 to about 8 atoms, wherein one or more atoms are selected from the group consisting of N, O, and S. The heterocyclic group is optionally substituted on carbon with oxo or with one of the substituents listed above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino.

In certain preferred embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 n electrons shared in a cyclic array; and having, in addition to carbon atoms, between one and about three heteroatoms selected from the group consisting of N, O, and S. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other preferred embodiments, the heterocyclic group is fused to an aryl or heteroaryl group. Examples of such fused heterocycles include, without limitation, tetrahydroquinolinyl and dihydrobenzofuranyl.

Additional preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, 1H-indazolyl, indolenyl, indolinyl, indolizinyl, 3H-indolyl, isobenzofuranyl, isochromanyl, isoindazolyl, isoindolinyl, isoindolyl, isothiazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazolidinyl, pyrazolinyl, pyridazinyl, pyridooxazole, pyridoimidazole, pyridothiazole, pyridinyl, pyrrolidinyl, pyrrolinyl, 2H-pyrrolyl, quinazolinyl, 4H-quinolizinyl, quinuclidinyl, tetrahydroisoquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A moiety that is substituted is one in which one or more hydrogens have been independently replaced with another chemical substituent. As a nonlimiting example, substituted phenyls include 2-fluorophenyl, 3,4-dichlorophenyl, 3-chloro-4-fluoro-phenyl, 2-fluor-3-propylphenyl. As another non-limiting example, substituted n-octyls include 2,4 dimethyl-5-ethyl-octyl and 3-cyclopentyl-octyl. Included within this definition are methylenes (—$CH_2$—) substituted with oxygen to form carbonyl-CO—).

Unless otherwise stated, as employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular-CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_2$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above; and (c) —$(CH_2)_S$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

The term "halogen" or "halo" as employed herein refers to chlorine, bromine, fluorine, or iodine As herein employed, the term "acyl" refers to an alkylcarbonyl or arylcarbonyl substituent.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. The term "amino" is meant to include $NH_2$, alkylamino, arylamino, and cyclic amino groups.

The term "ureido" as employed herein refers to a substituted or unsubstituted urea moiety.

The structure:

represents —S—, —S(O)— or —S(O)$_2$— when Z is S and n is 0, 1, or 2, respectively, —$CH_2$— when Z is $CH_2$ and n is 0, and —C(O)— when Z is C and n is 1.

Preferred embodiments of a particular genus of compounds of the invention include combinations of preferred embodiments. For example, preferred $R^2$ substituents are given in paragraph [0046] and preferred $R^3$ substituents are given in paragraph [0047]. Thus, preferred compounds according to the invention include those in which $R^2$ is as described in paragraph [0046] and $R^3$ is as described in paragraph [0047].

Compounds

[0037] In a first aspect, the invention provides novel β-lactamase inhibitors. In one embodiment of the invention, the novel β-lactamase inhibitor is a compound of Formula (I):

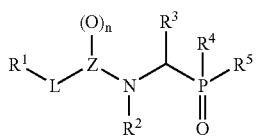

or a pro-drug or pharmaceutically acceptable salt thereof, wherein
$R^1$ is aryl or heteroaryl, wherein the aryl or heteroaryl group is optionally substituted;
Z is C, $CH_2$, or S;
n is 0, 1, or 2 when Z is S, n is when Z is C, and n is 0 when Z is $CH_2$;
L is $C_0$-$C_3$-alkyl, $C_1$-$C_3$-alkyl-O—, —C(O)—, or —C(=N—$OCH_3$)—;
$R^2$ is selected from the group consisting of hydrogen, alkyl, cycloalkyl, aralkyl, and aryl, any of which is optionally substituted;
$R^3$ is selected from the group consisting of hydrogen, alkyl, cycloalkyl, aralkyl, aryl, heteroaryl, and (heteroaryl)alkyl, any of which groups is optionally substituted;
$R^4$ is selected from the group consisting of OH, F, $SR^7$, and $N(R^7)_2$; and
$R^5$ is selected from the group consisting of F, $OR^6$, $SR^7$, and $N(R^7)_2$,
  $R^6$ is selected from the group consisting of —H, alkyl, cycloalkyl, $C_0$-$C_3$-alkyl-cycloalkyl, aryl, $C_0$-$C_3$-alkaryl, aralkyl, (heteroaryl)alkyl, heteroaryl, and $C_0$-$C_3$-alkyl-heteroaryl, wherein the aryl or heteroaryl portion of any such group is optionally substituted, and
  $R^7$ at each occurrence is independently selected from the group consisting of hydrogen, alkyl, cycloalkyl, aralkyl, and aryl, each of which is optionally substituted;

provided that $R^4$ and $R^5$ are not both F, and further provided that $R^1$ is not 5-dimethylamino-1-naphthyl when $R^2$ and $R^3$ are both H, $R^4$ is OH, and $R^5$ is 4-nitrophenoxy.

In one preferred embodiment of the compound according to paragraph [0037], Z is S.

[0039] In another embodiment, the novel β-lactamase inhibitor is a compound of Formula (I):

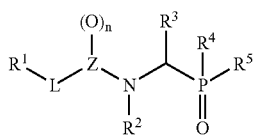

or a pro-drug or pharmaceutically acceptable salt thereof, wherein
$R^1$ is aryl or heteroaryl, wherein the aryl or heteroaryl group is optionally substituted;
Z is C, $CH_2$, or S;
n is 0, 1, or 2 when Z is S, n is 1 when Z is C, and n is 0 when Z is $CH_2$;
L is $C_0$-$C_3$-alkyl, $C_1$-$C_3$-alkyl-O—, —C(O)—, or —C(=N—$OCH_3$)—;
$R^2$ is selected from the group consisting of hydrogen, alkyl, cycloalkyl, aralkyl, and aryl, wherein the aryl portion of any such group is optionally substituted;
$R^3$ is selected from the group consisting of hydrogen, alkyl, cycloalkyl, aralkyl, aryl, heteroaryl, and (heteroaryl)alkyl, wherein the aryl or heteroaryl portion of any such group is optionally substituted;
$R^4$ is $OR^8$, where $R^8$ is selected from the group consisting of phenyl substituted with at least one chloro, nitro, or fluoro substituent; heteroaryl; and substituted heteroaryl; and
$R^5$ is $OR^6$, where $R^6$ is selected from the group consisting of H, alkyl, cycloalkyl, aryl, aralkyl, (heteroaryl)alkyl, and heteroaryl, wherein the aryl or heteroaryl portion of any such group is optionally substituted.

In one preferred embodiment of the compound according to paragraph [0039], Z is S.

In yet another embodiment, the novel β-lactamase inhibitor is a compound of Formula (II):

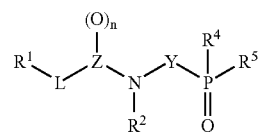

or a pro-drug or pharmaceutically acceptable salt thereof, wherein
$R^1$ is aryl or heteroaryl, wherein the aryl or heteroaryl group is optionally substituted;
Z is C, $CH_2$, or S;
n is 0, 1, or 2 when Z is S, n is 1 when Z is C, and n is 0 when Z is $CH_2$;
L is $C_0$-$C_3$-alkyl, $C_1$-$C_3$-alkyl-O—, —C(O)—, or —C(=$NOCH_3$)—;
Y is O, $NR^7$, or S;
$R^2$ is selected from the group consisting of hydrogen, alkyl, cycloalkyl, aralkyl, and aryl;
$R^4$ and $R^5$ are independently selected from the group consisting of OH, F, $SR^7$, $N(R^7)_2$, and $OR^6$,
  where $R^6$ is selected from the group consisting of alkyl, cycloalkyl, aryl, aralkyl, (heteroaryl)alkyl, and heteroaryl, wherein the aryl or heteroaryl portion of any such group is optionally substituted, and where $R^7$ at each occurrence is independently selected from the group consisting of hydrogen, alkyl, cycloalkyl, aralkyl, and aryl;
  provided that $R^4$ and $R^5$ are not both F or both OH.

With respect to the compounds of Formula (I) or Formula (II), the following preferred values are applicable:

In certain preferred embodiments, $R^1$ is $C_{6-14}$aryl, more preferably $C_{6-10}$aryl, most preferably phenyl or naphthyl, any of which may be substituted. In certain other preferred embodiments, $R^1$ is heteroaryl or substituted heteroaryl. Preferably, the heteroaryl group is selected from the group consisting of thienyl, benzothienyl, furyl, benzofuryl, quinolyl, isoquinolyl, and thiazolyl. In certain particularly preferred embodiments, the heteroaryl group is thienyl or benzothienyl Substituted aryl or heteroaryl groups have one or more, preferably between one and about three, more preferably one or two substituents, which are preferably selected from the group consisting of $C_{1-6}$alkyl, preferably $C_{1-4}$alkyl; halo, preferably Cl, Br, or F; haloalkyl, preferably $(halo)_{1-5}(C_{1-6})$alkyl, more preferably $(halo)_{1-5}(C_{1-3})$alkyl, and most preferably $CF_3$; $C_{1-6}$alkoxy, preferably methoxy, ethoxy, or benzyloxy; $C_{6-10}$aryloxy, preferably phenoxy; $C_{1-6}$-alkoxycarbonyl, preferably $C_{1-3}$alkoxycarbonyl, most preferably carbomethoxy or carboethoxy; $C_{6-10}$aryl, preferably phenyl; $(C_{6-10})$ar$(C_{1-6})$alkyl, preferably $(C_{6-10})$ar$(C_{1-3})$alkyl, more preferably benzyl, naphthylmethyl or phenethyl; hydroxy$(C_{1-6})$alkyl, preferably hydroxy$(C_{1-3})$alkyl, more preferably hydroxymethyl; amino$(C_{1-6})$alkyl, preferably amino$(C_{1-3})$alkyl, more preferably aminomethyl; $(C_{1-6})$alkylamino, preferably methylamino, ethylamino, or propylamino; di-$(C_{1-6})$alkylamino, preferably dimethylamino or diethylamino; $(C_{1-6})$alkylcarbamoyl, preferably methylcarbamoyl, dimethylcarbamoyl, or benzylcarbamoyl; $(C_{6-10})$arylcarbamoyl, preferably phenylcarbamoyl; $(C_{1-6})$alkaneacylamino, preferably acetylamino; $(C_{6-10})$areneacylamino, preferably benzoylamino; $(C_{1-6})$alkanesulfonyl, preferably methanesulfonyl; $(C_{1-6})$alkanesulfonamido, preferably methanesulfonamido; $(C_{6-10})$arenesulfonyl, preferably benzenesulfonyl or toluenesulfonyl; $(C_{6-10})$arenesulfonamido, preferably benzenesulfonyl or toluenesulfonyl; $(C_{6-10})$ar$(C_{1-6})$alkylsulfonamido, preferably benzylsulfonamido; $C_{1-6}$alkylcarbonyl, preferably $C_{1-6}$alkylcarbonyl, more preferably acetyl; $(C_{1-6})$acyloxy, preferably acetoxy; cyano; amino; carboxy; hydroxy; ureido; and nitro.

Preferably, n is 1 or 2. More preferably n is 2.

[0046] $R^2$ is preferably selected from the group consisting of H; $C_{1-8}$alkyl, preferably $C_{1-6}$alkyl, more preferably $C_{1-4}$alkyl; $C_{3-8}$cycloalkyl, preferably cyclopropyl, cyclopentyl, or cyclohexyl; $(C_{6-10})$ar$(C_{1-6})$alkyl, preferably $(C_{6-10})$ar$(C_{1-3})$alkyl, more preferably benzyl; and $C_{6-10}$aryl, preferably phenyl; any of which groups is optionally substituted. More preferably, $R^2$ is one of H, methyl, ethyl, propyl, cyclopropyl or benzyl. Most preferably, $R^2$ is H.

[0047] $R^3$ is preferably selected from the group consisting of H; $C_{1-8}$alkyl, preferably $C_{1-6}$alkyl, more preferably $C_{1-4}$alkyl; $C_{3-8}$cycloalkyl, preferably cyclopropyl, cyclopentyl, or cyclohexyl; $(C_{6-10})$ar$(C_{1-6})$alkyl, preferably $(C_{6-10})$ar$(C_{1-3})$alkyl, more preferably benzyl; heterocyclic having one or more, preferably between one and about three, more preferably one or two, ring atoms independently selected from the group consisting of N, O, and S; heterocyclic$(C_{1-6})$alkyl, preferably heterocyclic$(C_{1-3})$alkyl; and $C_{6-10}$aryl, preferably phenyl; any of which groups may be optionally substituted. More preferably, $R^3$ is one of H, methyl, ethyl, propyl, isopropyl, isobutyl, butyl, phenyl, or benzyl.

In certain other preferred embodiments, $R^2$ and $R^3$ are taken together with the carbon and nitrogen atoms to which they are attached to form a nitrogen-containing heterocyclic ring. Preferably, the heterocyclic ring is a to 7-membered ring, more preferably a 5- or 6-membered ring.

In certain preferred embodiments, $R^4$ is preferably OH. In certain other preferred embodiments, $R^4$ is preferably $OR^8$, wherein $R^8$ is preferably selected from the group consisting of phenyl or heteroaryl, either of which may be optionally substituted. Where $R^8$ is phenyl, the phenyl group is preferably substituted with at least one ester, amide, chloro, nitro, or fluoro substituent; more preferably with at least one chloro, nitro, or fluoro substituent; and most preferably with at least one nitro substituent.

$R^5$ is preferably selected from the group consisting of F, $OR^6 SR^7$ and $N(R^7)_2$, where $R^6$ and $R^7$ are as defined below. More preferably, $R^5$ is F or $OR^6$. In certain particularly preferred embodiments, $R^5$ is a good leaving group. Leaving group ability is understood by those skilled in the art, and is generally described in March, Advanced Organic Chemistry, Third Edition, John Wiley & Sons, 1985, pp 310-316. Compounds according to this embodiment of the invention are subject to attack by a nucleophilic residue such as serine on the enzyme, resulting in irreversible inactivation of the enzyme.

$R^6$ is preferably selected from the group consisting of $C_{1-8}$alkyl, preferably $C_{1-6}$-alkyl, more preferably $C_{1-4}$alkyl; $C_{3-8}$cycloalkyl, preferably cyclopropyl, cyclopentyl, or cyclohexyl; $(C_{6-10})$ar$(C_{1-6})$alkyl, preferably $(C_{6-10})$ar$(C_{1-3})$alkyl, more preferably benzyl; heterocyclic having one or more, preferably between one and about three, more preferably one or two, ring atoms independently selected from the group consisting of N, O, and S; heterocyclic$(C_{1-6})$alkyl, preferably heterocyclic$(C_{1-3})$alkyl; and $C_{6-10}$aryl, preferably phenyl; any of which groups may be optionally substituted. Preferably, the heterocyclic group is heteroaryl.

More preferably, $R^6$ is $C_{6-10}$aryl or heteroaryl, either of which is optionally substituted with between one and about three, more preferably one or two substituents, which are preferably selected from the group consisting of $C_{1-6}$alkyl, preferably $C_{1-4}$alkyl; halo, preferably Cl, Br, or F; haloalkyl, preferably (halo)$_{1-5}$$(C_{1-6})$alkyl, more preferably (halo)$_{1-5}$$(C_{-3})$alkyl, and most preferably $CF_3$; $C_{1-6}$alkoxy, preferably methoxy, ethoxy, or benzyloxy; $C_{6-10}$aryloxy, preferably phenoxy; $C_{1-6}$alkoxycarbonyl, preferably $C_{1-3}$alkoxycarbonyl, most preferably carbomethoxy or carboethoxy; $C_{6-10}$aryl, preferably phenyl; $(C_{6-10})$ar$(C_{1-6})$alkyl, preferably $(C_{6-10})$ar$(C_{1-3})$alkyl, more preferably benzyl, naphthylmethyl or phenethyl; hydroxy$(C_{1-6})$alkyl, preferably hydroxy$(C_{1-3})$alkyl, more preferably hydroxymethyl; amino$(C_{1-6})$alkyl, preferably amino$(C_{1-3})$alkyl, more preferably aminomethyl; $(C_{1-6})$alkanesulfonyl, preferably methanesulfonyl; $(C_{1-6})$alkanesulfonamido, preferably methanesulfonamido; $(C_{6-10})$arenesulfonyl, preferably benzenesulfonyl or toluenesulfonyl; $(C_{6-10})$arenesulfonamido, preferably benzenesulfonyl or toluenesulfonyl; $(C_{6-10})$ar$(C_{1-6})$alkylsulfonamido, preferably benzylsulfonamido; $C_{1-6}$alkylcarbamoyl, preferably methylcarbamoyl, dimethylcarbamoyl, or benzylcarbamoyl; $C_{6-10}$arylcarbamoyl, preferably benzylcarbamoyl; $(C_{1-6})$alkane-acylamino, preferably acetylamino; $(C_{6-10})$areneacylamino, preferably benzoylamino; $C_{1-6}$alkylcarbonyl, preferably $C_{1-3}$alkylcarbonyl, more preferably acetyl; cyano; amino; carboxy; hydroxy; and nitro.

Most preferably, $R^6$ is an aryl or heteroaryl group substituted with one or more substituents selected from the group consisting of halo, preferably chloro or fluoro; haloalkyl, preferably trifluoromethyl; nitro; cyano; acyl; carboxy; and alkoxycarbonyl. More preferably, the aryl or heteroaryl group has one or more chloro, fluoro, or nitro substituents. Most preferably, $R^6$ is selected from the group consisting of nitrophenyl, pentafluorophenyl, trifluorophenyl, pyridyl, chloropyridyl, isoquinolyl, and quinolyl.

$R^7$ is preferably selected from the group consisting of H; $C_{1-8}$alkyl, preferably $C_{1-6}$alkyl, more preferably $C_{1-4}$alkyl; $C_{3-8}$cycloalkyl, preferably cyclopropyl, cyclopentyl, or cyclohexyl; $(C_{6-10})$ar$(C_{1-6})$alkyl, preferably $(C_{6-10})$ar$(C_{1-3})$alkyl, more preferably benzyl; and $C_{6-10}$aryl, preferably phenyl; any of which groups may be optionally substituted.

With respect to the compounds of Formula (II), Y is O, $NR^7$, or S. Preferably, Y is $NR^7$, where $R^7$ is as defined above. In certain particularly preferred embodiments, Y is NH.

[0056] In another preferred embodiment of the compound according to paragraph [0037], one or more of the following is true:
  $R^1$ is aryl (preferably phenyl) or thienyl, each of which is optionally substituted;
  L is methyl, methoxy, —C(O)—, or —C(=N—OCH$_3$)—;
  Z is C and n is 1;

$R^2$ is H;

$R^3$ is H;

$R^4$ is —OH;

$R^5$ is F, —$OR^6$, or —$SR^6$; and/or $R^6$ is aryl or heteroaryl, each of which is optionally substituted.

[0057] In a preferred embodiment of the compound according to paragraph [0056], Z is C and n is 1; $R^2$ is H; $R^3$ is H; and $R^4$ is —OH:

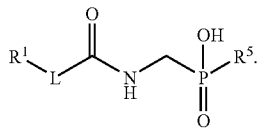

[0058] In a preferred embodiment of the compound according to paragraph [0057], $R^1$ is phenyl or thien-2-yl, each optionally substituted;

L is a covalent bond, —$CH_2O$—, —C(O)—, or —C(=N—$OCH_3$)—; and $R^5$ is -halo or —$OR^{10}$ wherein $R^{10}$ is phenyl, pyridinyl, or quinolinyl, each optionally substituted, provided that when L is —$CH_2O$—, $R^5$ is not —F or p-nitrophenoxy.

Preferred substituents on the compound according to paragraph [0058] are —$NO_2$, —$CO_2H$, and halo. Preferably $R^1$ is unsubstituted in the compound according to paragraph [0058].

In a preferred embodiment of the compound according to paragraph [0058], $R^5$ is selected from:

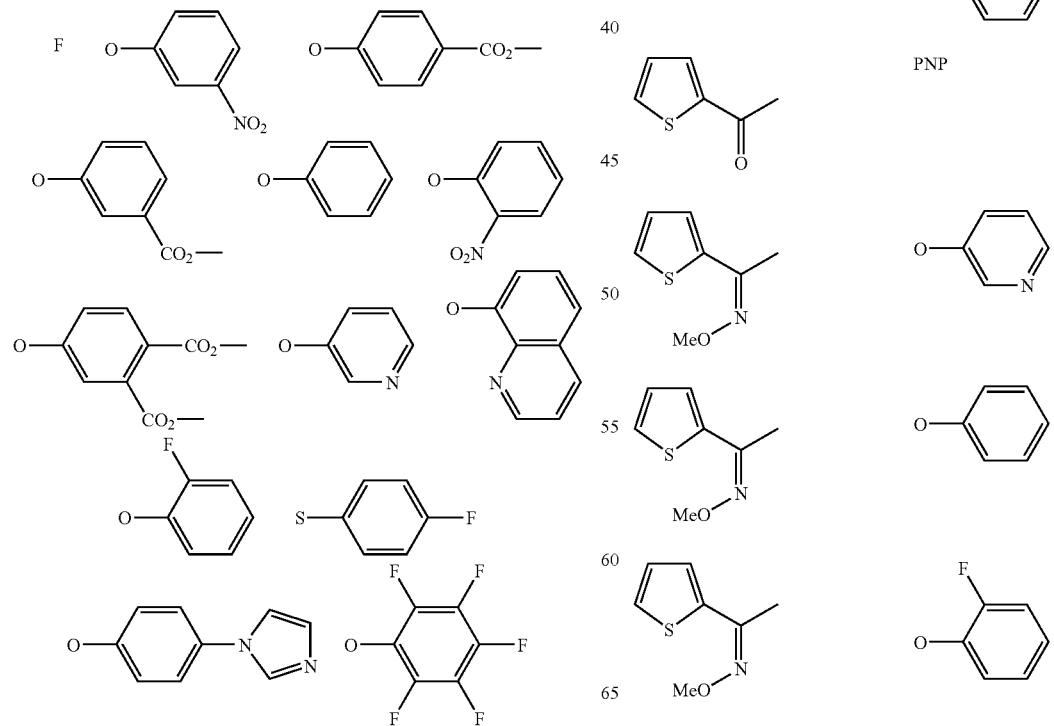

In a preferred embodiment, the compounds according to paragraph [0058] are those in which the combination of $R^1$-L and $R^5$ are selected from the following (in which "PNP" is p-nitrophenoxy):

-continued

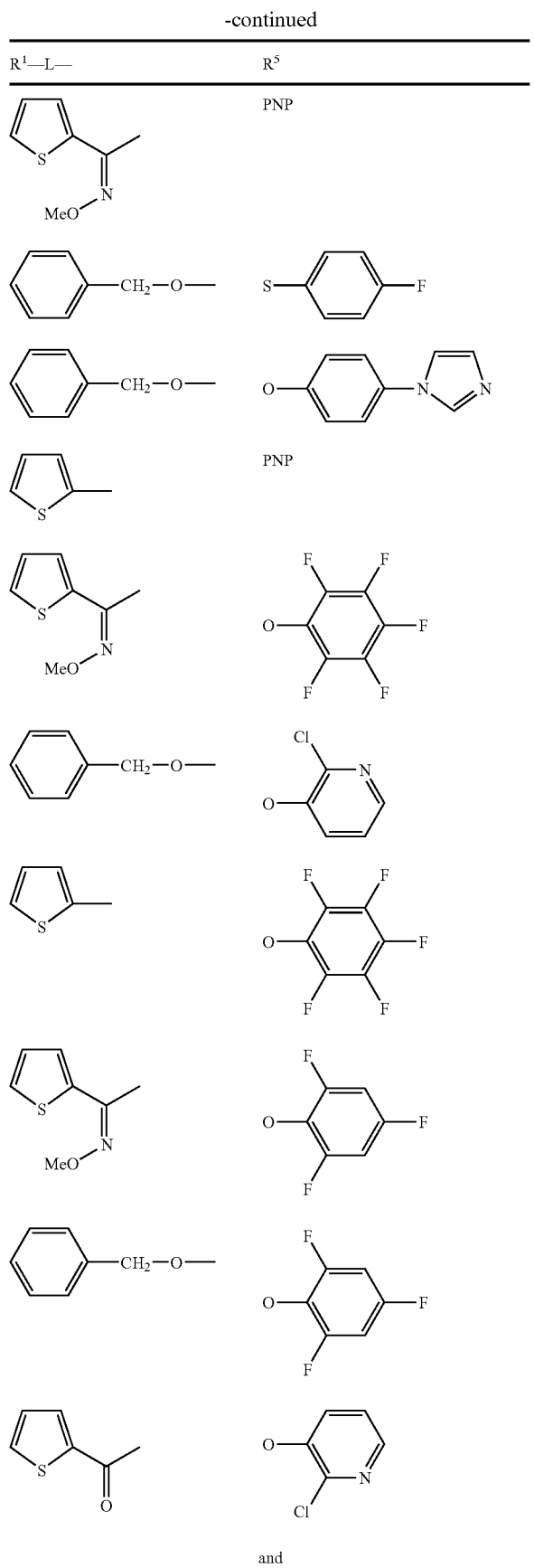

-continued

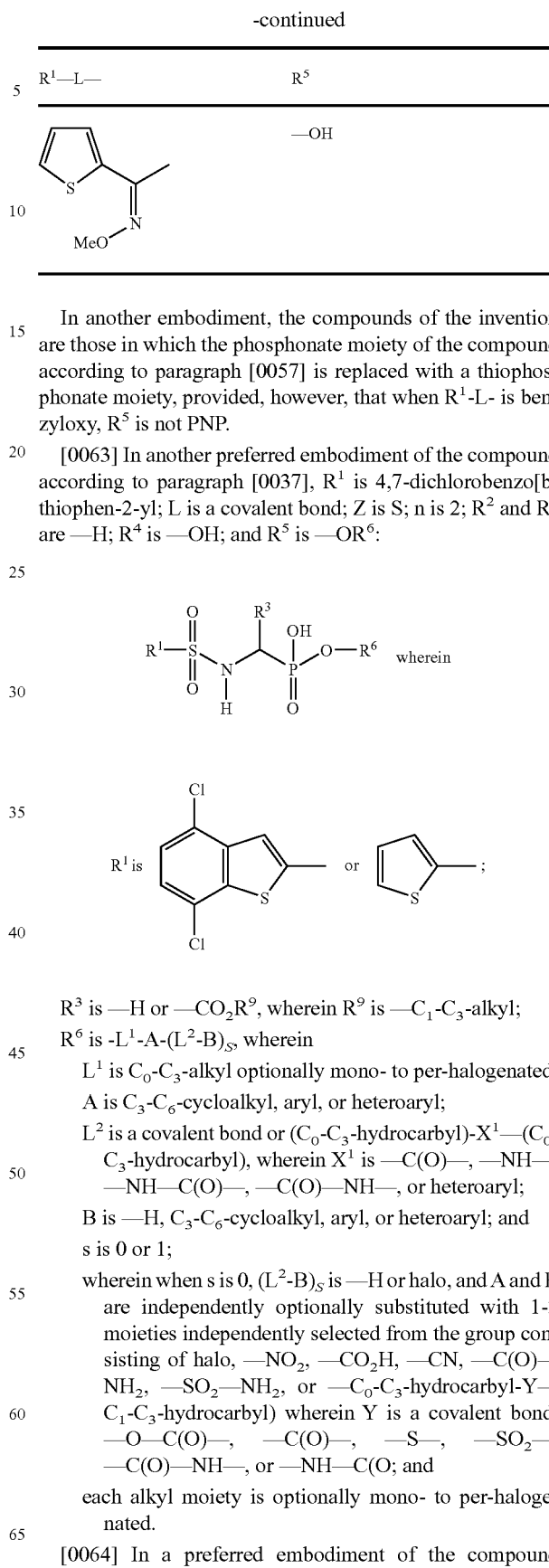

In another embodiment, the compounds of the invention are those in which the phosphonate moiety of the compound according to paragraph [0057] is replaced with a thiophosphonate moiety, provided, however, that when $R^1$-L- is benzyloxy, $R^5$ is not PNP.

[0063] In another preferred embodiment of the compound according to paragraph [0037], $R^1$ is 4,7-dichlorobenzo[b]thiophen-2-yl; L is a covalent bond; Z is S; n is 2; $R^2$ and $R^3$ are —H; $R^4$ is —OH; and $R^5$ is —$OR^6$:

$R^3$ is —H or —$CO_2R^9$, wherein $R^9$ is —$C_1$-$C_3$-alkyl;
$R^6$ is -$L^1$-A-($L^2$-B)$_S$, wherein
  $L^1$ is $C_0$-$C_3$-alkyl optionally mono- to per-halogenated;
  A is $C_3$-$C_6$-cycloalkyl, aryl, or heteroaryl;
  $L^2$ is a covalent bond or ($C_0$-$C_3$-hydrocarbyl)-$X^1$—($C_0$-$C_3$-hydrocarbyl), wherein $X^1$ is —C(O)—, —NH—, —NH—C(O)—, —C(O)—NH—, or heteroaryl;
  B is —H, $C_3$-$C_6$-cycloalkyl, aryl, or heteroaryl; and
  s is 0 or 1;
  wherein when s is 0, ($L^2$-B)$_S$ is —H or halo, and A and B are independently optionally substituted with 1-3 moieties independently selected from the group consisting of halo, —$NO_2$, —$CO_2H$, —CN, —C(O)—$NH_2$, —$SO_2$—$NH_2$, or —$C_0$-$C_3$-hydrocarbyl-Y—$C_1$-$C_3$-hydrocarbyl) wherein Y is a covalent bond, —O—C(O)—, —C(O)—, —S—, —$SO_2$—, —C(O)—NH—, or —NH—C(O; and
  each alkyl moiety is optionally mono- to per-halogenated.

[0064] In a preferred embodiment of the compound according to paragraph [0063], $R^3$ is H and $R^1$ is

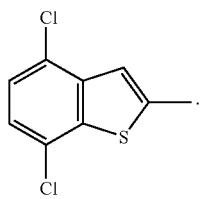

[0065] In another preferred embodiment of the compound according to paragraph [0063], $R^3$ is —$CO_2Et$ and $R^1$ is

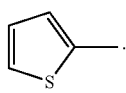

[0066] In a preferred embodiment of the compound according to paragraph [0064], $L^1$ is —O— and A is phenyl or pyridinyl (preferably pyridin-3-yl), each optionally substituted as stated in paragraph [0063].

In one preferred embodiment of the compound of paragraph [0066], s is 0.

In another preferred embodiment of the compound of paragraph [0066], s is 1 and $L^2$ is —C(O)—, —C(O)NH—, —NH—, 1,2,4-oxadiazolyl, or 1,3,4-oxadiazolyl and B is phenyl, pyridinyl, cyclopropyl, or thienyl, wherein B is optionally substituted.

Preferred substituents on the A and B rings include —F, —Cl, —Br, —$CO_2H$, —C(O)O—$CH_3$, —$CF_3$, —$OCH_3$, —$OCF_3$, —$CH_3$, —CN, —C(O)$NH_2$, —S—$CF_3$, —$SO_2CH_3$, —$NO_2$, —$CF_3CF_3$, —$SO_2CF_3$, —$SO_2CF_3CF_3$, and —$SO_2NH_2$.

In a particularly preferred embodiment of the compound according to paragraph [0064] one or both of the following are true:

a. A is selected from phenyl and pyridinyl;

b. B is selected from phenyl, tetraazolyl, cyclopropyl, pyridinyl, and thienyl.

In one preferred embodiment according to paragraph [0065], $R^6$ is phenyl or p-nitro phenyl.

[0072] In another particularly preferred embodiment of the compounds according to paragraph [0064], the compound is selected from those in which —O—$R^6$ is;

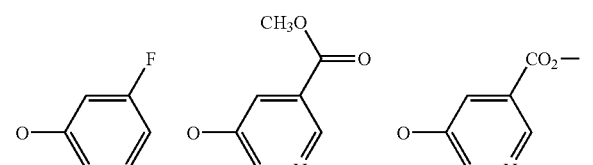

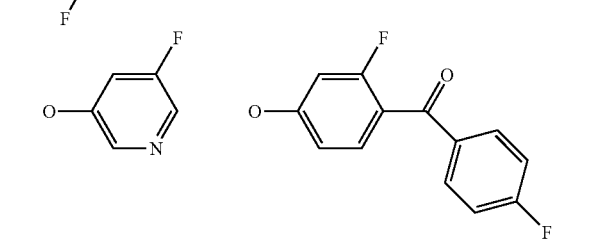

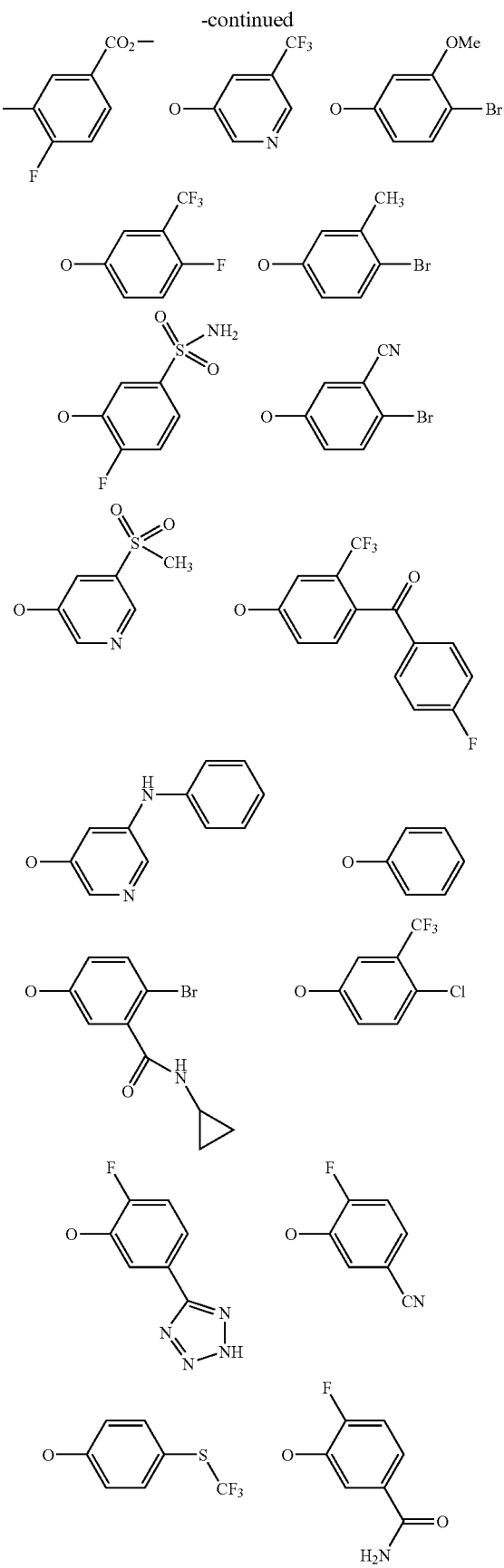

-continued
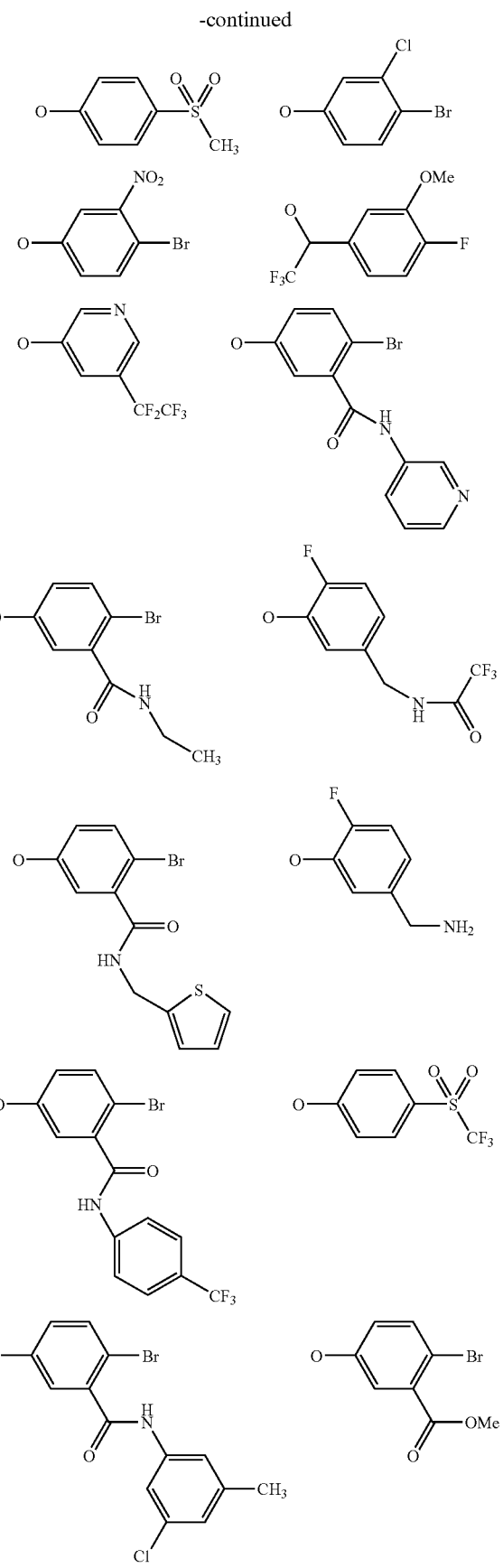
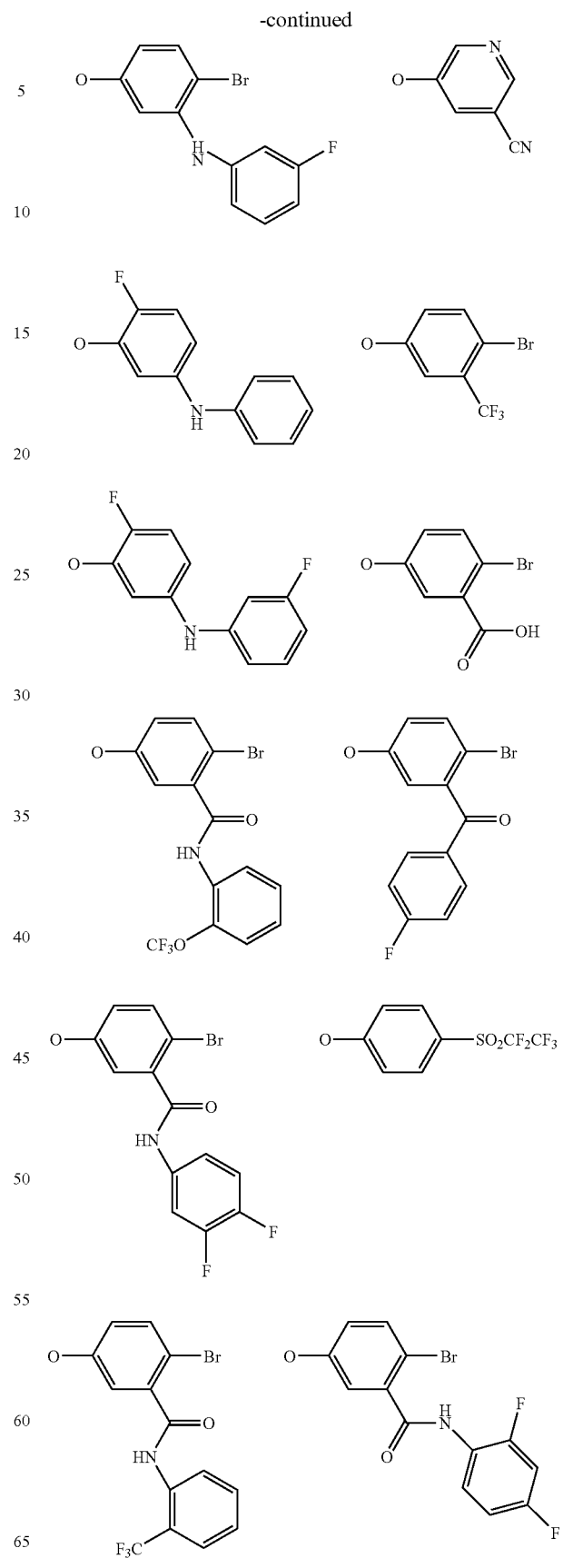

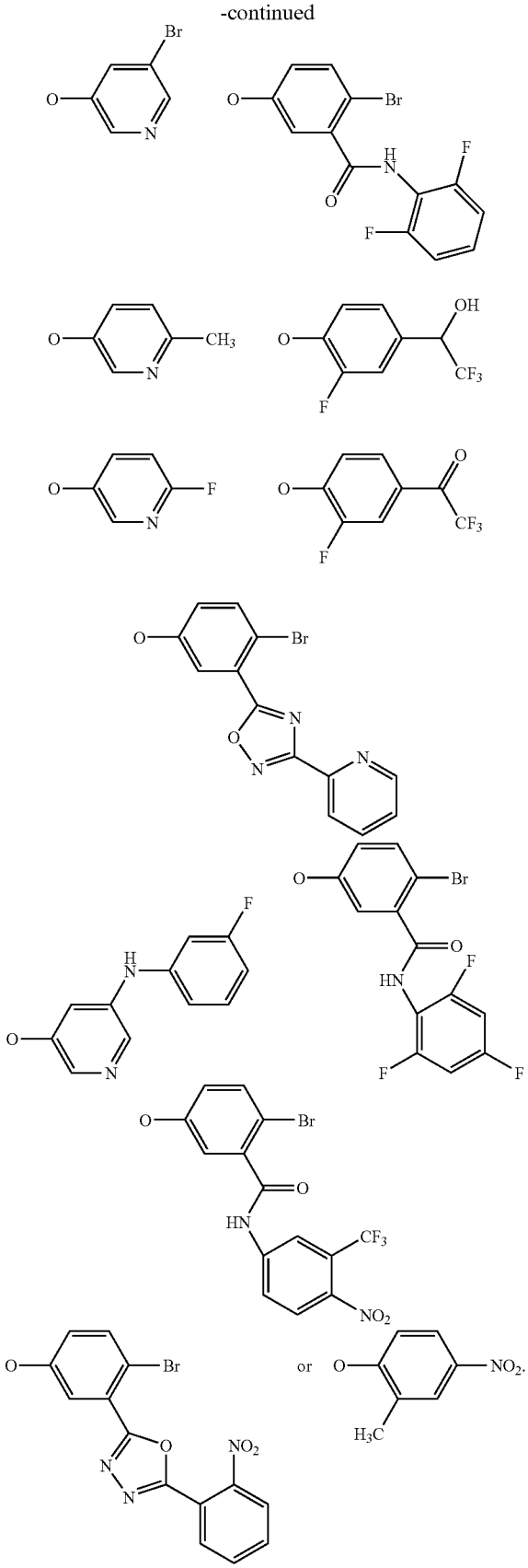

The present inventors have discovered a correlation between hydrophilicity of β-lactamase inhibitors (as measured by log P) and their biological efficacy (expressed as synergy as described in the Examples). The correlation (see FIG. 1) is described by a V-shaped curve, with its point intercepting the x-axis at a log P value of about −0.4 and its arms extending from −0.4 to +0.6. Based on this observed trend in structure-activity relationships, the β-lactamase inhibitors of the invention preferably have high negative or high positive log P values. Preferably, the log P for the inhibitor is $\leq -0.6$ or $\geq 0$, more preferably $\leq -1$ or $\geq 0.2$, still more preferably $\leq -1.2$ or $\geq 0.4$, and most preferably $\leq -1.4$ or $\geq 0.6$. Nikaido and Vaara, Microbiological Reviews 49, 1-32 (1985), and Livermore, Scad. J. Infect. Dis., Suppl. 74, 15-22 (1991), teach that hydrophilicity and cell permeability govern the behavior of antimicrobial agents The compounds of Formula (I) are preferably monoacids ($R^4$=OH). In certain preferred embodiments, the β-lactamase inhibitor is a salt of the compound of Formula (I), the salt preferably being formed by treating the compound of Formula (I) with a base so as to remove the phosphonate hydrogen atom. Non-limiting examples of bases which may be used to deprotonate the compound of Formula (I) include sodium hydroxide, potassium hydroxide, ammonium hydroxide, sodium bicarbonate, potassium bicarbonate, sodium carbonate, and potassium carbonate. Preferably, the counterion thereby introduced is a pharmaceutically acceptable counterion, including without limitation sodium, magnesium, calcium, or ammonium.

Generally, the compounds of the invention can be routinely synthesized using techniques known to those skilled in the art in conjunction with the teachings herein. The compounds of Formula (I) wherein $R^3$=H can be prepared in certain preferred embodiments according to the general synthetic route depicted in Scheme 1. Thus, Arbusov reaction of bromomethylphthalimide with a phosphite such as triethylphosphite is preferably conducted at elevated temperature, e.g., 145° C., in a solvent such as xylenes to afford the phthalimidomethylphosphonate III. Treatment of III with a hydrazine such as methylhydrazine in an alcoholic solvent such as methanol effects phthalimide cleavage to afford the aminomethylphosphonate IV. Treatment of IV with a sulfonyl chloride, sulfinyl chloride, or sulfenyl chloride of the general formula V in an organic solvent such as methylene chloride, and in the presence of a base such as triethylamine, provides the N-sulfonyl-, N-sulfinyl-, or N-sulfenyl-aminomethylphosphonate VI. Treatment of VI with a silyl halide such as trimethylsilyl bromide at room temperature in a solvent such as methylene chloride effects cleavage of the phosphonate ester to provide the phosphonic acid VII. In situ activation of VII with trichloroacetonitrile in pyridine, followed by treatment at 100° C. with an aryl or heteroaryl alcohol, such as phenol or substituted phenol, affords an aryl or heteroaryl phosphonate. Treatment with an aqueous base such as sodium bicarbonate then provides the sodium salt VIII, which corresponds to the compound of Formula (I), wherein $R^2$=$R^3$=H.

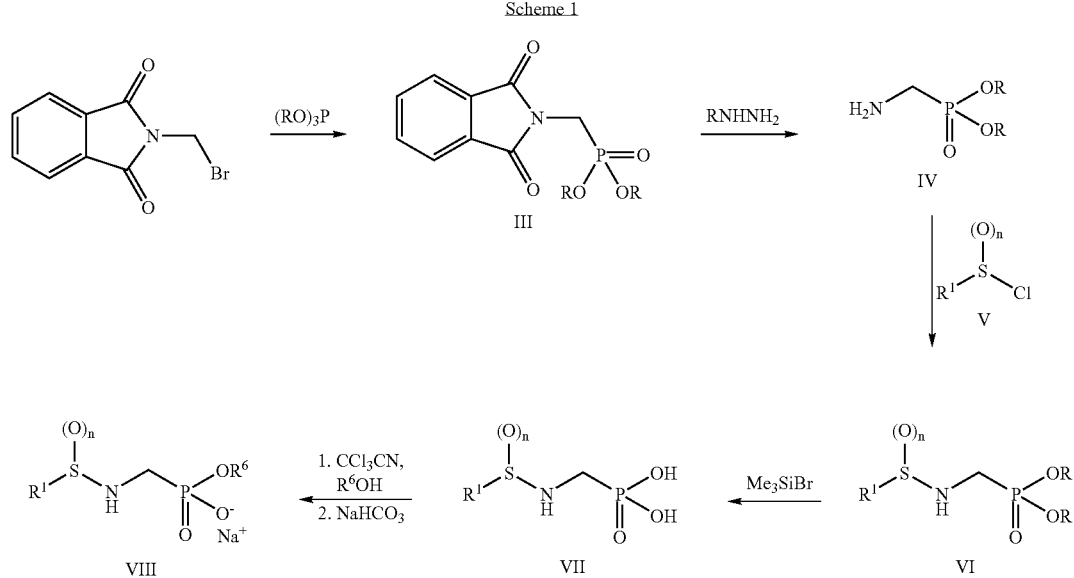

Scheme 1

In certain other preferred embodiments, (sulfonamido)methylphosphonates of formula XIV may be prepared according to the procedures illustrated in Scheme 2. Thus, the sulfonyl chloride of formula IX is treated with ammonium hydroxide to produce the corresponding sulfonamide of formula X. Treatment of X with paraformaldehyde in the presence of a phosphite such as trimethyl phosphite affords the phosphonate diester of formula XI. Deprotection is effected by treatment of XI with a silyl halide such as trimethylsilyl bromide to produce XII, which may be converted to XIV by treatment with trichloroacetonitrile in pyridine, followed by treatment with an aryl or heteroaryl alcohol, as described above. Alternatively, treatment of XII with a chlorinating agent such as sulfuryl chloride or thionyl chloride, followed by treatment with an aryl or heteroaryl alcohol, affords the diester XIII, which is mono-deprotected by treatment with base to afford VIII.

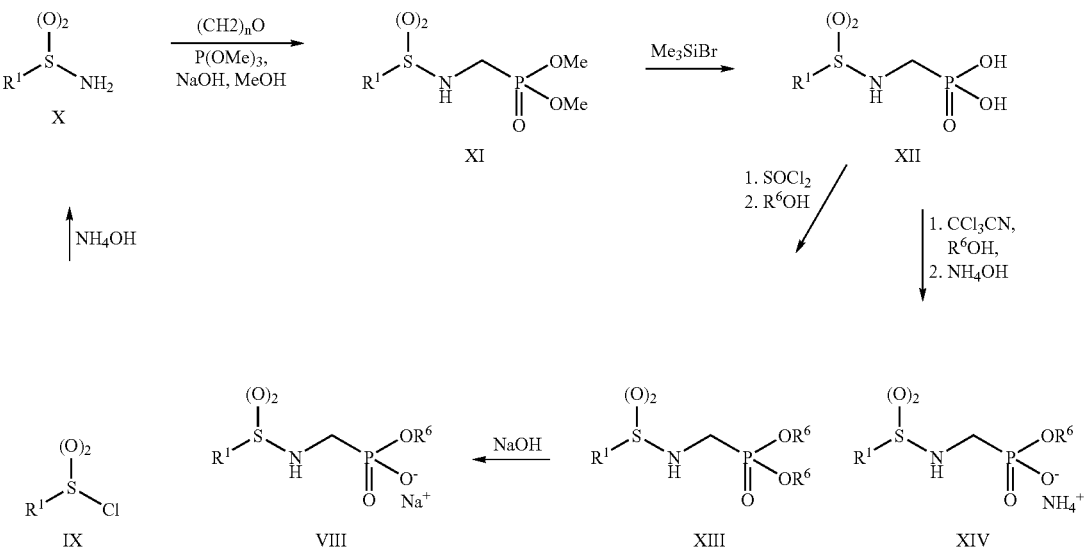

Scheme 2

Compounds of Formula (I), wherein $R^3$ is not hydrogen, are synthesized according to the synthetic route depicted in Scheme 3. Thus, treatment of a sulfonamide X with an aldehyde in the presence of acetyl chloride and a phosphite such as diethylphosphite affords the α-substituted (sulfonamido) methylphosphonate ester XV. The remaining steps are performed analogously to those described for the methods according to Schemes 1 and 2 above to afford the salt XVII, which corresponds to the compound of Formula (I), wherein $R^3$ is not hydrogen.

The compounds of Formula (I), wherein $R^2$ is not hydrogen, may be prepared according to the synthetic route depicted in Scheme 5. Thus, the N-sulfonyl-, N-sulfinyl-, or N-sulfenyl-aminomethylphosphonate VI is treated with an alkyl halide in the presence of a base such as cesium carbonate to afford the N-alkylated derivative XXI. Deprotection and monoesterification as described above then provide the N,N-disubstituted compound XXIII.

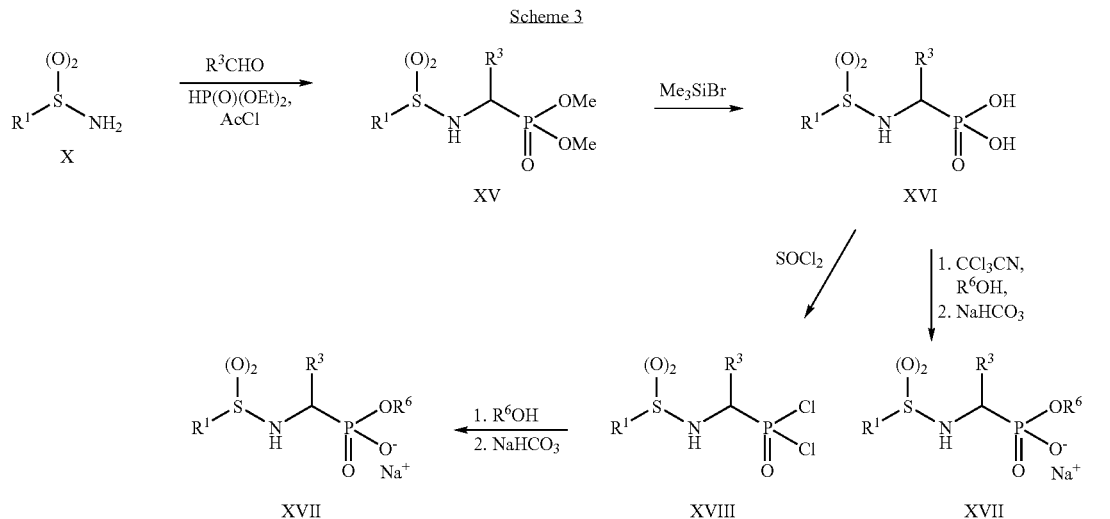

Scheme 3

The compounds of Formula (I), wherein $R^4$ is F, are prepared according to the synthetic route outlined in Scheme 4. Thus, the phosphonic acid VII is treated with a chlorinating agent such as sulfuryl chloride or thionyl chloride to produce the dichlorophosphine oxide XIX, which, without isolation, is then treated with tetrabutylammonium fluoride. Treatment with base then affords the salt XX, which corresponds to the compound of Formula (I), wherein $R^4$ is F.

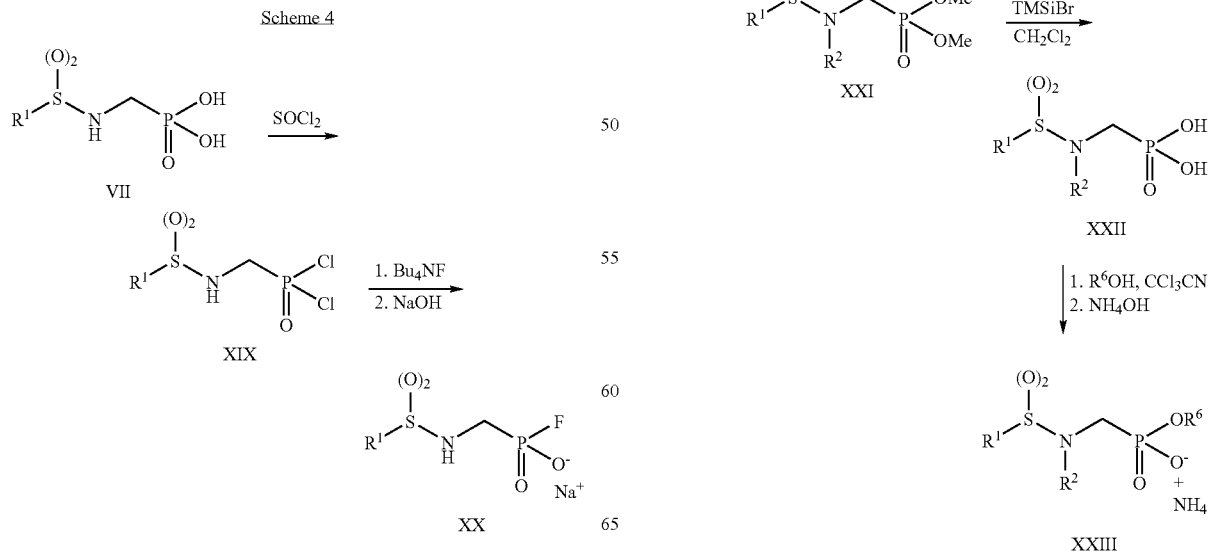

Pharmaceutical Compositions

In a second aspect, the invention provides pharmaceutical compositions comprising a β-lactamase inhibitor of the invention (as described in paragraph [0037]-[0072]) and a pharmaceutically acceptable carrier or diluent.

As employed herein, the term "pro-drug" refers to pharmacologically acceptable derivatives, e.g., esters and amides, such that the resulting biotransformation product of the derivative is the active drug. Pro-drugs are known in the art and are described generally in, e.g., Goodman and Gilmans, "Biotransformation of Drugs", In The Pharmacological Basis of Therapeutics, 8th Ed., McGraw Hill, Int. Ed. 1992, p. 13-15, which is hereby incorporated by reference in its entirety. Compounds of the invention may be formulated by any method well known in the art and may be prepared for administration by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other embodiments, administration may be preferably by the oral route.

Accordingly, another aspect of the invention is a composition comprising a compound of the invention and a pharmaceutically acceptable carrier. The characteristics of the carrier will depend on the route of administration. As used herein, the term "pharmaceutically acceptable" means a non-toxic material that does not interfere with the effectiveness of the biological activity of the active ingredient(s). The term "physiologically acceptable" refers to a non-toxic material that is compatible with a biological system such as a cell, cell culture, tissue, or organism. Thus, compositions and methods according to the invention may contain, in addition to the inhibitor, diluents, fillers, salts, buffers, stabilizers, solubilizers, and other materials well known in the art. The pharmaceutical composition of the invention may also contain other active factors and/or agents which enhance the inhibition of β-lactamases and/or DD-peptidases.

Inhibition of Bacterial Growth

In a third aspect, the invention provides methods for inhibiting bacterial growth, such methods comprising administering to a bacterial cell culture, or to a bacterially infected cell culture, tissue, or organism, a β-lactamase inhibitor of Formula (I) or Formula (II) as defined for the first aspect of the invention (as described in paragraph [0037]-[0072]).

Preferably, the bacteria to be inhibited by administration of a β-lactamase inhibitor of the invention are bacteria that are resistant to β-lactam antibiotics. More preferably, the bacteria to be inhibited are β-lactamase positive strains that are highly resistant to β-lactam antibiotics. The terms "resistant" and "highly resistant" are well-understood by those of ordinary skill in the art (see, e.g., Payne et al., Antimicrobial Agents and Chemotherapy 38:767-772 (1994); Hanaki et al., Antimicrobial Agents and Cheemotherapy 30:1120-1126 (1995)). Preferably, "highly resistant" bacterial strains are those against which the MIC of methicillin is >100 µg/mL. Preferably, "slightly resistant" bacterial strains are those against which the MIC of methicillin is >25 µg/mL.

The methods according to this aspect of the invention are useful for inhibiting bacterial growth in a variety of contexts. In certain preferred embodiments, the compound of the invention is administered to an experimental cell culture in vitro to prevent the growth of β-lactam resistant bacteria. In certain other preferred embodiments the compound of the invention is administered to an animal, including a human, to prevent the growth of β-lactam resistant bacteria in vivo. The method according to this embodiment of the invention comprises administering a therapeutically effective amount of a β-lactamase inhibitor according to the invention for a therapeutically effective period of time to an animal, including a human. Preferably, the β-lactamase inhibitor is administered in the form of a pharmaceutical composition according to the second aspect of the invention.

The terms "therapeutically effective amount" and "therapeutically effective period of time" are used to denote known treatments at dosages and for periods of time effective to show a meaningful patient benefit, i.e., healing of conditions associated with bacterial infection, and/or bacterial drug resistance. Preferably, such administration should be parenteral, oral, sublingual, transdermal, topical, intranasal, intratracheal, or intrarectal. When administered systemically, the therapeutic composition is preferably administered at a sufficient dosage to attain a blood level of inhibitor of at least about 100 micrograms/mL, more preferably about 1 milligrams/mL, and still more preferably about 10 milligrams/mL. For localized administration, much lower concentrations than this may be effective, and much higher concentrations may be tolerated.

In certain preferred embodiments of the method according to this aspect of the invention, a β-lactamase inhibitor according to the invention is co-administered with an antibiotic. Preferably, such co-administration produces a synergistic effect. As employed herein, the terms "synergy" and "synergistic effect" indicate that the effect produced when two or more drugs are co-administered is greater than would be predicted based on the effect produced when the compounds are administered individually. While not wishing to be bound by theory, the present inventors believe that the β-lactamase inhibitors according to the invention act to prevent de-gradation of β-lactam antibiotics, thereby enhancing their efficacy and producing a synergistic effect. In particularly preferred embodiments of the invention, therefore, the co-administered antibiotic is a β-lactam antibiotic. For purposes of this invention, the term "co-administered" is used to denote simultaneous or sequential administration.

Synergy may be expressed as a ratio of the minimum inhibitory concentration (MIC) of an antibiotic tested in the absence of a β-lactamase inhibitor to the MIC of the same antibiotic tested in the presence of the β-lactamase inhibitor. A ratio of one (1) indicates that the β-lactamase inhibitor has no effect on antibiotic potency. A ratio greater than one (1) indicates that the β-lactamase inhibitor produces a synergistic effect when co-administered with the antibiotic agent. Preferably the β-lactamase inhibitor produces a synergy ratio of at least about 2, more preferably about 4, and still more preferably about 8. Most preferably, the β-lactamase inhibitor produces a synergy ratio of at least about 16.

In certain other preferred embodiments, the β-lactamase inhibitor according to the invention may itself have antibiotic activity, and thus potentially can be administered alone or can be co-administered with a β-lactam antibiotic or any other type of antibiotic.

The term "antibiotic" is used herein to describe a compound or composition which decreases the viability of a microorganism, or which inhibits the growth or reproduction of a microorganism. "Inhibits the growth or reproduction" means increasing the generation cycle time by at least 2-fold, preferably at least 10-fold, more preferably at least 100-fold, and most preferably indefinitely, as in total cell death. As used in this disclosure, an antibiotic is further intended to include an antimicrobial, bacteriostatic, or bactericidal agent. Non-limiting examples of antibiotics useful according to this aspect of the invention include penicillins, cephalosporins, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and others. The term "β-lactam antibiotic" is used to designate compounds with antibiotic properties containing a β-lactam functionality. Non-limiting examples of β-lactam antibiotics useful according to this aspect of the invention include penicillins, cephalosporins, penems, carbapenems, and monobactams.

The following examples are intended to further illustrate certain preferred embodiments of the invention, and are not intended to limit the scope of the invention.

EXAMPLE 1

[(4-fluorobenzenesulfonylamino)methyl]-phosphonic acid mono-(2-chloropyridin-3-yl)ester sodium salt (30)

robenzenesulfonyl chloride (1.43 g, 7.36 mmol). The mixture was warmed to room temperature over 2 hours, and stirred for 16 hours. The reaction mixture was then diluted with $CH_2Cl_2$, (50 mL) washed with 1 N HCl (2×25 mL), dried ($MgSO_4$), filtered, and concentrated. Purification by flash chromatography (silica gel; elution with 4% $CH_3OH$ in EtOAc) gave 35 (0.58 g, 35%) as a white solid: $^1H$ NMR (300 MHz, $CDCl_3$) $\delta_H$ 3.29 (d, J=13.2 Hz 2 H), 3.78 (d, $J_{H,P}$=11.1 Hz, 6H), 6.50 (br s, 1H), 7.20 (m, 2H), 7.90 (m, 2H).

Step 3. [(4-fluorobenzenesulfonylamino)methyl]-phosphonic acid (iv).

A solution of diester 35 (0.58 g, 1.95 mmol) in dry $CH_2Cl_2$ (10 mL) and bromotrimethylsilane (1.5 mL, 11.7 mmol) was stirred at room temperature for 5 hours and then concentrated. The resulting residue was dissolved in anhydrous $CH_3OH$ (10 mL) and stirred at room temperature for 20 minutes. Insolubles were filtered, and the filtrate was concentrated.

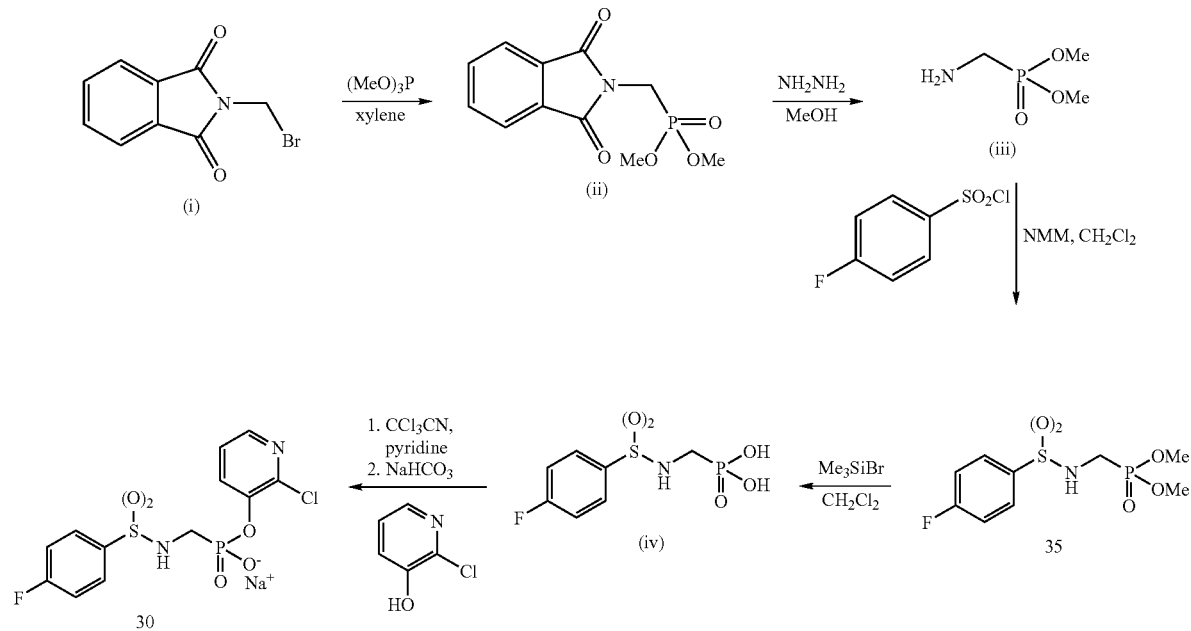

Step 1. Dimethyl (phthalimidomethyl)phosphonate (ii).

A mixture of N-(bromomethyl)phthalimide (i) (10.43 g, 43.46 mmol) and trimethyl phosphite (5.93 g, 47.80 mmol) was heated at reflux in xylene (20 mL) for 6 h. The reaction mixture was then cooled to room temperature and concentrated. Crystallization from $CHCl_3$hexane gave (ii) (7.60 g, 65%) as a white solid: $^1H$ NMR (300 MHz, $CHCl_3$) $\delta_H$ 3.84 (d, $J_{H,P}$=10.8 Hz, 6H), 4.12 (d, J=11.4 Hz, 2H), 7.76 (m, 2H), 7.87 (m, 2H).

Step 2. [(4-fluorobenzenesulfonylamino)methyl]-phosphonic acid dimethyl ester (35).

A solution of phthalimide (ii) (1.50 g, 5.66 mmol) in anhydrous $CH_3OH$ (15 mL) was treated with hydrazide monohydrate (0.29 mL, 6.0 mmol) and stirred at room temperature for 3.5 days. The white phthalyl hydrazide precipitate was filtered off and the filtrate was concentrated at temperature below 20° C. to give dimethyl aminomethyl phosphonate (iii) as a pale yellow oil. Without purification, compound (iii) was dissolved in $CH_2Cl_2$ (20 mL), cooled to 0° C., and treated with N-methylmorpholine (0.84 mL, 7.36 mmol) and p-fluo- Purification by trituration with $CH_2Cl_2$ gave the phosphonic acid (iv) (0.51 g, 97%) as a white solid: $^1H$ NMR (300 MHz, $CD_3OD$) $\delta_H$ 3.17 (d, J=13.5 Hz, 2H), 7.35 (m, 2H), 7.97 (m, 2H).

Step 4. [(4-fluorobenzenesulfonylamino)methyl]-phosphonic acid mono-(2-chloropyridin-3-yl)ester sodium salt (30).

A mixture of compound (iv) (52.6 mg, 0.20 mmol), 2-chloro-3-hydroxypyridine (28.5 mg, 0.22 mmol), and $CCl_3CN$ (100 μl, 1.00 mmol) was heated at 105° C. in pyridine. After 6 h, the reaction mixture was cooled to room temperature and then concentrated. The residue was dissolved in $H_2O$ (10 mL) containing 1 N $NaHCO_3$ (0.6 mL), washed with EtOAc (5 mL×2) and the water layer was lyophilized. Purification by reverse-phase preparative TLC ($C_{18}$-silica gel, 20% $CH_3CN$ in $H_2O$) gave sodium monophosphonate salt 30 (30 mg, 38%) as a white fluffy solid: $^1H$ NMR (300 MHz, $D_2O$) $\delta_H$ 3.17 (d, J=12.6 Hz, 2H), 7.16 (m, 2H), 7.24 (dd, J=4.8, 8.1 Hz, 1H), 7.57 (m, 1H), 7.77 (m, 2H), 7.98 (m, 1H); $^{31}P$ NMR (121 MHz, $CD_3OD$) $\delta_P$ 13.4.

EXAMPLE 2

[(Benzylsulfonylamino)methyl]-phosphonic acid mono-(4-nitrophenyl)ester sodium salt (1)

Following procedures analogous to those described in Example 1, substituting benzylsulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O), $\delta_H$ 3.23 (d, J=11.7 Hz, 2H), 4.40 (s, 2H), 7.18 (d, J=9.3 Hz, 2H), 7.31 (m, 5H), 8.13 (d, J=9.3 Hz, 2H); $^{31}$P NMR (121 MHz, D$_2$O) $\delta_P$ 14.8.

EXAMPLE 3

[(4-Fluorobenzenesulfonylamino)methyl]-phosphonic acid mono-(4-nitrophenyl)ester sodium salt (2)

Following procedures analogous to those described in Example 1, substituting 4-nitrophenol for 2-chloro-3-hydroxypyridine in step 4, the title compound was obtained: $^1$H NMR (300 MHz, CD$_3$OD) $\delta_H$ 3.15 (d, J=13.5 Hz, 2H), 7.31 (m, 2H), 7.40 (d, J=9.3 Hz, 2H), 7.95 (m, 2H), 8.21 (d, J=9.3 Hz, 2H); $^{31}$P NMR (121 MHz, CD$_3$OD) $\delta_P$ 12.4; $^{13}$C NMR (75.4 MHz, CD$_3$OD) $\delta_C$ 40.8 (d, J$_{C,P}$=153 HZ), 117.2 (d, J=22.69 Hz), 122.4 (d, J=4.6 Hz), 126.2, 131.2 (d, J=9.4 Hz), 137.1 (d, J=3.2 Hz), 144.8, 159.4 (d, J=7.7 Hz), 166.5 (d, J$_{C,F}$=252 Hz).

EXAMPLE 4

[(4-Chlorobenzenesulfonylamino)methyl]-phosphonic acid mono-(4-nitrophenyl)ester sodium salt (3)

Following procedures analogous to those described in Example 1, substituting 4-chlorobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.06 (d, J=9.3 Hz, 2H), 7.66 (d, J=9.0 Hz, 2H), 7.40 (d, J=9.0 Hz, 2H), 7.04 (d, J=9.3 Hz, 2H), 3.14 (d, J=12.6 Hz, 2H); $^{31}$P NMR (121 MHz, D$_2$O) $\delta_P$ 14.1.

EXAMPLE 5

[(2-naphthylsulfonylamino)methyl]-phosphonic acid mono-(4-nitro phenyl) ester sodium salt (4)

Following procedures analogous to those described in Example 1, substituting 2-naphthylsulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.19 (br s, 1H), 7.61 (d, J=9.3 Hz, 2H), 7.41-7.82 (m, 6H), 6.73 (d, J=9.3 Hz, 2H), 3.22 (d, J=12.6 Hz, 2H); $^{31}$P NMR (121 MHz, D$_2$O) $\delta_P$ 13.4.

EXAMPLE 6

[(4-Methoxybenzenesulfonylamino)methyl]-phosphonic acid mono-(4-nitrophenyl)ester sodium salt (5)

Following procedures analogous to those described in Example 1, substituting-4-methoxybenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.0 (d, J=9 Hz, 2H, Ar—H), 7.6 (d, J=9 Hz, 2H, Ar—H), 7.0 (d, J=9 Hz, 0.2H, Ar—H), 6.8 (d, J=9 Hz, 2H, Ar—H), 3.8 (s, 3H, CH$_3$), 3.2 (d, J=13 Hz, 2H, CH$_2$).

EXAMPLE 7

[(4-Toluylsulfonylamino)methyl]-phosphonic acid mono-(4-nitrophenyl)ester sodium salt (6)

Following procedures analogous to those described in Example 1, substituting 4-toluysulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta$ 8.1 (d, J=9 Hz, 2H, Ar—H), 7.6 (d, J=9 Hz, 2H, Ar—H), 7.2 (d, J=9 Hz, 2H, Ar—H), 7.0 (d, J=9 Hz, 2H, Ar—H), 3.2 (d, J=13 Hz, 2H, CH$_2$); 2.2 (s, 3H, CH$_3$).

EXAMPLE 8

(Benzenesulfonylamino)methyl]-phosphonic acid mono-(4-nitro-phenyl)ester sodium salt (7)

Following procedures analogous to those described in Example 1, substituting benzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.1 (d, J=9 Hz, 2H, Ar—H), 7.4-7.8 (m, 5H, Ar—H), 7.0 (d, J=9 Hz, 2H, Ar—H), 3.2 (d, J=13 Hz, 2H, CH$_2$).

EXAMPLE 9

[(4-Fluorobenzenesulfonylamino)methyl]-phosphonic acid mono-(3-pyridyl) ester sodium salt (8)

Following procedures analogous to those described in Example 1, substituting 3-hydroxypyridine for 2-chloro-3-hydroxypyridine in step 4, the title compound was obtained: $^1$H NMR (300 MHz, D$_2$O) $\delta_H$ 7.10-8.18 (m, 8H), 3.08 (d, J=12.6 Hz, 2H); $^{31}$P NMR (121 MHz, D$_2$O) $\delta_P$ 14.7.

EXAMPLE 10

[(3,4-Dichlorobenzenesulfonylamino)methyl]-phosphonic acid mono-(4-nitrophenyl)ester sodium salt (9)

Following procedures analogous to those described in Example 1, substituting 3,4-dichlorobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.24 (d, J=9.3 Hz, 2H), 8.01 (d, J=2.1 Hz, 1H), 7.74 (d, J=2.1 Hz, 1H), 7.69 (s, 1H), 7.21 (d, J=9.3 Hz, 2H), 3.39 (d, J=12.3 Hz, 2H); $^{31}$P NMR (121 MHz, D$_2$O) $\delta_P$ 14.2.

EXAMPLE 11

[(1-Naphthylsulfonylamino)methyl]-phosphonic acid mono-(4-nitrophenyl) ester sodium salt (10)

Following procedures analogous to those described in Example 1, substituting 1-napthylsulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.4 (d, 1H, Ar—H), 8.2 (d, 1H, Ar—H), 8.1 (d, 1H, Ar—H), 7.8 (d, J=9 Hz, 2 H. Ar—H), 7.4-7.6 (m, 3H, Ar—H), 6.6 (d, J=9 Hz, 2H, Ar—H), 3.2 (d, J=13 Hz, 2H, CH$_2$); $^{31}$P NMR (121 MHz, D$_2$O) δ$_P$ 16.5 (t, 1 P).

EXAMPLE 12

[(4-Fluorobenzenesulfonylamino)methyl]-phosphonic acid mono-(8-quinolinyl) ester sodium salt (11)

Following procedures analogous to those described in Example 1, substituting 8-hydroxyquinoline for 2-chloro-3-hydroxypyridine in step 4, the title compound was obtained: $^1$H NMR (300 MHz, D$_2$O) δ$_H$ 8.69 (m, 1H), 8.22 (m, 1H), 6.90-7.89 (m, 8H), 3.10 (d, J=13.8 Hz, 2H).

EXAMPLE 13

[(4-Nitrobenzenesulfonylamino)methyl]-phosphonic acid mono-(4-nitrophenyl) ester sodium salt (12)

Following procedures analogous to those described in Example 1, substituting 4-nitrobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ 8.6 (d, 2H, Ar—H), 8.4 (d, J=9 Hz, 2H, Ar—H), 8.0 (d, 2H, Ar—H), 7.4 (d, J=9 Hz, 2H, Ar—H), 3.2 (d, J=13 Hz, 2H, CH$_2$); $^{31}$P NMR (121 MHz, D$_2$O) δ$_P$, 17.5 (t, 1 P).

EXAMPLE 14

[(2-Nitrobenzenesulfonylamino)methyl]-phosphonic acid mono-(4-nitrophenyl) ester sodium salt (13)

Following procedures analogous to those described in Example 1, substituting 2-nitrobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ$_H$ 8.0 (d, J=9 Hz, 2H, Ar—H), 7.8 (s, 1H, Ar—H), 7.6 (s, 1H, Ar—H), 7.6 (d, 2H, Ar—H), 7.1 (d, J=9 Hz, 2H, Ar—H), 3.2 (d, J=13 Hz, 2H); $^{31}$P NMR (121 MHz, D$_2$O) δ$_P$, 17.5 (t, 1 P).

EXAMPLE 15

[(2,5-Dichlorobenzenesulfonylamino)methyl]-phosphonic acid mono-(4-nitrophenyl) ester sodium salt (14)

Following procedures analogous to those described in Example 1, substituting 2,5-dichlorobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ$_H$ 8.1 (d, J=9 Hz, 2H, Ar—H), 7.8 (s, 1H, Ar—H), 7.4 (s, 2H, Ar—H), 7.1 (d, J=9 Hz, Ar—H), 3.2 (d, J=13 Hz, 2H, CH$_2$); $^{31}$P NMR (121 MHz, D$_2$O) δ$_P$ 17.5 (t, 1 P).

EXAMPLE 16

[(Thiophene-2-sulfonylamino)methyl]-phosphonic acid mono-(4-nitrophenyl) ester sodium salt (15)

Following procedures analogous to those described in Example 1, substituting 2-thiophenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ$_H$ 8.09 (d, J=9.6 Hz, 2H), 7.69 (dd, J=5.1; 1.5 Hz, 1H), 7.57 (dd, J=3.6; 1.2 Hz, 1H), 7.12 (d, J=9.6 Hz, 2H), 7.05 (dd, J=5.1; 3.6 Hz, 1H), 3.16 (d, J=12.9 Hz, 2H).

EXAMPLE 17

[(4-tert-Butylbenzenesulfonylamino)methyl]-phosphonic acid mono-(4-nitrophenyl) ester sodium salt (16)

Following procedures analogous to those described in Example 1, substituting 4-tert-butylbenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ$_H$ 8.2 (d, J=9 Hz, 2H, Ar—H), 7.8 (m, 2H, Ar—H), 7.6 (m, 2H, Ar—H), 7.1 (d, J=9 Hz, 2H, Ar—H), 3.2 (d, J=13 Hz, 2H, CH$_2$), 1.2 (s, 9H, t-Bu); $^{31}$P NMR (121 MHz, D$_2$O) δ$_P$ 18 (t, 1P).

EXAMPLE 18

[(4-Trifluoromethylbenzenesulfonylamino)methyl]-phosphonic acid mono-(4-nitrophenyl) ester sodium salt (17)

Following procedures analogous to those described in Example 1, substituting 4-trifluoromethylbenzenesulfonyl for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ$_H$ 8.2 (d, J=9 Hz, 2H, Ar—H), 7.8 (m, 2H, Ar—H), 7.6 (m, 2H, Ar—H), 7.1 (d, J=9 Hz, 2H, Ar—H), 3.2 (d, J=13 Hz, 2H, CH$_2$); $^{31}$P NMR (121 MHz, D$_2$O) δ$_P$ 18 (t, 1P).

EXAMPLE 19

[(2,4-Dinitrobenzenesulfonylamino)methyl]-phosphonic acid mono-(4-nitrophenyl)ester sodium salt (18)

Following procedures analogous to those described in Example 1, substituting 2,4-dinitrobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ$_H$ 8.61 (m, 1H); 8.35 (m, 1H), 8.15 (m, 1H), 7.98 (d, J=9.0 Hz, 2H); 7.02 (d, J=9.0 Hz, 2H), 3.41 (d, J=11.4 Hz, 2H).

EXAMPLE 20

[(8-Quinolylsulfonylamino)methyl]-phosphonic acid mono-(4-nitrophenyl) ester sodium salt (19)

Following procedures analogous to those described in Example 1, substituting 8-quinolylsulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) δ$_H$ 6.68-8.78 (m, 10H), 3.13 (d, J=12.9 Hz, 2H); $^{31}$P NMR (121 MHz, D$_2$O) δ$_P$ 13.4.

EXAMPLE 21

[2,4,6-trimethylbenzenesulfonylamino)methyl]-phosphonic acid mono-(4-nitrophenol) ester sodium salt (21)

Following procedures analogous to those described in Example 1, substituting 2,4,6-trimethylbenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.2 (d, J=9 Hz, 2H, Ar—H), 6.8 (s, 2H, Ar—H), 3.2 (d, J=13 Hz, 2H, CH$_2$), 2.3 (s, 6H, CH$_3$), 2.1 (s, 3H, CH$_3$); $^{31}$P NMR (121 MHz, D$_2$O) $\delta_P$ 18 (t, 1 P).

EXAMPLE 22

[(4-Chloro-3-nitrobenzenesulfonylamino)methyl]-phosphonic acid mono-(4-nitrophenyl) ester sodium salt (22)

Following procedures analogous to those described in Example 1, substituting 4-chloro-3-nitrobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.4 (s, 1H, Ar—H), 8.2 (d, J=9 Hz, 2H, Ar—H), 7.9 (d, 1 H. Ar—H), 7.7 (d, 1H, Ar—H), 7.2 (s, 2H, Ar—H), 3.2 (d, J=13 Hz, 2H, CH$_2$); $^{31}$P NMR (121 MHz, D$_2$O) $\delta_P$ 18 (t, 1 P).

EXAMPLE 23

[2-Bromobenzenesulfonylamino)methyl]-phosphonic acid mono-(4-nitrophenyl) ester sodium salt (23)

Following procedures analogous to those described in Example 1, substituting 2-bromobenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta$ 8.2 (d, J=9 Hz, 2H, Ar—H), 8.1 (s, 1H, Ar—H), 7.6 (d, 1H, Ar—H), 7.4 (m, 2H, Ar—H), 7.2 (s, 2H, Ar—H), 3.2 (d, J=13 Hz, 2H, CH$_2$); $^{31}$P NMR (121 MHz, D$_2$O) $\delta_P$ 17 (t, 1P).

EXAMPLE 24

[(3-Pyridinesulfonylamino)methyl]-phosphonic acid mono-(4-nitrophenyl) ester sodium salt (24)

Following procedures analogous to those described in Example 1, substituting 3-pyridinesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.80 (s, 1 H), 8.55 (d, J=4.8 Hz, 1H), 8.13 (d, J=8.1 Hz, 1H), 8.03 (d, J=9.0 Hz, 2H), 7.46 (dd, J=4.8, 8.1 Hz, 1H), 7.05 (d, J=9.0 Hz, 2H), 3.19 (d, J=12.3 Hz, 2H); $^{31}$P NMR (121 MHz, D$_2$O) $\delta_P$ 13.7.

EXAMPLE 25

[(3-Pyridinesulfonylamino)methyl]-phosphonic acid mono-(3-pyridinyl)ester sodium salt (25)

Following procedures analogous to those described in Example 1, substituting 3-pyridinesulfonyl chloride for 4-fluorobenzenesulfonyl chloride in step 2 and 3-hydroxypyridine for 2-chloro-3-hydroxypyridine in step 4, the title compound was obtained: $^1$H NMR (300 MHz, CD$_3$OD) $\delta_H$ 3.17 (d, J=13.2 Hz, 2H), 7.37 (dd, J=4.8, 8.1 Hz, 1H), 7.57-7.69 (m, 2H), 8.23-8.29 (m, 2H), 8.40 (br s, 1H), 8.74 (dd, J=1.2, 4.8 Hz, 1H), 9.00 (d, J=1.5 Hz, 1H); $^{31}$P NMR (121 MHz, CD$_3$OD) $\delta_P$ 12.1; $^{13}$C NMR (75.4 MHz, CD$_3$OD) $\delta_C$ 40.6 (d, J=152 Hz), 125.5, 125.7, 130.5 (d, J=3.8 Hz), 136.8, 138.2, 143.5 (d, J=4.3 Hz), 144.7, 148.7, 151.2 (d, J=7.7 Hz), 153.8.

EXAMPLE 26

[(3-Dibenzofuransulfonylamino)methyl]-phosphonic acid mono-(4-nitrophenyl) ester sodium salt (27)

Following procedures analogous to those described in Example 1, substituting 3-dibenzofuransulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.2 (s, 1H, Ar—H), 7.8 (d, J=9 Hz, 2H, Ar—H), 7.45 (m, 3H, Ar—H), 7.2 (t, J=7.5 Hz, 2H, Ar—H), 6.8 (d, J=9 Hz, 2H, Ar—H), 3.2 (d, J=12.9 Hz, 2H, CH$_2$); $^{31}$P NMR (121 MHz, D$_2$O) $\delta_P$17.17 (t, J=12.2 Hz, 1 P).

EXAMPLE 27

[(2-Thiophenesulfonylamino)methyl]-phosphonic acid mono-(2,4,6-trifluorophenyl) ester sodium salt (28)

Following procedures analogous to those described in Example 1, substituting 2-thiophenesulfonyl chloride for 4-fluorobenzenesulfonyl chloride in step 2 and 2,4,6-trifluorophenol for 2-chloro-3-hydroxypyridine in step 4, the title compound was obtained: $^1$H NMR (300 MHz, D$_2$O) $\delta_H$ 7.73 (dd, J=5.0; 1.5 Hz, 1H), 7.62 (dd, J=3.6, 1.5 Hz, 1H), 7.10 (dd, J=5.0, 3.6 Hz, 1H), 6.77 (m, 2H), 3.20 (d, J=13.2 Hz, 2H).

EXAMPLE 28

(2-Pyridinesulfonylamino)methyl]-phosphonic acid mono-(4-nitrophenyl) ester sodium salt (31)

Following procedures analogous to those described in Example 1, substituting 2-pyridinesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O), $\delta_H$ 8.49 (m, 1H), 8.08 (d, J=9.0 Hz, 2H), 7.86-7.98 (m, 2H), 7.52 (m, 1H), 7.11 (d, J=9.0 Hz, 2H), 3.28 (d, J=12.3 Hz, 2H); $^{31}$P NMR (121 MHz, D$_2$O) $\delta_P$ 13.7.

EXAMPLE 29

[(2-Pyridinesulfonylamino)methyl]-phosphonic acid mono-(2-chloro-pyridine-3-yl)ester sodium salt (32)

Following procedures analogous to those described in Example 1, substituting 2-pyridinesulfonyl chloride for 4-fluorobenzenesulfonyl chloride in step 2, the title compound was obtained: $^1$H NMR (300 MHz, D$_2$O), $\delta_H$ 8.48 (d, J=4.8 Hz, 1H), 7.83-7.98 (m, 3H), 7.57 (d, J=8.1 Hz, 1H), 7.51 (m, 1H), 7.23 (dd, J=4.8, 8.1 Hz, 1H), 3.30 (d, J=12.0 Hz, 2H); $^{31}$P NMR (121 MHz, D$_2$O) $\delta_P$ 19.0.

EXAMPLE 30

[(5-Isoquinolinesulfonylamino)methyl]-phosphonic acid mono-(4-nitrophenyl) ester sodium salt (33)

Following procedures analogous to those described in Example 1, substituting 5-isoquinolinesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 8.92 (br s, 1H), 8.31 (br s, 1H), 8.21 (dd, J=1.0, 7.5 Hz, 1H), 8.12 (d, J=6.3 Hz, 1H), 7.98 (d, J=8.1 Hz, 1H), 7.62 (d, J=9.0 Hz, 2H), 7.52 (m, 1H), 6.53 (d, J=9.0 Hz, 2H), 3.18 (d, J=12.9 Hz, 2H); $^{31}$P NMR (121 MHz, D$_2$O) $\delta_P$ 12.5.

EXAMPLE 31

[(2-Pyridinesulfonylamino)methyl]-phosphonic acid (34)

Following procedures analogous to those described in Example 1, steps 2-3, substituting 2-pyridinesulfonyl chloride for 4-fluorobenzenesulfonyl chloride in step 2, the title compound was obtained: $^1$H NMR (300 MHz, D$_2$O) $\delta_H$ 8.53 (m, 1H), 7.90-8.05 (m, 2H), 7.58 (m, 1H), 3.07 (d, J=12.6 Hz, 2H); $^{31}$P NMR (121 MHz, D$_2$O) $\delta_P$ 15.8.

EXAMPLE 32

[(5-Isoquinolinesulfonylamino)methyl]-phosphonic acid mono-(2-chloropyridin-3-yl)ester sodium salt (36)

Following procedures analogous to those described in Example 1, substituting 5-isoquinolinesulfonyl chloride for 4-fluorobenzenesulfonyl chloride in step 2, the title compound was obtained: $^1$H NMR (300 MHz, D$_2$O) $\delta_H$ 9.00 (s, 1H), 8.36 (d, J=6.0 Hz, 1H), 8.29 (d, J=7.2 Hz, 1 H), 8.19 (d, J=6.0 Hz, 1H), 8.06 (d, J=7.5 Hz, 1H), 7.74 (d, J=4.8 Hz, 1H), 7.57 (m, 1H), 7.07 (d, J=8.1 Hz, 1H), 6.92 (dd, J=4.8, 8.1 Hz, 1H), 3.24 (d, J=11.7 Hz, 2H); $^{31}$P NMR (121 MHz, D$_2$O) $\delta_P$ 12.1.

EXAMPLE 33

[(4-Fluorobenzenesulfonylamino)methyl]-phosphonic acid mono-(2-bromopyridin-3-yl) ester sodium salt (37)

Following procedures analogous to those described in Example 1, substituting 2-bromo-3-hydroxypyridine for 2-chloro-3-hydroxypyridine in step 4, the title compound was obtained: $^1$H NMR (300 MHz, D$_2$O) $\delta$ 7.95 (d, J=4.8 Hz, 2H), 7.76 (m, 2H), 7.51 (d, J=8.1 Hz, 1H), 7.25 (dd, J=4.8, 8.1 Hz, 1H), 7.16 (m, 2H), 3.17 (d, J=12.9 Hz, 2H).

EXAMPLE 34

[(2-Thiophenesulfonylamino)methyl]-phosphonic acid mono-(2-chloropyridin-3-yl)ester sodium salt (38)

Following procedures analogous to those described in Example 1, substituting 2-thiophenesulfonyl chloride for 4-fluorobenzenesulfonyl chloride in step 2, the title compound was obtained: $^1$H NMR (300 MHz, D$_2$O) $\delta_H$ 7.99 (d, J=4.8 Hz, 1H), 7.70 (d, J=4.8 Hz, 1H), 7.58 (m, 2H), 7.26 (dd, J=8.4; 5.1 Hz, 1H), 7.06 (t, J=4.8 Hz, 1H), 3.21 (d, J=12.9 Hz, 2H).

EXAMPLE 35

[(4-phenylbenzenesulfonylamino)methyl]-phosphonic acid mono-(4-nitrophenyl)ester sodium salt (39)

Following procedures analogous to those described in Example 1, substituting 4-phenylbenzenesulfonyl chloride for 4-fluorobenzenesulfonyl chloride in step 2 and 4-nitrophenol for 2-chloro-3-hydroxypyridine in step 4, the title compound was obtained: $^1$H NMR (300 MHz, D$_2$O) $\delta_H$ 7.87 (d, J=9.0 Hz, 2H), 7.73 (d, J=8.1 Hz, 2H), 7.59 (d, J=8.1 Hz, 2H), 7.49 (d, J=6.6 Hz, 2 H), 7.35 (m, 3H), 6.91 (d, J=9.0 Hz, 2H), 3.16 (d, J=12.3 Hz, 2H); $^{31}$P NMR (121 MHz, D$_2$O) $\delta_P$ 12.6.

EXAMPLE 36

[(4-Phenylbenzenesulfonylamino)methyl]-phosphonic acid mono-(2-chloro-pyridine-3-yl)ester sodium salt (40)

Following procedures analogous to those described in Example 1, substituting 4-phenylbenzenesulfonyl chloride for 4-fluorobenzenesulfonyl chloride in step 2, the title compound was obtained: $^1$H NMR (300 MHz, D$_2$O) $\delta_H$ 8.04 (m, 1H), 7.78 (d, J=8.4 Hz, 2H), 7.65 (d, J=8.4 Hz, 2H), 7.54 (d, J=6.6 Hz, 2H), 7.31-7.43 (m, 3H), 7.16 (m, 1H), 3.14 (d, J=12.6 Hz, 2H); $^{31}$P NMR (121 MHz, D$_2$O) $\delta_P$ 14.3.

EXAMPLE 37

[(5-Bromo-2-thiophenesulfonylamino)methyl]-phosphonic acid mono-(4-nitrophenyl) ester sodium salt (41)

Following procedures analogous to those described in Example 1, substituting 5-bromo-2-thiophenesulfonyl chloride for 4-fluorobenzenesulfonyl chloride in step 2, the title compound was obtained: $^1$H NMR (300 MHz, D$_2$O) $\delta_H$ 8.10 (d, J=8.4 Hz, 2H), 7.30 (d, J=4.2 Hz, 1H), 7.10 (d, J=8.4 Hz, 2H), 7.02 (d, J=4.2 Hz, 1H), 3.18 (d, J=12.9 Hz, 2H); $^{31}$P NMR (121 MHz, D$_2$O) $\delta_P$ 13.3.

EXAMPLE 38

[(5-Bromo-2-thiophenesulfonylamino)methyl]-phosphonic acid mono-(2-chloropyridin-3-yl)ester sodium salt (42)

Following procedures analogous to those described in Example 1, substituting 5-bromo-2-thiophenesulfonyl chloride for 4-fluorobenzenesulfonyl chloride in step 2, the title compound was obtained: $^1$H NMR (300 MHz, CD$_3$OD) $\delta_H$ 7.96 (d, J=4.8 Hz, 1H), 7.55 (d, J=8.1 Hz, 1H), 7.31 (d, J=3.9 Hz, 1H), 7.22 (dd, J=4.8, 8.1 Hz, 1H), 7.01 (d, J=3.9 Hz, 1H), 3.21 (d, J=12.9 Hz, 2H); $^{31}$P NMR (121 MHz, CD$_3$OD) $\delta_P$ 15.1.

EXAMPLE 39

[(2-Thiophenesulfonylamino)methyl]-phosphonic acid (43)

Following procedures analogous to those described in Example 1, steps 2-3, substituting 2-thiophenesulfonyl chloride for 4-fluorobenzenesulfonyl chloride in step 2, the title compound was obtained: $^1$H NMR (300 MHz, CD$_3$OD) $\delta_H$ 7.79 (dd, J=4.8, 12.6 Hz, 1H), 7.64 (dd, J=3.9, 1.2 Hz, 1H), 7.17 (dd, J=4.8, 3.9 Hz, 1H), 3.16 (d, J=13.2 Hz, 2H).

EXAMPLE 40

[(5-Bromo-2-thiophenesulfonylamino)methyl]-phosphonic acid (58)

Following procedures analogous to those described in Example 1, steps 2-3, substituting 5-bromo-2-thiophenesulfonyl chloride for 4-fluorobenzenesulfonyl chloride in step 2, the title compound was obtained: $^1$H NMR (300 MHz, CD$_3$OD) $\delta_H$ 7.47 (d, J=3.9 Hz, 1H), 7.25 (d, J=3.9 Hz, 1H), 3.23 (d, J=13.5 Hz, 2H); $^{31}$P NMR (121 MHz, CD$_3$OD) $\delta_P$ 17.9; $^{13}$C NMR (75.4 MHz, CD$_3$OD) $\delta_C$ 40.8 (d, J=157 Hz), 120.3, 132.1, 133.7, 143.0.

EXAMPLE 41

[(3-(N-Phenylcarbamoylamino)-sulfonylamino)methyl]-phosphonic acid (59)

Following procedures analogous to those described in Example 1, steps 2-3, substituting 3-(N-phenylcarbamoylamino)-sulfonyl chloride for 4-fluorobenzenesulfonyl chloride in step 2, the title compound was obtained: $^1$H NMR (300 MHz, DMSO-d$_6$) $\delta_H$ 9.11 (s, 1H), 8.18 (s, 1H), 7.73 (d, J=9.0 Hz, 2H), 7.63 (d, J=8.7 Hz, 2H), 7.56 (m, 1H), 7.46 (d, J=7.8 Hz, 2H), 7.30 (app. t, J=7.8 Hz, 2H), 7.0 (m, 1H), 2.80 (d, J=13.5 Hz, 2H), $^{31}$P NMR (121 MHz, DMSO-d$_6$) $\delta_P$ 17.0.

EXAMPLE 42

[(2-Thiophenesulfonylamino)methyl]-phosphonic acid mono-(4-chlorophenyl) ester ammonium salt (61)

Following procedures analogous to those described in Example 1, substituting 2-thiophenesulfonyl chloride for 4-fluorobenzenesulfonyl chloride in step 2 and 4-chlorophenol for 2-chloro-3-hydroxypyridine in step 4, the title compound was obtained: $^1$H NMR (400 MHz, D$_2$O) $\delta_H$ 7.87 (dd, J=1.5, 5 Hz, 1H, Ar—H), 7.73 (dd, J=1.5, 4 Hz, 1H, Ar—H), 7.34-7.37 (m, 2H, Ar—H), 7.23 (dd, J=4, 5 Hz, 1H, Ar—H), 7.06-7.08 (m, 2H, Ar—H), 3.26 (d, J=27.0 Hz, 2H, NCH$_2$P); $^{31}$P NMR: (164 MHz, D$_2$O) $\delta_P$ 14.4; $^{13}$C NMR (100 MHz, D$_2$O) $\delta_C$ 39.5 (d, J=152 Hz), 123.0 (d, J=3.5 Hz), 128.9, 129.8, 130.2, 134.2, 134.6, 138.1, 150.7.

EXAMPLE 43

[(3-(N-Phenylcarbamoylamino)benzenesulfonylamino)methyl]-phosphonic acid mono-(2-chloropyridin-3-yl)ester sodium salt (70)

Following procedures analogous to those described in Example 1, substituting (N-phenylcarbamoylamino)sulfonyl chloride for 4-fluorobenzenesulfonyl chloride in step 2, the title compound was obtained: $^1$H NMR (300 MHz, CD$_3$OD) $\delta$ 8.08 (m, 1H), 7.64-7.91 (m, 5H), 7.49 (m, 2H), 7.34 (m, 3H), 7.08 (m, 1H), 3.20 (d, J=13.8 Hz, 2H); $^{31}$P NMR (121 MHz, CD$_3$OD) $\delta_P$ 13.2.

EXAMPLE 44

[(5-Bromo-2-thiophenesulfonylamino)methyl]-phosphonic acid mono-(5-chloropyridin-3-yl)ester sodium salt (71)

Following procedures analogous to those described in Example 1, substituting 5-bromo-2-thiophenesulfonyl chloride for 4-fluorobenzenesulfonyl chloride in step 2 and 5-chloro-3-hydroxypyridine for 2-chloro-3-hydroxypyridine in step 4, the title compound was obtained: $^1$H NMR (300 MHz, D$_2$O) $\delta_H$ 8.20 (br.s. 1H), 8.11 (br.s. 1H), 7.54 (m, 1H), 7.33 (d, J=4.2 Hz, 1H), 7.05 (d, J=4.2 Hz, 1H), 3.20 (d, J=12.6 Hz, 2H); $^{31}$P NMR (121 MHz, D$_2$O) $\delta_P$ 13.9.

EXAMPLE 45

Phenylsulfonylhydrazinyl-mono-(4-nitrophenyl)-phosphonamide (189)

Benzenesulfonyl hydrazide (0.5 g, 2.9 mmol) and pyridine (0.27 g, 3.2 mmol) in 50 mL of dry THF were added to a stirring solution of p-nitrophenylphosphoryl dichloride (0.75 g, 2.9 mmol) in 50 mL of dry THF at 0° C. After addition was complete, the solution was brought to room temperature and stirring was continued for 4 more hours. Finally, 1 N NaOH (9 mL) was added with stirring. Volatiles were removed, and the remaining aqueous solution was freeze-dried. The resultant crude product was more than 85% pure, but final purification was accomplished by preparative HPLC on an SMT C18 column using water/acetonitrile gradient. Analytical HPLC under similar conditions showed the product to be one peak (>95% pure). $^1$H NMR (300 MHz, D$_2$O): $\delta_H$ 8.1 (d, 2H, p-nitrophenyl, 7.4-7.65 (m, 5H, Ar—H), 7.1 (d, 2H, p-nitrophenyl); $^{31}$P NMR (162 MHz) $\delta_P$ 0.08(s).

EXAMPLE 46

[(2-thiophenesulfonylamino)-methyl]-phosphonic acid mono-(3-chlorophenyl) ester ammonium salt (48)

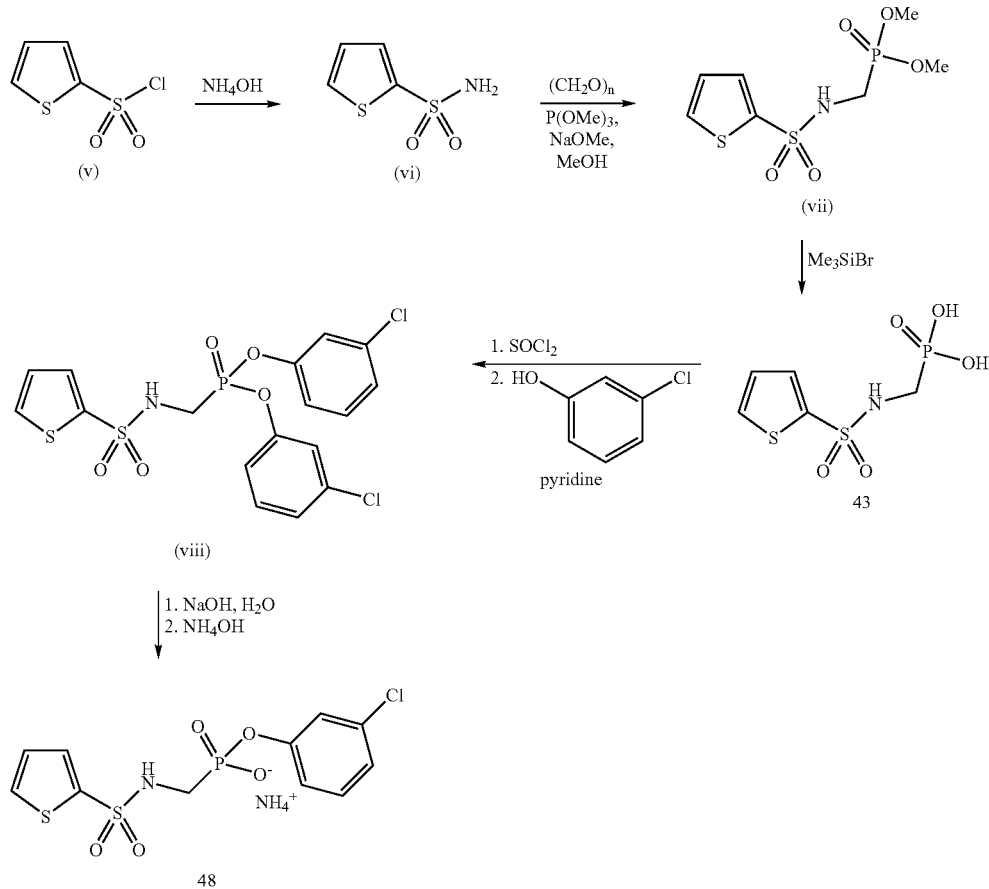

Step 1: 2-Thiophenesulfonamide (vi).

At 0° C., a concentrated solution of ammonium hydroxide (50 mL, 1.35 mol) was added to a solution of 2-thiophenesulfonyl chloride (50 g, 0.27 mol) in methanol (300 mL). The mixture was stirred at room temperature overnight, cooled in an ice bath, and a concentrated solution of HCl was added until the pH reached 7. The resultant solution was extracted with ethyl acetate, and the combined organic layers were dried over anhydrous magnesium sulfate and concentrated to afford 45 g of a brownish solid. Trituration with methylene chloride-hexanes (1:1) afforded the title compound: $^1$H NMR (300 MHz, CD$_3$OD) $\delta_H$ 7.73 (m, 1H), 7.59 (m, 1H), 7.05 (m, 1H).

Step 2: [(2-Thiophenesulfonylamino)methyl]phosohonic acid dimethyl ester (vii).

To a solution of 2-thiophenesulfonamide (vi) (1.0 g, 6.1 mmol) in methanol (5 mL) was added a catalytic amount of sodium methoxide and paraformaldehyde (200 mg, 6.7 mmol). The reaction was heated to 55° C. for 1 h, and then the homogeneous solution was cooled and trimethyl phosphite (0.8 mL, 6.8 mmol) was added. After heating the reaction mixture for an additional 1 h at 55° C., the reaction mixture was cooled and concentrated. The residue was dissolved in dichloromethane (15 mL), washed with water (10 mL), dried (MgSO$_4$), filtered and concentrated. Purification by flash chromatography (elution with methanol-chloroform; 1:19) yielded (vii) (600 mg, 34%) as a colorless solid: $^{31}$P NMR: (162 MHz, CDCl$_3$) $\delta_P$ 23.7. Also isolated was the corresponding N-methylated compound, [(2-thiophenesulfonyl-N-methylamino)methyl]-phosphonic acid dimethyl ester (234 mg, 13%) as a colorless solid: $^{13}$C NMR (100 MHz, CDCl$_3$) $\delta_C$ 36.7, 44.6 (d, J=165 Hz), 53.2 (d, J=6.5 Hz), 127.6, 132.4, 132.6, 135.7.

Step 3: [(2-Thiophenesulfonylamino)methyl]-phosphonic acid (43).

The dimethyl ester (vii) was treated with bromotrimethylsilane according to the procedure described in Example 1, step 3, to afford the title compound: $^1$H NMR (300 MHz, CD$_3$OD) $\delta_H$ 7.79 (dd, J=4.8, 1.2 Hz, 1H), 7.64 (dd, J=3.9, 1.2 Hz, 1H), 7.17 (dd, J=4.8, 3.9 Hz, 1H), 3.16 (d, J=13.2 Hz, 2H).

Step 4: [(2-Thiophenesulfonylamino)methyl]-phosphonic acid di-(3-chlorophenyl) ester (viii).

To a solution of 3-chlorophenol (700 μL, 6.6 mmol) in pyridine (8 mL) at −45° C. was added thionyl chloride (230

μL, 3.2 mmol). The reaction was stirred at −45° C. for 1 h, and then a solution of phosphonic acid (200 mg, 0.78 mmol) in pyridine (5 mL) was slowly added. The reaction mixture was warmed to ambient temperature overnight, and the solution was then concentrated. The residue was dissolved in dichloromethane (15 mL) and washed with water (10 mL). The organic extracts were dried (MgSO$_4$) and concentrated, and the residue was purified by flash chromatography (elution with ethyl acetate-hexanes; 1:1) to yield the diester (viii) (86 mg, 23%) as a colorless solid: $^1$H NMR (400 MHz, CDCl$_3$) δ$_H$ 7.57-7.58 (m, 2H, Ar—H), 7.14-7.26 (m, 6H, Ar—H), 7.04-7.09 (m, 3H, Ar—H), 6.46 (dt, J=2.5, 6.5 Hz, 1H, NH), 3.69 (dd, J=6.5, 12.5 Hz, 2H, NCH$_2$P).

Step 5: [2-Thiophenesulfonylamino)methyl]-phosphonic acid mono-3-chlorophenyl) ester ammonium salt (48).

To a solution of diester (viii) (86 mg, 0.18 mmol) in dioxane (1.5 mL) was added 1 N sodium hydroxide solution (720 μL, 0.72 mmol) and water (4 mL). After 3 h, the solution was neutralized and concentrated the residue was purified by flash chromatography (elution with chloroform:methanol:concentrated ammonium hydroxide; 8.2:2:0.25) to afford the title compound (28 mg, 40%) as a colorless solid: $^1$H NMR (400 MHz, D$_2$O) δ$_H$ 7.84 (d, J=5 Hz, 1H, Ar—H), 7.71 (d, J=3.5 Hz, Ar—H), 7.30 (t, J=8 Hz, 1H, Ar—H), 7.15-7.21 (m, 3H, Ar—H), 7.01-7.03 (m, 1H, Ar—H), 3.23 (d, J=14 Hz, 2H, NCH$_2$P); $^{31}$P NMR: (164 MHz, D$_2$O) δ$_P$ 14.5.

EXAMPLE 47

[(2-Thiophenesulfonylamino)methyl]-phosphonic acid mono-(3-dimethylamino)phenyl) ester ammonium salt (78)

According to the procedure described in Example 1, step 4, the phosphonic acid 43 was treated with 3-dimethylamino) phenol. The ammonium salt was purified by flash chromatography (elution with chloroform:methanol:concentrated ammonium hydroxide; 8:2:0.25), followed by lyophilization, to afford the title compound: $^1$H NMR (300 MHz, D$_2$O) δ$_H$ 7.67 (m, 1H), 7.54 (m, 1H), 7.11 (t, J=7.0 Hz, 1H), 7.04 (m, 1H), 6.68 (d, J=8.4 Hz, 1H), 6.64 (s, 1H), 6.48 (d, J=8.4 Hz, 1H), 3.07, d, J=13.2 Hz, 2H), 2.73 (s, 6H); $^{31}$P NMR: (121 MHz, D$_2$O) δ$_P$ 14.6; $^{13}$C NMR (75 MHz, D$_2$O) δ$_C$ 147.69, 144.91, 132.66, 129.13, 128.76, 125.97, 123.49, 110.35, 108.23, 104.94, 38.00, 34.21, (d, J=150.0 Hz).

EXAMPLE 48

[(2-Thiophenesulfonylamino)methyl]-phosphonic acid mono-(benzyl) ester ammonium salt (79)

According to the procedure described in Example 1, step 4, the phosphonic acid 43 was treated with benzyl alcohol. The ammonium salt was purified by flash chromatography (elution with chloroform:methanol:concentrated ammonium hydroxide; 8:2:0.25), followed by lyophilization, to afford the title compound: $^1$H NMR (300 MHz, D$_2$O) δ$_H$ 7.71 (m, 1H), 7.58 (m, 1H), 7.29 (s, 5H), 7.07 (t, J=7.0 Hz, 1H), 4.75 (d, J=7.8 Hz, 2H), 2.93 (d, J=12.9 Hz, 2H); $^{31}$P NMR: (121 MHz, D$_2$O) δ$_P$ 16.65; $^{13}$C NMR (75 MHz, D$_2$O) δ$_C$ 132.75; 131.10, 129.07, 128.72, 124.12, 123.70, 123.47, 123.13, 62.55, 34.40, (d, J=147.4 Hz).

EXAMPLE 49

[(2-Thiophenesulfonylamino)methyl]-phosphonic acid mono-methyl ester sodium salt (80)

The diester (vii) was treated with sodium hydroxide according to the procedure described in Example 46, step 5, to produce the title compound: $^1$H NMR (300 MHz, CD$_3$OD) δ$_H$ 7.65 (dd, J=4.8, 1.2 Hz, 1H), 7.62 (dd, J=3.6, 1.2 Hz, 1H), 7.15 (dd, J=4.8, 3.6 Hz, 1H), 3.55 (d, J=9.3 Hz, 3H), 3.04 (d, J=13.8 Hz, 2H); $^{31}$P NMR: (121 MHz, CD$_3$OD) δ$_P$ 17.60; $^{13}$C NMR (75 MHz, CD$_3$OD) δ$_C$ 141.77, 132.98, 132.90, 128.43, 52.02, 40.11, (d, J=147.2 Hz).

EXAMPLE 50

[(3-thiophenesulfonylamino)methyl]-phosphonic acid (ix)

Starting with 3-thiophenesulfonyl chloride, procedures analogous to those described in Example 46, steps 1-3, were followed to produce the title compound: $^1$H NMR (300 MHz, CD$_3$OD) δ$_H$ 8.15 (dd, J=3, 1.2 Hz, 1H), 7.66 (dd, J=5.4, 3.0 Hz, 1H), 7.44 (dd, J=5.4, 1.2 Hz, 1H), 3.18 (d, J=13.5 Hz, 2H); $^{13}$C NMR (75.4 MHz, CD$_3$OD) δ$_C$ 140.8, 131.8, 129.4, 126.6, 40.7 (d, J=157 Hz).

EXAMPLE 51

[(3-Thiophenesulfonylamino)methyl]-phosphonic acid mono(3-pyridyl) ester sodium salt (55)

Phosphonic acid compound (ix) was treated with 3-hydroxypyridine according to the procedure described in Example 1, step 4, to provide the title compound: $^1$H NMR (300 MHz, D$_2$O) δ$_H$ 8.15 (br.s, 2H), 8.03 (m, 1H), 7.49 (m, 1H), 7.44 (br d, J=8.7 Hz, 1H), 7.28 (m, 1H), 7.25 (m, 1H), 3.10 (d, J=13.0 Hz, 2H).

EXAMPLE 52

[(3-Thiophenesulfonylamino)methyl]-phosphonic acid mono-(2-chloro-3-pyridyl) ester sodium salt (56)

Phosphonic acid compound (ix) was treated with 2-chloro-3-hydroxypyridine according to the procedure described in Example 1, step 4, to provide the title compound: $^1$H NMR (300 MHz, D$_2$O) δ$_H$ 8.05 (dd, J=3.0, 1.2 Hz, 1H), 7.98 (br d, J=4.8 Hz, 1H), 7.57 (m, 1H), 7.48 (dd, J=5.4, 3.0 Hz, 1H), 7.25 (m, 2H), 3.18 (d, J=12.6 Hz, 2H).

EXAMPLE 53

[(3-Thiophenesulfonylamino)methyl]-phosphonic acid mono-(4-nitrophenyl) ester sodium salt (57)

Phosphonic acid compound (ix) was treated with 4-nitrophenol according to the procedure described in Example 1, step 4, to provide the title compound: $^1$H NMR (300 MHz, D$_2$O) δ$_H$ 8.10 (d, J=9.3 Hz, 2H), 8.04 (m, 1H); 7.50 (dd, J=5.1, 3.0 Hz, 1H), 7.26 (dd, J=5.1, 1.5 Hz, 1H), 7.14 (d, J=9.3 Hz, 2H), 3.11 (d, J=12.9 Hz, 2H).

EXAMPLE 54

[(3-Thiophenesulfonylamino)methyl]-phosphonic acid mono-(2-fluoro-4-nitrophenyl) ester sodium salt (69)

Phosphonic acid compound (ix) was treated with 2-fluoro-4-nitrophenol according to the procedure described in Example 1, step 4, to provide the title compound: $^1$H NMR (300 MHz, D$_2$O) $\delta_H$ 8.05 (m, 1H), 7.99 (m, 1H), 7.93 (m, 1H), 7.49 (m, 1H), 7.27 (m, 2H), 3.18 (d, J=12.6 Hz, 2 H).

EXAMPLE 55

[(3-Furylsulfonylamino)methyl]-phosphonic acid mono-(4-nitrophenyl) ester sodium salt (74)

Step 1: 3-Furylsulfonamide (x)

3-Furylsulfonyl chloride was treated with ammonia according to the procedure described in Example 46, step 1, to produce the title compound.

Step 2: [(3-Furylsulfonylamino)methyl]-phosphonic acid (73)

3-Furylsulfonamide (x) was treated with paraformaldehyde and trimethylphosphite, followed by treatment with bromotrimethylsilane, according to the procedure described in Example 46, steps 2 and 3, to produce the title compound: $^1$H NMR (300 MHz, CD$_3$OD) $\delta_H$ 8.13 (dd, J=1.5, 0.6 Hz, 1H), 7.71 (t, J=1.8 Hz, 1H), 6.78 (dd, J=1.8, 0.6 Hz, 1H), 3.21 (d, J=13.5 Hz, 2H); $^{13}$C NMR (75 MHz, CD$_3$OD) $\delta_C$ 147.2, 146.4, 128.0, 109.3, 40.7 (d, J=158 Hz).

Step 3: [(3-Furylsulfonylamino)methyl]-phosphonic acid mono-(4-nitrophenyl)ester sodium salt (74)

Compound 73 was treated with 4-nitrophenol in the presence of CCl$_3$CN according to the procedure described in Example 1, step 4, to produce the title compound: $^1$H NMR (300 MHz, D$_2$O) $\delta_H$ 8.11 (d, J=9.0 Hz, 2H), 7.80 (m, 1H), 7.51 (m, 1H), 7.16 (d, J=9.0 Hz, 2H), 6.61 (m, 1H), 3.16 (d, J=13.0 Hz, 2H).

EXAMPLE 56

[(3-Furylsulfonylamino)methyl]-phosphonic acid mono-(2-fluoro-4-nitrophenyl) ester sodium salt (75)

Compound 73 was treated with 2-fluoro-4-nitrophenol in the presence of CCl$_3$CN according to the procedure described in Example 1, step 4, to produce the title compound: $^1$H NMR (300 MHz, D$_2$O) $\delta_H$ 8.00 (m, 3H), 7.53 (m, 1H), 7.35 (t, J=8.4 Hz, 1H), 6.63 (m, 1H), 3.21 (d, J=12.9 Hz, 2H).

EXAMPLE 57

[(3-Furylsulfonylamino)methyl]-phosphonic acid mono-(2-chloropyridin-3-yl) ester sodium salt (76)

Compound 73 was treated with 2-chloro-3-hydroxypyridine in the presence of CCl$_3$CN according to the procedure described in Example 1, step 4, to produce the title compound: $^1$H NMR (300 MHz, D$_2$O) $\delta_H$ 8.01 (m, 1H), 7.99 (m, 1H), 7.62 (dt, J=8.1, 1.5 Hz, 1H), 7.51 (t, J=2.0 Hz, 1H), 7.27 (dd, J=8.1, 4.8 Hz, 1H), 6.61 (dd, J=2.0, 0.9 Hz, 1H), 3.20 (d, J=12.6 Hz, 2H).

EXAMPLE 58

[(2-benzothiophenesulfonylamino)methyl]-phosphonic acid mono-(4-nitrophenyl) ester ammonium salt (77)

Step 1: 2-Benzothiophenesulfonamide

Preparation of 2-benzothiophenesulfonamide was effected using the reported procedure (S. L. Graham et al., *J. Med. Chem.* 1989, 32, 2548).

Step 2: [(2-Benzothiophenesulfonylamino)methyl]-phosphonic acid mono-(4-nitrophenyl)ester ammonium salt (77).

2-Benzothiophenesulfonamide was treated with paraformaldehyde and trimethylphosphite, followed by treatment with bromotrimethylsilane, according to the procedure described in Example 46, steps 2 and 3. The crude product was purified by flash chromatography-(elution with dichloromethane:methanol: concentrated ammonium hydroxide; 7:3.5:0.5), followed by lyophilization, to afford the ammonium salt 77: $^1$H NMR (300 MHz, DMSO-d$_6$) $\delta_H$ 7.9 (m, 5H, Ar—H), 7.4 (m, 2H, Ar—H), 7.2 (d, J=9 Hz, 2H, Ar—H), 2.8 (d, J=12.9 Hz, 2H, CH$_2$); $^{31}$P NMR (121 MHz, D$_2$O) $\delta_P$ 12.08 (t, J=12.2 Hz, 1 P).

EXAMPLE 59

[(2-Thiophenesulfonyl-N-methylamino)methyl]-phosphonic acid mono-(4-nitrophenyl) ester ammonium salt (47)

Step 1: [(2-Thiophenesulfonyl-N-methylamino)methyl]-phosphonic acid (xi)

To a solution of [(2-thiophenesulfonyl-N-methylamino)methyl]-phosphonic acid dimethyl ester (obtained as described in Example 46, step 2) (180 mg, 0.6 mmol) in dichloromethane (3 mL) at 0° C. was slowly added bromotrimethylsilane (190 µL, 1.4 mmol). The reaction was gradually warmed to room temperature and allowed to stir overnight. The reaction mixture was concentrated, the residue was redissolved in dichloromethane, and the solution was again concentrated. Methanol (10 mL) was added to the residue, and the solution was stirred at room temperature for 30 min. The solution was then filtered and concentrated. The oily residue was triturated with 1:1 ether-hexanes, and an orange solid was collected by filtration. The orange solid was boiled in dichloromethane (3 mL), cooled, and filtered to yield the title compound (120 mg, 74%) as a colorless solid: $^1$H NMR (400 MHz, CD$_3$OD) $\delta_H$ 7.87 (dd, J=1.5, 4 Hz, 1H, Ar—H), 7.66 (dd, J=1.5, 3.5 Hz, 1H, Ar—H), 7.25 (dd, J=4, 5 Hz, 1H, Ar—H), 3.31 (d, J=12.5 Hz, 2H, CH$_2$P), 2.92 (s, 3H, NCH$_3$).

Step 2: [(2-Thiophenesulfonyl-N-methylamino)methyl]-phosphonic acid mono-(4-nitrophenyl)ester ammonium salt (47)

Compound (xi) was treated with 4-nitrophenol according to the procedure described in Example 1, step 4. The crude product was purified by flash chromatography (elution with chloroform:methanol:concentrated ammonium hydroxide; 8:2:0.25) to afford the ammonium salt 47 (43%) as a colorless solid: $^1$H NMR (400 MHz, CD$_3$OD) $\delta_H$ 8.19-8.23 (m, 2H, Ar—H), 7.85 (dd, J=1, 5 Hz, 1H, Ar—H), 7.62 (dd, J=1, 4 Hz, 1H, Ar—H), 7.44 (dd, J=1, 9.5 Hz, 2H, Ar—H), 7.23 (dd, J=4, 5 Hz, 1H, Ar—H), 3.30 (d, J=13.5 Hz, 2H, NCH$_2$P), 2.93 (s, 3H, NCH₃); ¹³C NMR (100 MHz, CD₃OD) δ$_C$ 37.1, 47.4, 122.4 (d, J=4 Hz), 126.1, 128.9, 133.7 (d, J=7 Hz), 137.1, 144.7, 159.5; ³¹P NMR (162 MHz, CD₃OD) δ$_P$ 12.7; MS (neg. FAB) m/z 391 (M-1, 100%), 306 (15%), 153 (35%).

EXAMPLE 60

[2-Phenyl-1-(thiophene-2-sulfonylamino)-ethyl]-phosphonic acid mono-(4-nitrophenyl) ester ammonium salt. (44)

residue and the solution stirred at room temperature for 30 minutes, then the solution was filtered and concentrated. The oily residue was triturated with 1:1 ether-hexanes and the orange solid collected by filtration. Finally, the orange solid was boiled in dichloromethane (5 mL), cooled and filtered to yield pure phosphonic acid (xiii) (512 mg, 80%) as a colorless solid: ¹H NMR (400 MHz, CD₃OD) δ$_H$ 2.71 (dt, J=14, 10 Hz, 1H, CHPh), 3.13 (ddd, J=4, 8, 14 Hz, 1H, CHPh), 3.89 (ddd, J=4, 10, 14 Hz, NCHP), 6.86 (dd, J=3.5, 5 Hz, 1H, Ar—H), 7.07-7.15 (m, 6H, Ar—H), 7.53 (dd, J=1.5, 5 Hz, 1H, Ar—H).

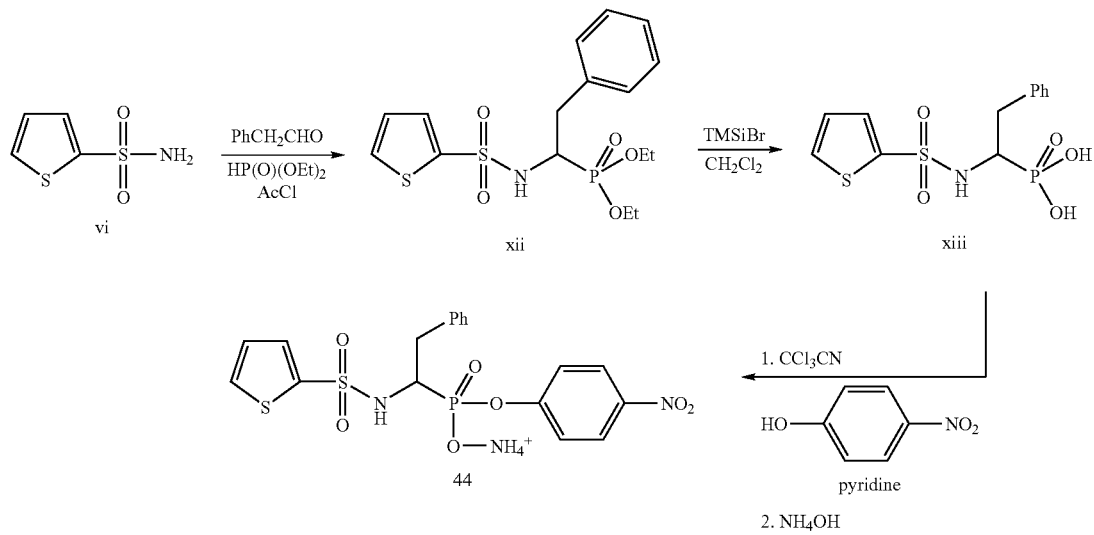

Step 1: [2-Phenyl-1-thiophene-2-sulfonylamino)-ethyl]-phosphonic acid diethyl ester (xii)

To a suspension of sulfonamide (vi) (500 mg; 0.31 mmol) in acetyl chloride (5 mL) was slowly added diethyl phosphite (400 μL; 0.31 mmol). The reaction was cooled to 0° C. and then phenylacetaldehyde (450 μL; 0.39 mmol) was added dropwise. The reaction was gradually warmed to ambient temperature and after 6 hrs the homogeneous solution was concentrated. The residue was diluted with dichloromethane (25 mL) then washed successively with water (10 mL), saturated sodium bicarbonate (10 mL) and brine (10 mL). The combined organic extracts were dried (MgSO₄), evaporated and initially purified by flash chromatography (ethyl acetate-hexanes; 3:2). A second purification by flash chromatography (acetone-hexanes; 3:7) yielded diethyl phosphonate (xii) (437 mg, 35%) as a colorless solid; ¹H NMR (400 MHz, CDCl₃) δ$_H$ 1.22 (t, J=7 Hz, 3H, OCH₂CH₃), 1.26 (t, J=7 Hz, 3H, OCH₂CH₃), 2.89 (dt, J=8, 14 Hz, 1H, CHPh), 3.12 (dt, J=6, 14 Hz, 1H, CHPh), 3.96-4.23 (m, 5H, NCHP and OCH₂CH₃), 6.38 (dd, J=2, 9.5 Hz, 1H, NH), 6.92-6.93 (m, 1H, Ar—H), 7.12-7.20 (m, 5H, Ar—H), 7.33-7.34 (m, 1H, Ar—H), 7.43-7.45 (m, 1 H. Ar—H).

Step 2: [2-Phenyl-1-thiophene-2-sulfonylamino)-ethyl]-phosphonic acid (xiii)

To a solution of diethyl phosphonate (xii) (745 mg; 1.8 mmol) in dichloromethane (8 mL) at 0° C. was slowly added bromotrimethylsilane (2 mL; 15.2 mmol). The reaction was gradually warmed to room temperature and the following day the solution was evaporated. The residue was redissolved in dichloromethane (10 mL), evaporated and the process repeated once more. Methanol (10 mL) was added to the Step 3: [2-Phenyl-1-thiophene-2-sulfonylamino)-ethyl]-phosphonic acid mono-(4-nitrophenyl) ester ammonium salt (44)

To sealed tube containing phosphonic acid (xiii) (50 mg; 0.14 mmol) and sublimed 4-nitrophenol (24 mg; 0.17 mmol) was added pyridine (0.7 mL) and trichloroacetonitrile (100 μL; 1.0 mmol). The reaction was heated to 105° C. for 6 hrs then was cooled and concentrated. The residue was purified by flash chromatography (chloroform-methanol-concentrated ammonium hydroxide; 8:2:0.25) to yield the ammonium salt 44 (36.4 mg, 52%) as a colorless solid: ¹H NMR (400 MHz, CD₃OD) δ$_H$ 2.83 (td, J=9, 14 Hz, 1H, CHPh), 3.23-3.29 (m, 1H, CHPh), 3.95-4.02 (m, 1H, NCHP), 6.85 (dd, J=4, 5 Hz, 1H, Ar—H), 7.08-7.20 (m, 6 H. Ar—H), 7.27-7.31 (m, 2H, Ar—H), 7.52 (dd, J=1.5, 5 Hz, 1H, Ar—H), 8.12-8.16 (m, 2H, Ar—H); ³¹P NMR: (162 MHz, CD₃OD) δ$_P$ 16.7; ¹³C NMR: (100 MHz, CD₃OD) δ$_P$ 38.1, 122.0, 125.9, 127.3, 128.3, 129.2, 130.6, 132.2, 132.3, 144.4, 144.5.

EXAMPLE 61

[2-Methyl-1-thiophene-2-sulfonylamino)-propyl]-phosphonic acid mono-(4-nitrophenyl) ester ammonium salt (52)

The title compound was synthesized according to the three-step procedure described in Example 60, Steps 1-3, but substituting isobutyraldehyde for phenylacetaldehyde. The mono ester 52 was isolated as a colorless solid (13% yield over three steps): ¹H NMR: (400 MHz, DMSO-D₆) δ$_H$ 0.86 (d, J=7 Hz, 3H, CH₃), 0.93 (d, J=7 Hz, 3H, CH₃), 2.02-2.10

(m, 1H, (CH$_3$)$_2$CH), 3.28-3.35 (m, 1H, NCHP), 7.03 (dd, J=3.5, 5 Hz, 1H, Ar—H), 7.12 (br s, 5H, NH), 7.17 (dd, J=9 Hz, 2H, Ar—H), 7.60 (dd, J=1, 3.5 Hz, 1H, Ar—H), 7.75 (dd, J=1, 5 Hz, 1H, Ar—H), 8.06-8.10 (m, 2H, Ar—H); $^{31}$P NMR: (162 MHz, DMSO-D$_6$) δ$_P$ 14.2; $^{13}$C NMR: (100 MHz, DMSO-D$_6$) δ$_C$ 19.8, 21.3, (d, J=10), 30.7, 58.3 (d, J=142.3), 121.3 (d, J=4.5), 125.9, 128.2, 132.2, 132.4, 142.2, 144.7, 161.2.

EXAMPLE 62

[Phenyl-(thiophene-2-sulfonylamino)-methyl]-phosphonic acid mono-(4-nitrophenyl) ester ammonium salt (53)

The title compound was synthesized according to the three-step procedure in Example 60, Steps 1-3, but substituting benzaldehyde for phenylacetaldehyde. The mono ester 53 was isolated as a colorless solid (8% yield over three steps): $^1$H NMR (400 MHz, DMSO-D$_6$) δ$_H$ 4.44 (d, J=22 Hz, 1H, NCHP), 6.83 (dd, J=4, 5 Hz, 1H, Ar—H), 7.00-7.07 (m, 4H), 7.17-7.33 (m, 9H), 7.60 (dd, J=1.5, 5 Hz, 1H, Ar—H), 8.08-8.12 (m, 2H, Ar—H); $^{31}$P NMR: (162 MHz, DMSO-D$_6$) δ$_P$ 10.1; $^{13}$C NMR: (100 MHz, DMSO-D$_6$) δ$_C$ 58.0 (d, J=140.2 Hz) 121.6 (d, J=4 Hz), 125.9, 126.9, 127.9, 128.1, 129.1 (d, J=5 Hz), 132.3, 132.6, 138.9, 142.4, 143.6 and 161.4.

EXAMPLE 63

[2-Phenyl-1-(thiophene-2-sulfonylamino)-ethyl]-phosphonic acid mono-(2-chloropyridin-3-yl)ester ammonium salt (46)

To a sealed tube containing phosphonic acid (xiii) (134 mg; 0.39 mmol) and 2-chloro-3-pyridinol (60 mg; 0.46 mmol) was added pyridine (1.9 mL) and trichloroacetonitrile (270 µL; 2.7 mmol). The reaction was heated to 105° C. for 6 hours then was cooled and concentrated. The residue was purified by flash chromatography (chloroform-methanol-concentrated ammonium hydroxide; 9:2:0.1) to yield the ammonium salt 46 (100 mg, 54%) as a colorless solid: $^1$H NMR: (400 MHz, CD$_3$OD) δ$_H$ 2.87 (td, J=9, 14 Hz, 1H, CHPh), 3.28-3.36 (m, 1H; CHPh), 4.01 (ddd, J=4.5, 9, 17 Hz, 1H, NCHP), 6.81 (dd, J=3.5, 5 Hz, 1H, Ar—H), 7.07-7.21 (m, 6H. Ar—H), 7.28 (dd, J=4.5, 8 Hz, 1H, Ar—H), 7.46 (dd, J=1.5, 5 Hz, 1H, Ar—H), 7.91-7.93 (m, 1H, Ar—H), 7.99-8.02 (m, 1H, Ar—H); $^{31}$P NMR: (162 MHz, CD$_3$OD) δ$_P$ 17.0; $^{13}$C NMR: (100 MHz, DMSO-D$_6$) δ$_C$ 38.3, 55.6, (d, J=147.6 Hz), 124.3, 126.7, 128.1, 130.1, 130.4, 131.8, 132.1, 140.3 (d, J=10 Hz), 142.4, 142.7, 144.5, 147.9.

EXAMPLE 64

[2-Methyl-1-(thiophene-2-sulfonylamino)-propyl]-phosphonic acid mono-(2-chloropyridin-3-yl)ester ammonium salt (54)

Following the same procedure as described in Example 63, but substituting the phosphonic acid derived from Example 61 for phosphonic acid (xiii), the title compound was obtained. The mono ester 54 was isolated as a colorless solid (37% yield): $^1$H NMR (400 MHz, CD$_3$OD) δ$_H$ 1.02 (d, J=7 Hz, 3H, CH$_3$), 1.06 (d, J=7 Hz, 3H, CH$_3$), 2.24-2.32 (m, 1H, (CH$_3$)$_2$CH), 3.69 (dd, J=3.5, 19.5 Hz, 1H, NCHP), 6.91 (dd, J=4, 5 Hz, 1H, Ar—H), 7.25 (dd, J=5, 8 Hz, 1 H, Ar—H), 7.52-7.59 (m, 2H, Ar—H), 7.80-7.82 (m, 1H, Ar—H), 7.99-8.01 (m, 1H, Ar—H); $^{31}$P NMR: (162 MHz, CD$_3$OD) δ$_P$ 17.3; $^{13}$C NMR: (100 MHz, DMSO-d$_6$) δ$_C$ 18.8, 21.1 (d, J=11.5), 31.1 (d, J=5), 59.0 (d, J=149.5), 124.5, 128.0, 131.2, 132.2, 132.8, 143.6, 144.5, 156.2, 156.4.

EXAMPLE 65

[Phenyl-(thiophene-2-sulfonylamino)-methyl]-phosphonic acid mono-(2-chloropyridin-3-yl)ester ammonium salt (60)

Following the same procedure as described in Example 63, but substituting the phosphonic acid derived from Example 62 for phosphonic acid (xiii), the title compound was obtained. The mono ester 60 was isolated as a colorless solid (50% yield): $^1$H NMR (400 MHz, DMSO-d$_6$) δ$_H$ 4.49 (d, J=22 Hz, 1H, NCHP), 6.80 (dd, J=4, 5 Hz, 1H, Ar—H), 6.99-7.07 (m, 3H, Ar—H), 7.20-7.33 (m, 9H), 7.58 (dd, J=1.5, 5 Hz, 1H, Ar—H), 7.84 (dd, J=1.5, 8 Hz, 1H, Ar—H), 7.94 (dd, J=1.5, 5 Hz 1H, Ar—H); $^{31}$P NMR: (162 MHz, DMSO-D$_6$) δ$_P$ 10.7; $^{13}$C NMR: (100 MHz, DMSO-d$_6$) δ$_C$ 58.3 (d, J=140.5), 124.3, 127.0, 127.9, 128.1, 129.1 (d, J=5), 129.9, 132.3, 132.6, 138.8, 142.5, 142.9, 143.5, 148.0.

EXAMPLE 66

[(2-Benzothiophenesulfonyl-N-methylamino)-methyl]-phosphonic acid mono-(4-nitrophenyl) ester ammonium salt. (142)

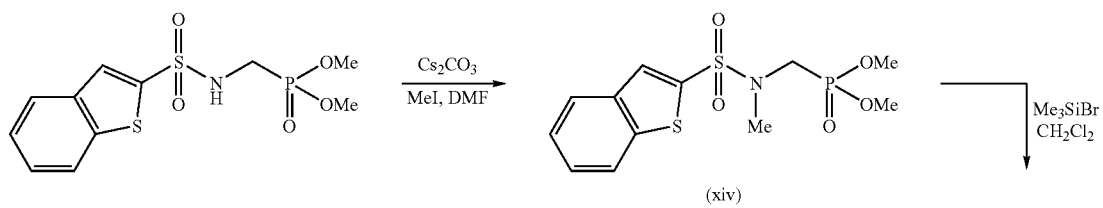

(xiv)

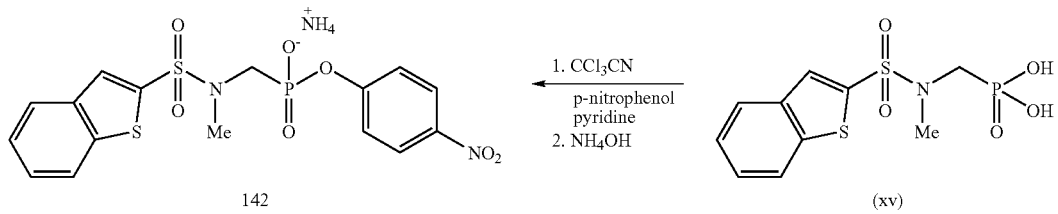

Step 1: [(2-Benzothiophenesulfonyl-N-methylamino)-N-methyl]-phosphonic acid dimethyl ester (xiv)

A reaction mixture consisting of 290 mg (0.83 mmol) of [(2-benzothiophenesulfonylamino)-methyl]-phosphonic acid dimethyl ester, 380 mg (1.16 mmol) of anhydrous cesium carbonate, 0.11 mL (1.16 mmol) of methyl iodide and 5 mL of anhydrous DMF stirred for 16 hours at room temperature. After the reaction was complete, DMF was evaporated in vacuum, and the residue was suspended in 15 mL of water and extracted with dichloromethane. The extract was dried over anhydrous magnesium sulfate, filtered and evaporated, providing an oily residue which was chromatographed on a silica gel column, eluent EtOAc/hexane (7:3), then dichloromethane/MeOH (20:1), to yield the title compound as a yellowish oil (190 mg, 63%): $^1$H NMR: (300 MHz, CDCl$_3$) $\delta_H$ 3.00 (s, CH$_3$), 3.48 (d, J=11.5 Hz, 2H), 3.83 (d, J=10.9 Hz, 6H, 2CH$_3$), 7.45-7.50 (m, 2H, Ar—H), 7.83-7.89 (m, 3H, Ar—H).

Step 2: [(2-Benzothiophenesulfonyl-N-methylamino)-methyl]-phosphonic acid (xv)

To a solution of 550 mg (1.58 mmol) of the compound (xiv) in 10 mL of anhydrous dichloromethane at 0° C., 0.49 mL of bromotrimethylsilane was added. The mixture was warmed up to room temperature and left overnight. Dichloromethane was evaporated; the oily residue was dissolved in another 10 mL of dichloromethane, filtered, again evaporated and redissolved in 10 mL of MeOH. The methanolic solution stirred at room temperature 30 min., evaporated and the residue was triturated with a mixture ether/hexane to form a white crystalline product which was separated by filtration (390 mg, 70%): $^1$H NMR: (300 MHz, DMSO-D$_6$) $\delta_H$ 2.88 (s, CH$_3$), 3.21 (d, J=12.1 Hz, 2H), 7.49-7.61 (m, 2H, Ar—H), 8.01-8.17 (m, 3H, Ar—H).

Step 3: [(2-Benzothiophenesulfonyl-N-methylamino)-methyl]-phosphonic acid mono-(4-nitrophenyl) ester ammonium salt (142)

A reaction mixture consisting of 500 mg (1.56 mmol) of (xv), 265 mg (1.90 mmol) of p-nitrophenol, 1.1 mL (11 mmol) of trichloroacetonitrile, and 5 mL of anhydrous pyridine was stirred in a sealed tube for 5 hours at 105-110° C. After the reaction was complete, pyridine was evaporated in vacuum, the oily residue was chromatographed on a silica gel column, eluent chloroform/MeOH/ammonium hydroxide (9:2:0.1) to yield 620 mg (87%) of the title compound as a pale crystalline substance: $^1$H NMR: (300 MHz, DMSO-d$_6$) $\delta_H$ 2.89 (s, CH$_3$), 3.07 (d, J=11.5 Hz, 2 H), 7.15 (br s, 4H, NH$_4$), 7.37 (d, J=9.3 Hz, 2H, Ar—H), 7.47-7.57 (m, 2H, Ar—H), 8.01-8.14 (m, 5 H, Ar—H).

EXAMPLE 67

[(2-Benzothiophenesulfonyl-N-ethylamino)-methyl]-phosphonic acid mono-(4-nitrophenyl) ester ammonium salt (144)

The title compound was prepared in 62% yield following the procedure from Example 66, steps 1-3, but using ethyl iodide as the alkylating agent: $^1$H NMR: (300 MHz, DMSO-d$_6$) $\delta_H$ 1.00 (t, J=7.0 Hz, CH$_3$), 3.33 (d, J=11.1 Hz, PCH$_2$), 3.49 (q, J=7.1 Hz), 6.95-7.51 (m, 8H, Ar—H, NH$_4$), 7.98-8.10 (m, 5H, Ar—H).

EXAMPLE 68

[(2-Benzothiophenesulfonyl-N-benzylamino)-methyl]-phosphonic acid mono-(4-nitrophenyl) ester ammonium salt (145)

The title compound was prepared in 58% yield following the procedure from Example 66, steps 1-3 but using benzyl bromide as the alkylating agent: $^1$H NMR: (300 MHz, DMSO-d$_6$) $\delta_H$ 3.29 (d, J=10.0 Hz, PCH$_2$), 4.78 (s, CH$_2$Ph), 7.16-7.47 (m, 13H, Ar—H, NH$_4$), 7.96-8.00 (m, 4H, Ar—H), 8.07 (s, 1H, Ar—H)

EXAMPLE 69

[(2-Benzothiophenesulfonyl-N-phenylethylamino)-methyl]-phosphonic acid mono-(4-nitrophenyl)ester ammonium salt (143)

The title compound was prepared in 55% following the procedure from Example 66, steps 1-3, but using 2-bromoethyl benzene as the alkylating agent: $^1$H NMR: (300 MHz, DMSO-d$_6$) $\delta_H$ 2.86 (dd, J=8.4, Hz, NCH$_2$), 3.43 (d, J=11.2 Hz, PCH$_2$), 3.58 (dd, J=8.5 Hz, CH$_2$Ph), 7.13-7.56 (m, 13H, Ar—H, NH$_4$), 7.96-8.10 (m, 5H, Ar—H).

EXAMPLE 70

(5,8-dichlorobenzothiophene-2-sulfonyl)aminomethylphosphonic acid mono-(4-nitrophenyl) ester ammonium salt (128)

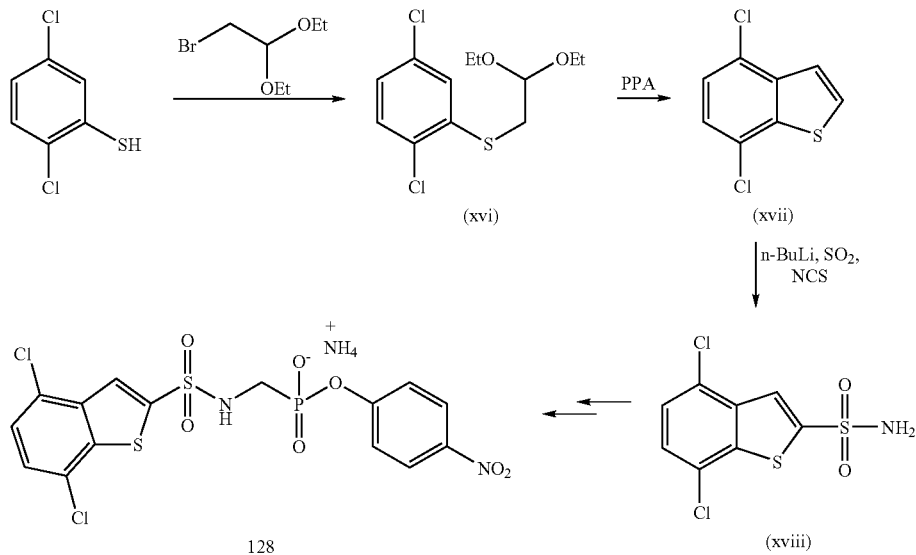

Step 1: 2,2-Diethoxyethyl 2,5-dichlorophenyl sulfide (xvi)

Under a nitrogen atmosphere, to 2,5-dichlorobenzenethiol (25 g, 139 mmol) in 140 mL of acetone in a 250 mL round-bottomed flask was added 21 g (154 mmol) of potassium carbonate, followed by 22 mL (146 mmol) of diethyl acetal. The mixture was stirred overnight at room temperature and then filtered, washing the collected solid with acetone, and the filtrate was concentrated. Water was added to the concentrated filtrate, and the aqueous phase was extracted three times with ethyl acetate. The combined organic layers were washed with 0.5 M KOH, water and brine, dried over magnesium sulfate, filtered, and concentrated. The title compound was obtained as a yellow oil (37 g, 90%): $^1$H NMR (300 MHz, CDCl$_3$) $\delta_H$ 7.36 (d, j=2.1 Hz, 1H), 7.26 (d, J=8.4 Hz, 1H), 7.06 (dd, J=2.1, 8.4 Hz, 1H), 4.71 (t, J=5.4 Hz, 1H), 3.71 (quintuplet, J=7.2 Hz, 2H), 3.57 (quintuplet, J=6.9 Hz, 2H), 3.14 (d, J=5.4 Hz, 2H), 1.22 (t, J=7.2 Hz, 6H).

Step 2: 5,8-Dichlorobenzothiophene (xvii)

Anhydrous chlorobenzene (250 mL) was placed in a 500-mL three-necked flask equipped with a condenser, an addition funnel, and a magnetic stirring bar. The apparatus was flushed with nitrogen, and polyphosphoric acid (40 g) was added. The mixture was heated at 125° C., and 2,2-diethoxyethyl 2,5-dichlorophenyl sulfide (24 g, 82 mmol) in 25 mL of chlorobenzene was added over one hour. The resultant mixture was allowed to sir overnight. The reaction mixture was cooled to room temperature, and the organic phase was separated from polyphosphoric acid. Residual polyphosphoric acid was decomposed with water, and the resultant aqueous phase was washed twice with chloroform. The combined organic phases were dried over magnesium sulfate and concentrated. The crude product was purified by flash chromatography, eluting with a mixture of 5% ethyl acetate: 95% hexane to give 1.5 g (99%) of 5,8-dichlorobenzothiophene as a light yellow solid:

$^1$H NMR (300 MHz, CDCl$_3$) $\delta_H$ 7.57 (d, J=5.4 Hz, 1H), 7.53 (d, J=5.4 Hz, 1H), 7.32 (d, J=8.1 Hz, 1H), 7.27 (d, J=8.1 Hz, 1H).

Step 3: 5,8-Dichlorobenzothiophene-2-sulfonamide (xviii)

Under a nitrogen atmosphere, to 5,8-dichlorobenzothiophene (6.58 g, 32 mmol) in 50 mL of THF at −78° C. in a 250-mL round-bottomed flask was slowly added a 2.5 M solution of n-butyllithium in pentane (16 mL, 40 mmol). After 30 minutes, sulfur dioxide gas was bubbled over the solution until the mixture became acidic. Hexane was added, and the mixture was warmed to room temperature. The sulfinic salt was collected by filtration and dried overnight under high vacuum.

Under a nitrogen atmosphere, to the sulfinic salt (8.88 g, 32 mmol) in 60 mL of dichloromethane at 0° C. in a 250-mL round-bottomed flask was added N-chloro-succinimide (6.29 g, 47 mmol). After 15 minutes, the mixture was warmed to room temperature over 45 minutes. The suspension was filtered over Celite, and the filtrate was concentrated to give 9.65 g (100%) of the corresponding sulfonyl chloride. This material was dissolved in 50 mL of acetone and cooled to 0° C., and 10 mL of ammonium hydroxide was added. After 15 minutes, the mixture was warmed to room temperature over 45 minutes, and the solvents were evaporated. The residue was dissolved in water and extracted three times with ethyl acetate. The combined organic layers were washed with brine, dried over magnesium sulfate, and concentrated. The title compound was obtained as a white solid (6.45 g, 70%): $^1$H NMR (300 MHz, CDCl$_3$) $\delta_H$ 8.09 (s, 1H), 7.41 (s, 2H)

Step 4: (5,8-dichlorobenzothiophene-2-sulfonyl)aminomethylphosphonic acid mono-(4-nitrophenyl) ester ammonium salt (128)

Compound 128 was prepared by procedures analogous to those described in Example 46, steps 2 and 3, and Example 1, step 4: $^1$H NMR (300 MHz, DMSO-d$_6$) $\delta_H$ 7.94 (s, 1H), 7.92 (d, J=9.3 Hz, 2H), 7.57-7.65 (m, 2H), 7.21-7.38 (m, 4H), 7.22 (d, J=9.3 Hz, 2H), 2.96 (d, J=12.9 Hz, 2H).

EXAMPLE 71

Determination of IC$_{50}$

Enzyme activity against the commercially available substrate, nitrocefin, was measured in the presence of various inhibitor concentrations. The P99 β-lactamase enzyme (1 mg/mL) was dissolved in 20 mM MOPS buffer at pH 7.50, and diluted 200-fold in the same buffer containing 0.1% BSA. Nitrocefin was stored as a 100 μM stock solution in 20 mM MOPS at pH 7.5. Stock solutions of test compounds were prepared in 10 mM MOPS at pH 7.5 (approximately 1 mg/mL)

A typical assay contained 300 μL of 100 μM nitrocefin, x μL of inhibitor test compound, 110-x μL of MOPS, and 10 μL of P99 β-lactamase. The reaction at 25° C. was followed spectrophotometrically at 482 nm. IC$_{50}$ values were determined from the dose-response plots of the initial rates vs. inhibitor concentration TEM R+ and L-1 β-lactamases were assayed as described above for P99 β-lactamase.

Representative results using the test inhibitors of the invention showing the inhibition of β-lactamases are shown in Tables 1, 2, 4, and 5.

EXAMPLE 72

Determination of Antibiotic Minimum Inhibitory Concentration (MIC) in the Presence and Absence of β-Lactamase Inhibitor Principle An increasing number of organisms produce enzymes that inhibit the actions of β-lactam antibiotics, so-called, β-lactamases. The "strength" of β-lactam antibiotics can be improved by pairing them with compounds that inhibit bacterial enzyme β-lactamases. The Minimum Inhibitory Concentration (MIC) test determines the lowest concentration of an antibiotic at which no visible bacterial growth occurs. This test permits comparisons to be made between bacterial growth in the presence of antibiotic alone (control) and bacterial growth in the presence of both an antibiotic and a novel (test) compound.

Materials Required
  β-lactamase positive strains
  β-lactam antibiotics
  β-lactamase inhibitor compounds
  appropriate bacterial growth medium β-Lactamase Positive strains
  *Klebsiella oxytoca* [ATCC#51983]
  *Staphylococcus aureus* [MGH: MA#50848]
  *Enterococcus faecalis* [ATCC#49757]
  *Enterobacter cloacae* [ATCC#23355]
  *Haemophilus influenzae* [ATCC#43163]

β-Lactam Antibiotics

| Piperacillin | 333 mg/mL |
| TAZOCIN ™ (piperacillin + tazobactam) | 308 mg/mL |
| Ticarcillin | 500 mg/mL |
| TIMENTIN ™ (ticarcillin + clavulanic acid) | 500 mg/mL |
| Cefoxitin | 333 mg/mL |
| Ceftriaxone | 250 mg/mL |
| Preparation: | Dissolved in MHB (Mueller Hinth Broth) |
| Working dilutions: | 0.06 mg/mL to 4.22 mg/mL |

β-Lactamase Inhibitor Compounds (Test Compounds)

| Preparation: | Dissolved in MHB or DMSO |
| Stock solution: | 2 mg/mL |
| Working concentration: | 1, 10, 100 μg/mL |

Culture Media

| MHB: | Mueller Hinth Broth |
| HTM: | *Haemophilus* Test Medium Broth |
| origin: | Becton Dickinson |
| storage: | 4° C. |
| Blood agar (prepared general culture plate) | |
| Chocolate agar (prepared plate + accessory factors, required by *H inflenzae*) | |
| origin: | Oxoid |
| storage: | 4° C. |

Assay Procedure

Frozen bacterial stocks were thawed to room temperature, and a few drops were placed on an appropriate plate; chocolate agar was used for *H. influenzae*, blood agar was used for all others. The plates were incubated overnight at 37° C. in air, except for *H. influenzae*, which was incubated in a CO$_2$ incubator. The cultures were subcultured the following day, and the subcultures were again incubated overnight A sterile loop was touched to 3 colonies and used to inoculate 1 mL of Mueller-Hinton Broth (MHB). The bacterial solution was diluted 18.8-fold (20 μL of bacterial solution in 355 μL of broth). 5 μL of the resultant inoculum solution contained ~4×10$^4$ CFU/mL. Confirmation of the inoculum was performed by preparing a serial dilution to give 100 μL of a 5000-fold dilution, all of which was then plated onto an appropriate plate. After incubation overnight at 37° C., the plate had 75-150 colonies.

In each well of a 96-well microtiter plate was combined 5 μL of bacterial inoculum, 90 μL of antibiotic dilutions, and 5 μL of test compound (or media for determination of the MIC of the antibiotic in the absence of test compound). Each plate included 2 wells with no bacterial inoculum (negative control) and 2 wells with no test compound and no antibiotic (positive control). The plate was covered and incubated with gentle shaking for 16-20 hours at 37° C. in air (CO$_2$ for *H. influenzae*). Absorbance was read at 540 nm (Multiskan Titertek mcc/340). Bacterial growth was scored as follows:

| | |
|---|---|
| invisible to the naked eye (OD <0.05) | NEGATIVE |
| barely visible (OD >0.05, but <50% of positive control | PLUS/MINUS |
| readily visible (typically OD >0.10) | PLUS |
| abundant growth (OD >0.3) | PLUS-PLUS |

The minimum inhibitory concentration (MIC), defined to be the lowest dilution of antibiotic that completely inhibits growth, was determined for the antibiotic alone and for antibiotic in the presence of each test compound. In some cases, the determination of MIC in the presence of test compound was performed at more than one concentration of the test compound.

Representative data is presented in Tables 1 and 2. The impact of the novel β-lactamase inhibitors is expressed as the ratio of the MIC determined in the absence of β-lactamase inhibitor to the MIC determined in the presence of the specified concentration of the lactamase inhibitor test compound. A value of 1 indicates that the β-lactamase inhibitor had no effect on antibiotic potency, while a positive integer indicates that the β-lactamase inhibitor produces a synergistic effect when co-administered with an antibiotic agent, that is, a higher concentration of antibiotic is required to completely inhibit visible bacterial growth in the absence of the test compound than in its presence

EXAMPLE 73

Synergistic Effect of β-Lactamase Inhibitors When Tested Against Highly Resistant β-Lactamase Positive Bacterial Strains Following procedures identical to those described in Example 72, β-lactamase inhibitors were tested for their ability to enhance antibiotic efficacy against β-lactamase positive bacterial strains that are very highly resistant to β-lactam antibiotics. Representative results are presented in Table 3.

Highly Resistant β-Lactamase Positive Strains
*Enterobacter cloacae* (derepressed)
*Pseudomonas aeroginosa* [ATCC#12470-resistant]
*Stenotrophomonas maltophilia* [ATCC#12968-resistant]
*Pseudomonas aeroginosa* [ATCC#98043010-intermediate resistance]
*Stenotrophomonas maltopilia* [ATCC#980430294-intermediate resistance]

Successful inhibition of bacterial βlactamase activity in these assays is expected to be predictive of success in animals and humans. For examples of the successful clinical development of β-lactamase inhibitors identified by in vitro testing, see, e.g., Di Modugno et al., Current Opinion in Anti-Infective Investigational Drugs 1:26-39 (1999); Moellering, J. Antimicrobial Chemotherapy 31 Suppl. A:1-8 (1993).

TABLE 1

β-Lactamase Inhibition and Microbiological Efficacy of Sulfonamidomethylphosphonate Derivatives.

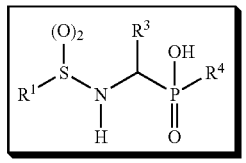

| | | | | | | | Synergy[2] (at μg/mL) | | |
|---|---|---|---|---|---|---|---|---|---|
| | | | | | | IC$_{50}$ | Class C | Class A | |
| Cpd. | R[1] | R[3] | R[4] | | | (μM) Log P | E. Cl[3] "C"[1] 10/1[4] | H. In. 10/1[5] | St. A. 10 |
| 1 | benzyl (C$_6$H$_5$-CH$_2$-) | H | PNP[6] | | | 162 | 1/1 | (1) | (1) |
| 2 | 4-F-C$_6$H$_4$- | H | PNP | | | 16 | | 24 | 2 |
| 3 | 4-Cl-C$_6$H$_4$- | H | PNP | | | 5 | 2/1 | (1) | (1) |
| 4 | 2-naphthyl | H | PNP | | | 2 | 2/1 | (1) | (1) |

TABLE 1-continued
β-Lactamase Inhibition and Microbiological Efficacy of Sulfonamidomethylphosphonate Derivatives.
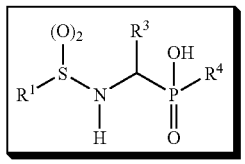
| | | | | | | Synergy[2] (at μg/mL) | | |
| | | | | | | | Class C | Class A | |
| Cpd. | R[1] | R[3] | R[4] | Log P | IC$_{50}$ (μM) "C"[1] | E. Cl[3] 10/1[4] | H. In. 10/1[5] | St. A. 10 |
|---|---|---|---|---|---|---|---|---|
| 5 | MeO-C$_6$H$_4$- | H | PNP | | 4 | 2/1 | (1) | (1) |
| 6 | H$_3$C-C$_6$H$_4$- | H | PNP | | 7 | 2/1 | (1) | (1) |
| 7 | C$_6$H$_5$- | H | PNP | | 4 | 4/2 | (16) | (2) |
| 8 | F-C$_6$H$_4$- | H | 3-pyridyloxy | | >100 | 2/1 | 1 | (1) |
| 9 | 3,4-Cl$_2$-C$_6$H$_3$- | H | PNP | | 5 | 4/2 | 32 | 2 |
| 10 | 1-naphthyl | H | PNP | | 6 | 2/1 | 16 | 4 |
| 11 | F-C$_6$H$_4$- | H | 8-quinolyloxy | | >100 | 1/1 | 8 | 1 |
| 12 | O$_2$N-C$_6$H$_4$- | H | PNP | | 10 | 1/1 | 8 | 1 |
| 13 | 2-NO$_2$-C$_6$H$_4$- | H | PNP | | 6 | 4/1 | 8 | 1 |

TABLE 1-continued

β-Lactamase Inhibition and Microbiological Efficacy of Sulfonamidomethylphosphonate Derivatives.

[Structure: R¹-S(O)₂-N(H)-C(R³)(H)-P(=O)(OH)(R⁴)]

| Cpd. | R¹ | R³ | R⁴ | Log P | IC₅₀ (μM) "C"¹ | Synergy² (at μg/mL) Class C E. Cl³ 10/1⁴ | Class A H. In. 10/1⁵ | St. A. 10 |
|---|---|---|---|---|---|---|---|---|
| 14 | 2,5-dichlorophenyl | H | PNP | | 3 | 4/2 | (8) | (2) |
| 15 | 2-thienyl | H | PNP | | 18 | 3/1 | 4 | 1 |
| 16 | 4-tert-butylphenyl | H | PNP | | 19 | 1/1 | 8 | 1 |
| 17 | 4-(CF₃)phenyl | H | PNP | | 9 | 2/1 | 8 | 2 |
| 18 | 2,4-dinitrophenyl | H | PNP | | 4 | 4/1 | 8 | 1 |
| 19 | 8-quinolinyl | H | PNP | | 43 | 4/4 | (4) | (1) |
| 20 | 4-methylphenyl | H | F | | | 8/8 | (16) | (1) |
| 21 | 2,4,5-trimethylphenyl | H | PNP | | 4 | 2/1 | (2) | (1) |
| 22 | 4-chloro-3-nitrophenyl | H | PNP | | 7 | 2/1 | 16 | 4 |

TABLE 1-continued
β-Lactamase Inhibition and Microbiological Efficacy of Sulfonamidomethylphosphonate Derivatives.
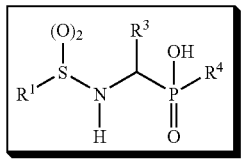
| | | | | | | Synergy[2] (at μg/mL) | | |
| | | | | | | | Class C | Class A |
| Cpd. | R[1] | R[3] | R[4] | Log P | IC$_{50}$ (μM) "C"[1] | E. Cl[3] 10/1[4] | H. In. 10/1[5] | St. A. 10 |
|---|---|---|---|---|---|---|---|---|
| 23 | 2-Br-phenyl | H | PNP | | 14 | 1/1 | 2 | 1 |
| 24 | 3-pyridyl | H | PNP | | 119 | 4/1 | 8 | 1 |
| 25 | 3-pyridyl | H | O-3-pyridyl | | 1,200 | 10/2 | 1 | 2 |
| 26 | 2-thienyl | H | O-pentafluorophenyl | | 1,200 | 16/2 | 1 | 1 |
| 27 | dibenzofuranyl | H | PNP | | 5.0 | 1/1 | 4 | 2 |
| 28 | 2-thienyl | H | O-2,4,6-trifluorophenyl | | 1,800 | | | |
| 29 | 2-thienyl | H | F | | 972 | | | |
| 30 | 4-F-phenyl | H | O-(2-Cl-3-pyridyl) | | 622 | 8/2 | 1 | 1 |

TABLE 1-continued

β-Lactamase Inhibition and Microbiological Efficacy of Sulfonamidomethylphosphonate Derivatives.

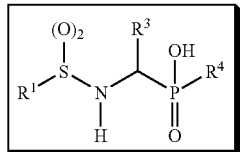

| | | | | | | Synergy[2] (at µg/mL) | | |
| | | | | | | | Class C | Class A |
| Cpd. | R[1] | R[3] | R[4] | Log P | IC$_{50}$ (µM) "C"[1] | E. Cl[3] 10/1[4] | H. In. 10/1[5] | St. A. 10 |
|---|---|---|---|---|---|---|---|---|
| 31 | 2-pyridyl | H | PNP | | 136 | 8/2 | 2 | 1 |
| 32 | 2-pyridyl | H | 2-chloro-3-pyridyloxy | | 639 | 16/2 | 1 | 1 |
| 33 | 5-isoquinolinyl | H | PNP | | 5 | 8/4 | 4 | 4 |
| 34 | 2-pyridyl | H | OH | | 1600 | 2/2 | 1 | 1 |
| 35 | 4-F-phenyl | H | OCH$_3$ diester | | — | 1/1 | 1 | 1 |
| 36 | 5-isoquinolinyl | H | 2-chloro-3-pyridyloxy | | 410 | 2/2 | 1 | 1 |
| 37 | 4-F-phenyl | H | 2-bromo-3-pyridyloxy | | 2000 | 4/2 | 1 | 1 |
| 38 | 2-thienyl | H | 2-chloro-3-pyridyloxy | | 362 | 8/4 | 1 | 1 |
| 39 | 4-biphenyl | H | PNP | | 7 | 1/1 | 8 | 4 |

TABLE 1-continued
β-Lactamase Inhibition and Microbiological Efficacy of Sulfonamidomethylphosphonate Derivatives.
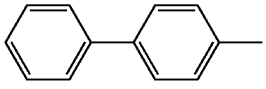
| Cpd. | R[1] | R[3] | R[4] | Log P | IC$_{50}$ (μM) "C"[1] | Synergy[2] (at μg/mL) Class C E. Cl[3] 10/1[4] | H. In. 10/1[5] | Class A St. A. 10 |
|---|---|---|---|---|---|---|---|---|
| 40 | 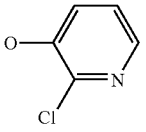 | H | 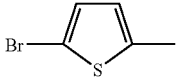 | | 356 | 2/1 | 4 | 2 |
| 41 | 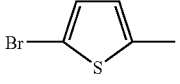 | H | PNP | | 5 | 2/1 | 8 | 4 |
| 42 | 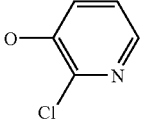 | H | 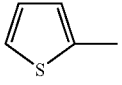 | | 59 | 8/1 | 2 | 1 |
| 43 | 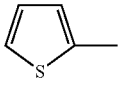 | H | OH | | | | | |
| 44 | 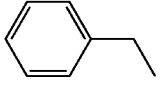 | 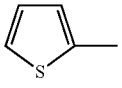 | PNP | | 192 | 2/2 | 1 | 1 |
| 45 | 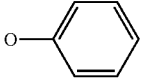 | H | 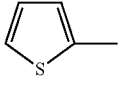 | | 3500 | 2/1 | 1 | 1 |
| 46 | 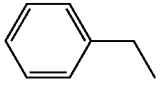 | 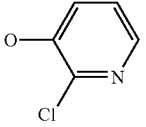 | 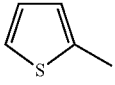 | | 188 | 1/1 | 1 | 1 |
| 47 | 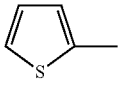 | H<br>N—Me | PNP | | 276 | 2 | 1 | |
| 48 | 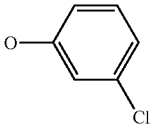 | H | 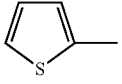 | | 189 | 4/2 | 1 | 1 |
| 49 | 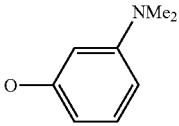 | H | | | 3000 | 1/1 | 1 | 1 |

TABLE 1-continued

β-Lactamase Inhibition and Microbiological Efficacy of Sulfonamidomethylphosphonate Derivatives.

| Cpd. | R[1] | R[3] | R[4] | Log P | IC$_{50}$ (μM) "C"[1] | Synergy[2] (at μg/mL) Class C E. Cl[3] 10/1[4] | Class A H. In. 10/1[5] | Class A St. A. 10 |
|---|---|---|---|---|---|---|---|---|
| 50 | 2-thienyl | H | OCH$_2$Ph | | 3000 | 2/1 | 1 | 1 |
| 51 | 2-thienyl | H | OMe | | 1700 | 2/1 | 1 | 1 |
| 52 | 2-thienyl | Me$_2$CH (iPr) | PNP | | 1400 | 4/2 | 1 | 1 |
| 53 | 2-thienyl | 4-Me-phenyl | PNP | | 363 | 2/2 | 1 | 1 |
| 54 | 2-thienyl | Me$_2$CH (iPr) | 2-Cl-3-pyridyloxy | | 1800 | 2/1 | 1 | 1 |
| 55 | 3-thienyl | H | 3-pyridyloxy | | 3600 | 4/1 | 2 | 2 |
| 56 | 3-thienyl | H | 2-Cl-3-pyridyloxy | | 1100 | 8/1 | 2 | 1 |
| 57 | 2-thienyl | H | PNP | | 77 | 4/1 | 8 | 2 |
| 58 | 5-Br-2-thienyl | H | OH | | 1,200 | 2/1 | 1 | 1 |
| 59 | 3-(PhNHC(O)NH)-phenyl | H | OH | | 472 | 1/1 | 1 | 1 |

TABLE 1-continued

β-Lactamase Inhibition and Microbiological Efficacy of Sulfonamidomethylphosphonate Derivatives.

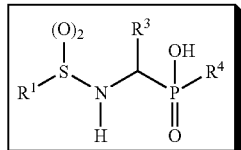

| Cpd. | R[1] | R[3] | R[4] | Log P | IC$_{50}$ (μM) "C"[1] | Synergy[2] (at μg/mL) Class C E. Cl[3] 10/1[4] | Class A H. In. 10/1[5] | Class A St. A. 10 |
|---|---|---|---|---|---|---|---|---|
| 60 | 2-thienyl | phenyl | 2-chloropyridin-3-yloxy | | 603 | 2/1 | 1 | 1 |
| 61 | 2-thienyl | H | 4-chlorophenoxy | | 3,500 | 2/1 | 1 | 1 |
| 62 | 2-thienyl | benzyl | PNP | | 44 | 2/1 | | |
| 63 | 2-thienyl | benzyl | 2-chloropyridin-3-yloxy | | 40 | 2/1 | | |
| 64 | 2-benzothienyl | phenyl | PNP | 0.56 | 84 | 2/2 | | |
| 65 | 2-benzothienyl | benzyl | PNP | 0.86 | 365 | 1 | | |
| 66 | 2-benzothienyl | benzyl | 2-chloropyridin-3-yloxy | 0.24 | 217 | 1 | | |
| 67 | 2-benzothienyl | cinnamyl | 2-chloropyridin-3-yloxy | 0.16 | 20 | 1 | | |

TABLE 1-continued

β-Lactamase Inhibition and Microbiological Efficacy of Sulfonamidomethylphosphonate Derivatives.

| Cpd. | R[1] | R[3] | R[4] | Log P | IC$_{50}$ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 68 | 2-thienyl | cinnamyl | 2-chloropyridin-3-yloxy | −0.84 | 52 | | | |
| 69 | 3-methylthienyl | H | 2-fluoro-4-nitrophenoxy | | 28 | 4/2 | 16 | 2 |
| 70 | 3-(phenylureido)phenyl | H | 2-chloropyridin-3-yloxy | | 93 | 2/2 | 1 | 1 |
| 71 | 5-bromo-2-methylthienyl | H | 5-chloropyridin-3-yloxy | | 84 | 2/1 | 16 | 2 |
| 72 | 5-methyl-8-(dimethylamino)naphthyl | H | PNP | | 4 | 2[7] | | |
| 73 | 3-methylfuryl | H | OH | | | | | |
| 74 | 3-methylfuryl | H | PNP | | 34 | 4/2 | 1 | 1 |
| 75 | 3-methylfuryl | H | 2-fluoro-4-nitrophenoxy | | 35 | 4/4 | 16 | 2 |

TABLE 1-continued

β-Lactamase Inhibition and Microbiological Efficacy of Sulfonamidomethylphosphonate Derivatives.

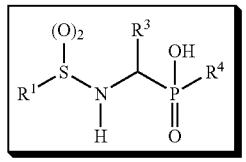

| Cpd. | R[1] | R[3] | R[4] | Log P | IC$_{50}$ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 76 | 3-methylfuran | H | 2-chloro-3-pyridyloxy | | 502 | 4/2 | 1 | 1 |
| 77 | benzothiophen-2-yl | H | PNP | | 0.4 | 12/3 | 24 | 6 |
| 78 | thiophen-2-yl | H | 3-(NMe$_2$)phenoxy | | 3000 | 1/1 | 1 | 1 |
| 79 | thiophen-2-yl | H | OBn | | 3000 | 2/1 | 1 | 1 |
| 80 | thiophen-2-yl | H | OMe | | 1700 | 2/1 | 1 | 1 |
| 81 | thiophen-2-yl | H | 3-(CO$_2$Bn)phenoxy | −0.23 | 53 | 4/1 | 1 | 1 |
| 82 | benzothiophen-2-yl | H | 2-fluoro-4-nitrophenoxy | −0.51 | 0.1 | 8/8 | 32 | 2 |
| 83 | benzothiophen-2-yl | H | 3-pyridyloxy | −1.14 | 88 | 4/1 | 8 | 2 |
| 84 | benzothiophen-2-yl | H | 3-(CO$_2$Bn)phenoxy | 0.64 | 10 | 2/2 | 1 | 1 |

TABLE 1-continued
β-Lactamase Inhibition and Microbiological Efficacy of Sulfonamidomethylphosphonate Derivatives.
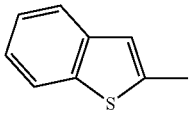
| Cpd. | R[1] | R[3] | R[4] | Log P | IC$_{50}$ (μM) E. Cl[3] "C"[1] | Synergy[2] (at μg/mL) Class C E. Cl[3] 10/1[4] | Class A H. In. 10/1[5] | St. A. 10 |
|---|---|---|---|---|---|---|---|---|
| 85 | 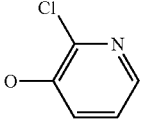 | H | 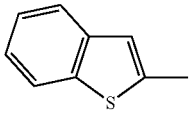 (Cl, O-pyridine) | −1.11 | 64 | 4/1 | 1 | 1 |
| 86 | 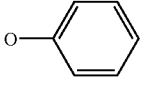 | H | 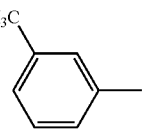 (O-phenyl) | −0.61 | 826 | 4/1 | 1 | 1 |
| 87 | H$_3$C-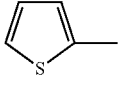 | H | PNP | −0.51 | 7 | 1/1 | 16 | 2 |
| 88 | 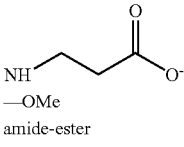 | H | 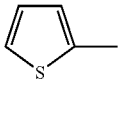<br>—OMe<br>amide-ester | | 1,500 | 1/1 | 1 | 1 |
| 89 | 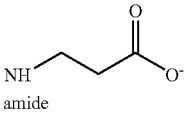 | H | 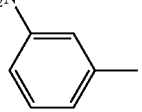<br>amide | | 359 | 4 | | |
| 90 | O$_2$N-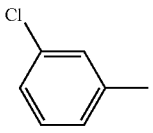 | H | PNP | −0.99 | 6 | 1/1 | 32 | 4 |
| 91 | Cl-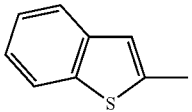 | H | PNP | −0.62 | 5 | 4/2 | 32 | 2 |
| 92 | 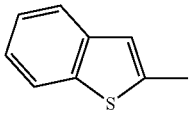 | H | OH<br>acid | −1.70 | 446 | 2 | | |

TABLE 1-continued

β-Lactamase Inhibition and Microbiological Efficacy of Sulfonamidomethylphosphonate Derivatives.

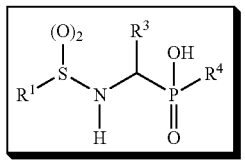

| Cpd. | R¹ | R³ | R⁴ | Log P | IC$_{50}$ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 93 | 2-Cl, 3-methylphenyl | H | PNP | −0.71 | 9 | 4/2 | 4 | 1 |
| 94 | 3-amino-5-methylphenyl (H₂N-) | H | O-C₆H₄-NH₂ (4-aminophenoxy) | | 175 | 1 | | |
| 95 | 2-benzothienyl | H | O-C₆H₄-CO₂Me (4-) | −0.40 | 6 | 1/1 | 8 | 1 |
| 96 | 2-benzofuranyl | H | O-(2-chloropyridin-3-yl) | −1.06 | 18 | 2/1 | 2 | 1 |
| 97 | 2-benzofuranyl | H | PNP | −0.69 | 2 | 8 | | |
| 98 | 2-benzothienyl | H | O-C₆H₄-CO₂Me (3-) | −0.55 | 39 | 1/1 | 2 | 1 |
| 99 | 2-benzothienyl | H | O-C₆H₄-CO₂Bn (4-) | 0.42 | 3 | 4/2 | | |
| 100 | 6-MeO-2-benzothienyl | H | PNP | −0.31 | 0.4 | 5/2 | | |
| 101 | 6-MeO-2-benzothienyl | H | O-(2-chloropyridin-3-yl) | −0.91 | 16 | 9/1 | | |

TABLE 1-continued

β-Lactamase Inhibition and Microbiological Efficacy of Sulfonamidomethylphosphonate Derivatives.

[Structure: R¹-S(O)₂-N(H)-CH(R³)-P(OH)(=O)-R⁴]

| Cpd. | R¹ | R³ | R⁴ | Log P | IC₅₀ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 102 | 2-thiazolyl | H | PNP | −1.23 | 12 | 22/2 | | |
| 103 | 2-furyl | H | PNP | −1.33 | 52 | 4/1 | | |
| 104 | 2,5-dimethylthien-2-yl (Me-thiophene-) | H | PNP | −1.23 | 5 | 11/2 | | |
| 105 | 2-benzofuryl | H | OH, Mono-acid, Mono-sodium salt | −0.68 | 83 | 8 | | |
| 106 | 2-benzofuryl | H | O-(2-F, 4-NO₂-phenyl) | −0.47 | 0.4 | 2/1 | | |
| 107 | 2-benzofuryl | H | O-(3-CO₂Bn-phenyl) | 0.38 | 46 | 8/1 | | |
| 108 | 2-benzofuryl | H | O-(3-CO₂⁻-phenyl) | −0.85 | 234 | 4/2 | | |
| 109 | 2-benzofuryl | H | O-(4-CO₂Bn-phenyl) | 0.45 | 9 | 4/1 | | |
| 110 | 2-benzofuryl | H | O-(4-CO₂⁻-phenyl) | −2.10 | 83 | 4/2 | | |
| 111 | 6-MeO-2-benzothienyl | H | O-(4-C(=O)OBn-phenyl) | 0.58 | 3 | 4 | | |

TABLE 1-continued
β-Lactamase Inhibition and Microbiological Efficacy of Sulfonamidomethylphosphonate Derivatives.
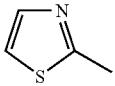
| Cpd. | R¹ | R³ | R⁴ | Log P | IC$_{50}$ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 112 | 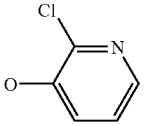 | H | 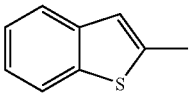 | −0.35 | 60 | 16 | | |
| 113 | 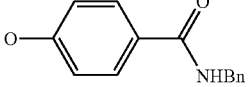 | H | 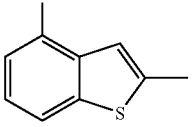 | −0.24 | 19 | 8 | | |
| 114 | 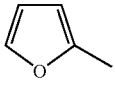 | H | PNP | −0.055 | 0.3 | 6 | | |
| 115 | 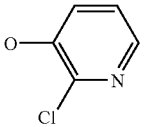 | H | 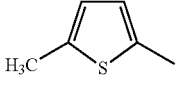 | −0.46 | 116 | 16 | | |
| 116 | 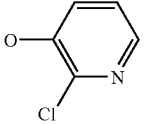 | H | 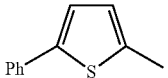 | −0.41 | 48 | 4 | | |
| 117 | 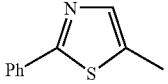 | H | PNP | −0.015 | 0.4 | 4 | | |
| 118 | 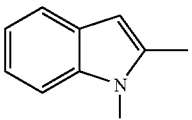 | H | PNP | −0.31 | 0.3 | 4 | | |
| 119 | 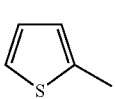 | H | PNP | 0.42 | 1 | 4 | | |
| 120 | 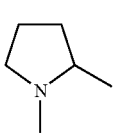 |  | PNP | −1.15 | 1,000 | 4 | | |

TABLE 1-continued
β-Lactamase Inhibition and Microbiological Efficacy of
Sulfonamidomethylphosphonate Derivatives.
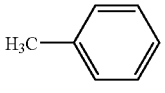
| Cpd. | R[1] | R[3] | R[4] | Log P | IC$_{50}$ (μM) Class C "C"[1] | Synergy[2] (at μg/mL) Class C E. Cl[3] 10/1[4] | Class A H. In. 10/1[5] | St. A. 10 |
|---|---|---|---|---|---|---|---|---|
| 121 | 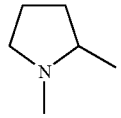 | 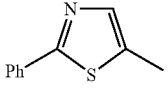 | PNP | −0.73 | 4,000 | 8 | | |
| 122 | 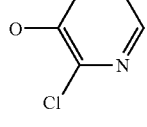 | H | 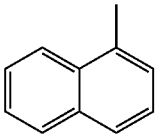 | −1.08 | 11 | 2 | | |
| 123 | 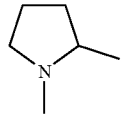 | 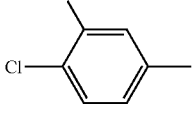 | PNP | −0.19 | 101 | 4 | | |
| 124 | 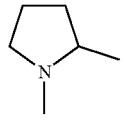 | 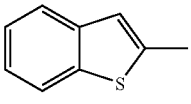 | PNP | −0.22 | 242 | 4 | | |
| 125 | 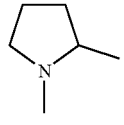 | 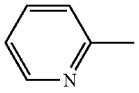 | PNP | −0.065 | 223 | 2 | | |
| 126 | 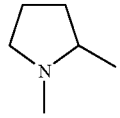 | 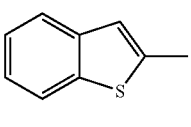 | PNP | −1.01 | 244 | 4 | | |
| 127 | 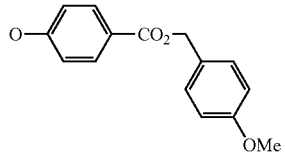 | H | 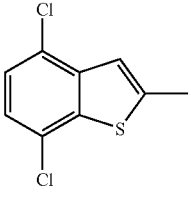 | 0.61 | 1 | 1 | | |
| 128 |  | H | PNP | 0.45 | 0.1 | 16 | | |

TABLE 1-continued

β-Lactamase Inhibition and Microbiological Efficacy of Sulfonamidomethylphosphonate Derivatives.

| Cpd. | R[1] | R[3] | R[4] | Log P | IC$_{50}$ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 129 | 1-methylnaphthyl | N-methylpyrrolidinyl | 2-chloropyridin-3-yloxy | −0.85 | 499 | 2 | | |
| 130 | 2-methylthienyl | N-methylpyrrolidinyl | 2-chloropyridin-3-yloxy | −0.90 | 1,400 | 4 | | |
| 131 | 5-phenyl-2-methylthienyl | H | 2-chloropyridin-3-yloxy | −0.65 | 29 | 2 | | |
| 132 | 4,7-dichloro-2-methylbenzothienyl | H | 4-(benzyloxycarbonyl)phenoxy | 0.70 | 0.4 | 4 | | |
| 133 | 3-methylbenzothienyl | H | PNP | −0.68 | 6 | 4 | | |
| 134 | 3-methylbenzothienyl | H | 2-chloropyridin-3-yloxy | −1.08 | 196 | 4 | | |
| 135 | 3-methylbenzothienyl | H | 4-(benzyloxycarbonyl)phenoxy | 0.48 | 6 | | | |
| 136 | 2-methylbenzothienyl | H | 4-methoxyphenoxy | 0.095 | 358 | 4 | | |

TABLE 1-continued
β-Lactamase Inhibition and Microbiological Efficacy of Sulfonamidomethylphosphonate Derivatives.
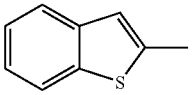
| Cpd. | R[1] | R[3] | R[4] | Log P | IC$_{50}$ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 137 | 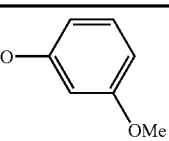 | H | 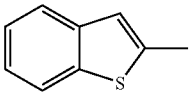 | −0.52 | 593 | 4 | | |
| 138 | 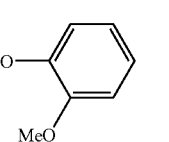 | H | 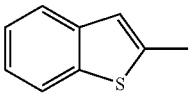 | | 755 | 2 | | |
| 139 | 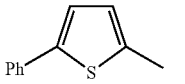 | H | (OBn)$_2$ Diester | | | 1 | | |
| 140 | 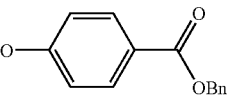 | H | 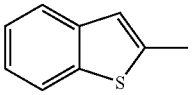 | −0.11 | 4 | 2 | | |
| 141 | 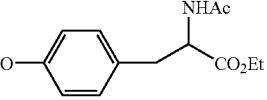 | H | 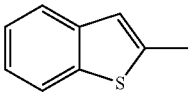 | −0.78 | 655 | 4 | | |
| 142 | 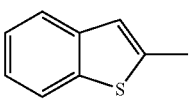 | H N—Me | PNP | −0.091 | 1.3K | 2 | | |
| 143 | 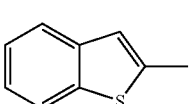 | H N-phenethyl | PNP | 1.17 | 133 | 4 | | |
| 144 | 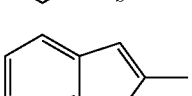 | H N—Et | PNP | −0.036 | 463 | 4 | | |
| 145 | 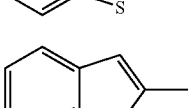 | H N-benzyl | PNP | 0.86 | 94 | 4 | | |
| 146 | 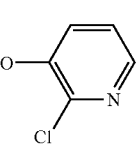 | H N—Me | (pyridine structure with Cl) | −0.30 | 2,500 | 1 | | |

TABLE 1-continued

β-Lactamase Inhibition and Microbiological Efficacy of Sulfonamidomethylphosphonate Derivatives.

| Cpd. | R¹ | R³ | R⁴ | Log P | IC$_{50}$ ($\mu$M) "C"[1] | Synergy[2] (at µg/mL) Class C E. Cl[3] 10/1[4] | Class A H. In. 10/1[5] | St. A. 10 |
|---|---|---|---|---|---|---|---|---|
| 147 | benzothiophen-2-yl | H N—Me | 3-CF₃-phenoxy | 0.84 | 1,200 | 1 | | |
| 148 | benzothiophen-2-yl | H | 3-CF₃-phenoxy | 0.13 | 505 | 2 | | |
| 149 | benzothiophen-2-yl | H | 2-CF₃-phenoxy | −0.1 | 972 | 1 | | |
| 150 | benzothiophen-2-yl | H N—Me | 2-naphthyloxy | 0.65 | 765 | | | |
| 151 | benzothiophen-2-yl | H | 4-CF₃-phenoxy | 0.23 | | | | |
| 152 | benzothiophen-2-yl | H | OCH₂Ph | −0.57 | 96 | 4 | | |
| 153 | 7-Br-benzothiophen-2-yl | H | PNP | 0.17 | 0.2 | 16 | | |
| 154 | 7-Br-benzothiophen-2-yl | H N—Me | PNP | 0.62 | 11 | 4 | | |
| 155 | 5-(4-MeO-phenyl)thiophen-2-yl | H | PNP | −0.09 | 2.0 | 4 | | |

TABLE 1-continued

β-Lactamase Inhibition and Microbiological Efficacy of Sulfonamidomethylphosphonate Derivatives.

| Cpd. | R[1] | R[3] | R[4] | Log P | IC$_{50}$ (μM) "C"[1] | Synergy[2] (at μg/mL) Class C E. Cl[3] 10/1[4] | Synergy[2] (at μg/mL) Class A H. In. 10/1[5] | Synergy[2] (at μg/mL) Class A St. A. 10 |
|---|---|---|---|---|---|---|---|---|
| 156 | 4-MeO-C6H4-thiophene | H | 2-Cl-pyridin-3-yloxy | −0.28 | 32 | 2 | | |
| 157 | 2-thienyl | CH2CH2CH2Ph | 2-Cl-pyridin-3-yloxy | −0.51 | 432 | 1 | | |
| 158 | 2-thienyl | CH2CH2CH2Ph | PNP | 0.13 | 213 | 1 | | |
| 159 | 2-thienyl | CH=CHPh | PNP | −0.25 | 71 | 1 | | |
| 160 | 2-thienyl | CH2CH2-(pyridin-4-yl) | 2-Cl-pyridin-3-yloxy | −0.69 | 219 | 1 | | |
| 161 | benzothiophen-2-yl | CH2CH2-(pyridin-4-yl) | 2-Cl-pyridin-3-yloxy | −0.72 | 140 | 1 | | |
| 162 | benzothiophen-2-yl | CH2CH2-(4-CO2Me-C6H4) | 2-Cl-pyridin-3-yloxy | 0.28 | 213 | 1 | | |
| 163 | benzothiophen-2-yl | CH2CH2-(4-CO2−-C6H4) | 2-Cl-pyridin-3-yloxy | −1.30 | 497 | | | |

TABLE 1-continued

β-Lactamase Inhibition and Microbiological Efficacy of Sulfonamidomethylphosphonate Derivatives.

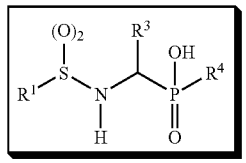

| Cpd. | R[1] | R[3] | R[4] | Log P | IC$_{50}$ (μM) E. Cl[3] "C"[1] | Synergy[2] (at μg/mL) Class C H. In. 10/1[4] | Class A H. In. 10/1[5] | St. A. 10 |
|---|---|---|---|---|---|---|---|---|
| 164 | 6,7-dichlorobenzothiophen-2-yl | H | PNP | −0.01 | 0.31 | 6 | | |
| 165 | 6,7-dichlorobenzothiophen-2-yl | H N—Me | PNP | 0.71 | 18 | 2 | | |
| 166 | 2-methylthiazol-2-yl | H | 4-OMe-phenoxy | | 2,800 | 1 | | |
| 167 | 5-(4-phenylphenyl)thiophen-2-yl | H | PNP | 0.53 | 2 | 2 | | |
| 168 | 5-(4-phenylphenyl)thiophen-2-yl | H | 2-chloro-3-pyridyloxy | 0.92 | 51 | 1 | | |
| 169 | benzothiophen-2-yl | H | 4-(benzyloxy)phenoxy | −0.07 | 140 | 1 | | |
| 170 | benzothiophen-2-yl | H | 4-(phenoxy)phenoxy | 0.70? | 67 | 1 | | |
| 171 | benzothiophen-2-yl | H | 2,6-dimethoxyphenoxy | −0.49 | 214 | 1 | | |

TABLE 1-continued

β-Lactamase Inhibition and Microbiological Efficacy of Sulfonamidomethylphosphonate Derivatives.

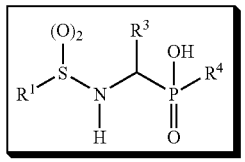

| Cpd. | R[1] | R[3] | R[4] | Log P | IC$_{50}$ (μM) "C"[1] | Synergy[2] (at μg/mL) Class C E. Cl[3] 10/1[4] | Class A H. In. 10/1[5] | St. A. 10 |
|---|---|---|---|---|---|---|---|---|
| 172 | benzothiophen-2-yl | H | 2,3-dimethoxyphenoxy | −0.54 | 1.9K | 1 | | |
| 173 | benzothiophen-2-yl | H | 2-methoxy-6-fluorophenoxy | −0.14 | 408 | 1 | | |
| 174 | benzothiophen-2-yl | H | 2-methoxy-4-chlorophenoxy | −0.41 | 829 | 1 | | |
| 175 | benzothiophen-2-yl | H | 2-methoxy-4-nitrophenoxy | −0.69 | 9 | 1 | | |
| 176 | benzothiophen-2-yl | H | 2-chloro-4-methoxyphenoxy | −0.31 | 972 | 1 | | |
| 177 | benzothiophen-2-yl | H | 4-aminophenoxy | | 618 | 1 | | |
| 178 | 7-bromobenzothiophen-2-yl | H | 4-methoxyphenoxy | 0.21 | 185 | 1 | | |
| 179 | benzothiazol-2-yl | H | 2-chloropyridin-3-yloxy | −1.10 | 46 | | | |

TABLE 1-continued

β-Lactamase Inhibition and Microbiological Efficacy of
Sulfonamidomethylphosphonate Derivatives.

| Cpd. | $R^1$ | $R^3$ | $R^4$ | Log P | IC$_{50}$ ($\mu$M) "C"[1] | Synergy[2] (at $\mu$g/mL) Class C E. Cl[3] 10/1[4] | Class A H. In. 10/1[5] | St. A. 10 |
|---|---|---|---|---|---|---|---|---|
| 180 | benzothiazol-2-yl | H | PNP | −0.90 | 1.4 | | | |
| 181 | benzothiophen-2-yl | H | 2,5-di(OMe)phenyl-O- | | 1.9K | 1 | | |
| 182 | benzothiophen-2-yl | H | 4-NHAc-phenyl-O- | −0.98 | 1.6K | 1 | | |
| 183 | 4,7-dichlorobenzothiophen-2-yl | H | 4-OMe-phenyl-O- | 0.34 | 205 | 1 | | |
| 184 | 4,7-di(OMe)benzothiophen-2-yl | H | PNP | −0.33 | 0.5 | 32 | | |
| 185 | 4,7-dichlorobenzothiophen-2-yl | H | 2-Cl-pyridin-3-yl-O- | −0.06 | 5 | | | |
| 186 | 4,5,7-trichlorobenzothiophen-2-yl | H | PNP | 0.67 | 0.2 | | | |

TABLE 1-continued

β-Lactamase Inhibition and Microbiological Efficacy of
Sulfonamidomethylphosphonate Derivatives.

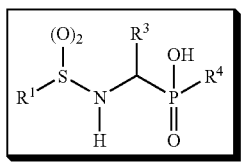

| | | | | | | Synergy[2] (at µg/mL) | | |
| | | | | | IC$_{50}$ | Class C | Class A | |
| Cpd. | R[1] | R[3] | R[4] | Log P | (µM) | E. Cl[3] "C"[1] 10/1[4] | H. In. 10/1[5] | St. A. 10 |
|---|---|---|---|---|---|---|---|---|
| 187 | 4,7-dimethoxybenzothiophen-2-yl (OMe, OMe) | H | 2-chloropyridin-3-yloxy | | 27 | | | |
| 188 | 7-bromobenzothiophen-2-yl (Br) | H | 2-chloropyridin-3-yloxy | | | | | |
| 189 | PhS(O)$_2$NHNHP(O)(O$^-$)O-(4-nitrophenyl) | | | | 62 | 2 | | |

[1]Class C β-lactamase [P99].

[2]Expressed as the ratio of the antibiotic MIC determined in the absence of β-lactamase inhibitor to the antibiotic MIC determined in the presence of β-lactamase inhibitor.

[3]E. Cl = *Enterobacter cloacae* [ATCC #23355]; H. In. = *Haemophilius influenzae* [ATCC #43163]; St. A. = *Staphylococcus aureus* [MGH:MA #50848].

[4]The first value provided was determined at an inhibitor concentration of 10 µg/mL, and the second value was determined at an inhibitor concentration of 1 µg/mL. Where only one value is provided, it was determined at an inhibitor concentration of 10 µg/mL.

[5]Values within parentheses were determined at an inhibitor concentration of 100 µg/mL.

[6]PNP = p-nitrophenol

[7]In four separate tests, synergy values of 32, 2, 1, and 1 were obtained. The value of 32 is believed to be an outlyer.

TABLE 2

β-Lactamase Inhibition and Microbiological Efficacy of Sulfonamidomethylphosphonate Derivatives.

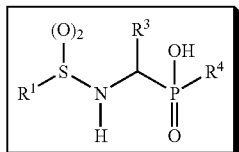

| Cpd. | R$^1$ | R$^3$ | R$^4$ | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 190 | 5-O⁻-2-methylbenzothiophene | H | PNP | 0.58 | 0.7 | >200 | >200 | 8/16 |
| 191 | 2-thienyl | 3-propylpyridine | OH | 0.78 | 84 | >200 | >200 | 0 |
| 192 | 2-thienyl | 4-NO₂-styryl | OH | 0.58 | 128 | >200 | >200 | 0 |
| 193 | 5-methylbenzothiophene | H | PNP | 0.55 | 4 | >200 | >200 | 4 |
| 194 | 5-methylbenzothiophene | H | 2-Cl-3-O-pyridine | 0.37 | 648 | >200 | >200 | 0 |
| 195 | 5-Br-2-methylbenzothiophene | H | PNP | 0.03 | 0.6 | >200 | >200 | 2 |
| 196 | 6-EtO-2-methylbenzothiazole | H | PNP | 0.60 | 0.8 | >200 | >200 | 4 |
| 197 | 6-EtO-2-methylbenzothiazole | H | 3-O-5-Cl-pyridine | 0.64 | 106 | >200 | | 2 |
| 198 | 2-methylbenzothiophene | H | 4-CHO-phenoxy | 0.66 | 3 | >200 | >200 | 8 |
| 199 | 2-methylbenzothiophene | H | 4-OCOCH₃-phenoxy | 0.72 | 25 | >200 | >200 | 0 |
| 200 | 2-CH₃CONH-5-methyl-1,3,4-thiadiazole | CH₂N(CH₃)₂ | PNP | 0.87 | 1200 | >200 | >200 | 2 |

TABLE 2-continued

β-Lactamase Inhibition and Microbiological Efficacy of Sulfonamidomethylphosphonate Derivatives.

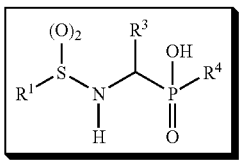

| Cpd. | R¹ | R³ | R⁴ | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 201 | benzothiophene-2-yl | H | 4-cyanophenoxy | | 1 | >200 | >200 | 8 |
| 202 | benzothiophene-2-yl | H | 5-chloroquinolin-8-yloxy | | 594 | >200 | >200 | 0 |
| 203 | benzothiophene-2-yl | H | naphthalen-2-yloxy | | 361 | >200 | >200 | 0 |
| 204 | benzothiophene-2-yl | H | benzo[1,3]dioxol-5-yloxy | | 87 | >200 | >200 | 0 |
| 205 | benzothiophene-2-yl | H | 5,7-dichloroquinolin-8-yloxy | | 334 | >200 | >200 | 8 |
| 206 | 5,6-dimethoxybenzothiophene-2-yl | H | PNP | 0.85 | 0.1 | 467 | >200 | 4 |
| 207 | 7-(4,6-dimethoxypyrimidin-2-ylamino)benzothiophene-2-yl | H | PNP | | 1 | 275 | >200 | 2 |
| 208 | 5,6-dioxidobenzothiophene-2-yl | H | PNP | 0.56 | 3 | >200 | >200 | 4 |

TABLE 2-continued

β-Lactamase Inhibition and Microbiological Efficacy of Sulfonamidomethylphosphonate Derivatives.

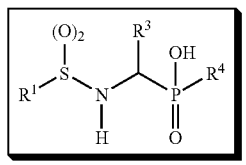

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 209 | benzothiophen-2-yl | H | O-C$_6$H$_4$-Br (para) | 0.10 | 142 | >200 | >200 | 2 |
| 210 | 4,7-dichlorobenzothiophen-2-yl | H | O-C$_6$H$_4$-Br (para) | 0.30 | 23 | 149 | >200 | 0 |
| 211 | benzothiophen-2-yl | H | O-C$_6$H$_4$-NHPh (meta) | | 50 | >200 | | 0 |
| 212 | 4,7-dichlorobenzothiophen-2-yl | H | O-C$_6$H$_4$-NHPh (meta) | 1.0 | 9 | 64 | 201 | 0 |
| 213 | 4,7-dichlorobenzothiophen-2-yl | H | O-C$_6$H$_4$-NHSO$_2$Ph (para) | | 50 | 14 | >200 | 0 |
| 214 | 5,7-dichlorobenzothiophen-2-yl | H | PNP | 0.2 | 87 | >200 | | 16 |
| 215 | benzothiophen-2-yl | H | O-C$_6$H$_4$-SO$_2$NHPh (para) | | 93 | 494 | | 0 |

TABLE 2-continued

β-Lactamase Inhibition and Microbiological Efficacy of Sulfonamidomethylphosphonate Derivatives.

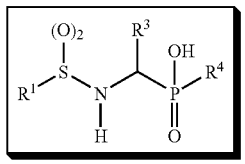

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 216 | benzothiophen-2-yl | H | (naphthalimide-OCH$_2$CH$_2$OCH$_3$) | 196 | >200 | >200 | 0 | |
| 217 | benzothiophen-2-yl | H | (4-imidazolylphenoxy) | 367 | >200 | >200 | | |
| 218 | benzothiophen-2-yl | H | (2-hydroxyphenyl-1-phenylpyrazol-4-yl ketone) | 356 | >200 | >200 | | |
| 219 | benzothiophen-2-yl | H | (4-CH$_2$CN-phenoxy) | 619 | >200 | >200 | 0 | |
| 220 | benzothiophen-2-yl | H | (4-(5-phenyl-1H-pyrazol-3-yl)phenoxy) | 48 | >200 | >200 | 0 | |
| 221 | 4,7-dichlorobenzothiazol-2-yl | H | PNP | 0.5 | >200 | >200 | 8 | |
| 222 | thieno[3,2-b]pyridin-2-yl | H | PNP | 7 | >200 | >200 | 4 | |

TABLE 2-continued

β-Lactamase Inhibition and Microbiological Efficacy of Sulfonamidomethylphosphonate Derivatives.

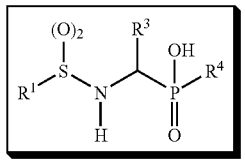

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 223 | 4,7-dichlorobenzothiophen-2-yl | H | 4-(N-benzylcarbamoyl)phenoxy | | 9 | 278 | >200 | 0 |
| 224 | 4,7-dichlorobenzothiazol-2-yl | N(CH$_3$)$_2$ | PNP | | 183 | >200 | >200 | 0 |
| 225 | benzothiophen-2-yl | H | 4-(CH$_2$CONH$_2$)phenoxy | | 1400 | >200 | | 0 |
| 226 | benzothiophen-2-yl | H | 2-fluoro-4-cyanophenoxy | | 0.3 | 576 | | 16 |
| 227 | 4,7-dichlorobenzothiazol-2-yl | H | 2-chloropyridin-3-yloxy | | 9 | >200 | | 2 |
| 228 | benzothiophen-2-yl | H | 4-iodophenoxy | | 98 | >200 | | 2 |
| 229 | 5-chlorobenzothiazol-2-yl | H | PNP | | 0.9 | | | |
| 230 | 5-chlorobenzothiazol-2-yl | H | 2-chloropyridin-3-yloxy | | 29 | | | |

TABLE 2-continued
β-Lactamase Inhibition and Microbiological Efficacy of Sulfonamidomethylphosphonate Derivatives.
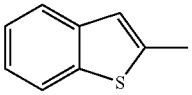
| Cpd. | R¹ | R³ | R⁴ | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 231 | 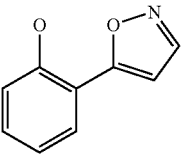 | H | 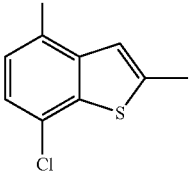 | | 165 | >200 | >200 | |
| 232 | 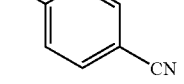 | H | 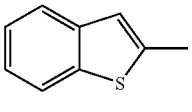 | | 0.2 | 250 | >200 | 16 |
| 233 | 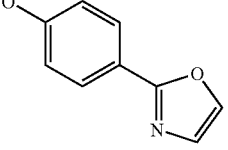 | H | 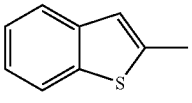 | | 205 | >200 | >200 | 0 |
| 234 | 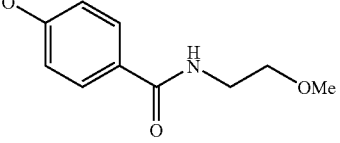 | H | 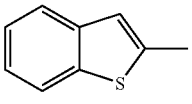 | | 219 | >200 | >200 | 0 |
| 235 | 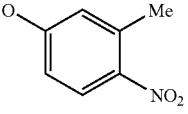 | H | 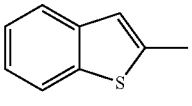 | | 5 | >200 | | 8 |
| 236 | 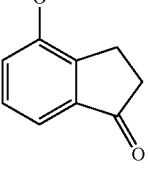 | H | 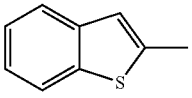 | | 578 | >200 | >200 | |
| 237 | 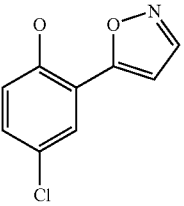 | H | | 0.3 | 204 | >200 | >200 | 0 |

TABLE 2-continued

β-Lactamase Inhibition and Microbiological Efficacy of Sulfonamidomethylphosphonate Derivatives.

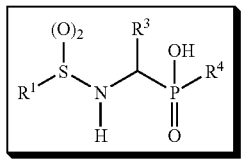

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 238 | benzothiophene-2-yl | H | 4-(SO$_2$Et)phenoxy | −0.4 | 53 | 131 | >200 | 0 |
| 239 | 4,7-dichlorobenzothiophene-2-yl | H | 3-Me-4-NO$_2$-phenoxy | 0.6 | 0.5 | 282 | >200 | 16 |
| 240 | benzothiophene-2-yl | H | 5-bromo-2-(isoxazol-5-yl)phenoxy | 0.1 | 458 | >200 | | 0 |
| 241 | benzothiophene-2-yl | H | 4-((pyridin-4-yl)methoxycarbonyl)phenoxy | 5 | >200 | >200 | 2 | |
| 242 | benzothiophene-2-yl | H | 4-((pyridin-4-yl)methoxycarbonyl)phenoxy | −0.2 | 5 | >200 | >200 | 2 |
| 243 | benzothiophene-2-yl | H | 4-((pyridin-3-yl)methoxycarbonyl)phenoxy | −0.4 | 6 | >200 | >200 | 2 |
| 244 | benzothiophene-2-yl | H | 4-((thiophen-2-yl)methoxycarbonyl)phenoxy | | 4 | >200 | >200 | 4 |

TABLE 2-continued

β-Lactamase Inhibition and Microbiological Efficacy of Sulfonamidomethylphosphonate Derivatives.

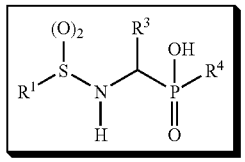

| Cpd. | R¹ | R³ | R⁴ | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 245 | 4,7-dichlorobenzothiophen-2-yl | H | 4-(imidazol-1-yl)phenoxy | −0.1 | 43 | 272 | | 0 |
| 246 | benzothiophen-2-yl | H | 5,5-diphenylhydantoin-N-yl phenoxy | −0.1 | 623 | >200 | >200 | 2 |
| 247 | benzothiophen-2-yl | H | 2-CF₃-4-NO₂-phenoxy | | 0.8 | 20 | >200 | 8 |
| 248 | 4,7-dichlorobenzothiophen-2-yl | H | 2-F-4-NO₂-phenoxy | 0.3 | 0.06 | 103 | | 32 |
| 249 | benzothiophen-2-yl | H | 4-(CO₂CH₂CH₂Ph)phenoxy | | 14 | >200 | | 2 |
| 250 | benzothiophen-2-yl | H | 4-(CO₂CH₂CH₂CH₂Ph)phenoxy | 0.6 | 9 | >200 | | 2 |
| 251 | benzothiophen-2-yl | H | 3-NO₂-phenoxy | −0.6 | 30 | >200 | | 0 |

TABLE 2-continued
β-Lactamase Inhibition and Microbiological Efficacy of Sulfonamidomethylphosphonate Derivatives.
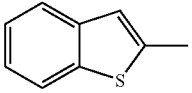
| Cpd. | R¹ | R³ | R⁴ | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 252 | 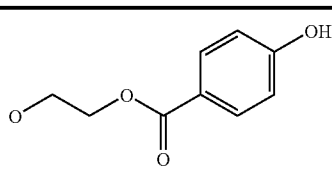 | H | 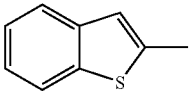 | | 1300 | >200 | | 0 |
| 253 | 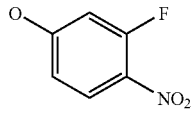 | H | 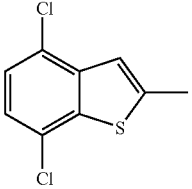 | −0.4 | 0.2 | | 68 | 16 |
| 254 | 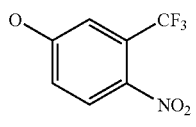 | H | 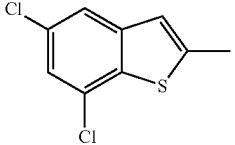 | | 0.3 | | 13 | 32 |
| 255 | 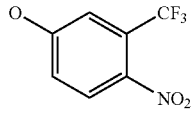 | H | 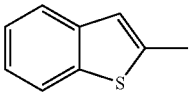 | 0.7 | 0.6 | | 6 | 8 |
| 256 | 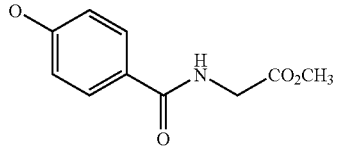 | H | 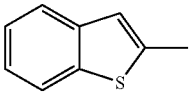 | | 174 | >200 | | 0 |
| 257 | 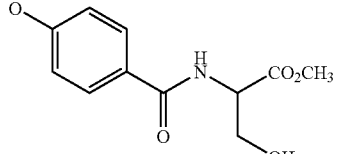 | H | 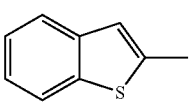 | | 354 | >200 | | 0 |
| 258 | 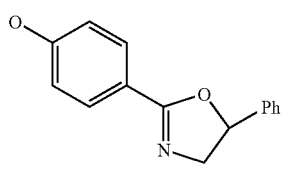 | H | | | 80 | >200 | | 0 |

TABLE 2-continued

β-Lactamase Inhibition and Microbiological Efficacy of
Sulfonamidomethylphosphonate Derivatives.

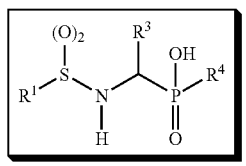

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 259 | 2-benzothienyl | H | 4-(5-methoxycarbonyl-4,5-dihydrooxazol-2-yl)phenoxy | | 177 | >200 | | 0 |
| 260 | 2-benzothienyl | H | 4-carbamoylphenoxy | | 130 | >200 | | 0 |
| 261 | 2-benzothienyl | H | 4-(2-hydroxyethylcarbamoyl)phenoxy | | 78 | >200 | | 0 |
| 262 | 2-benzothienyl | H | 4-(1-methoxycarbonyl-2-phenylethylcarbamoyl)phenoxy | | 165 | >252 | | 0 |
| 263 | 2-benzothienyl | H | 4-(3-nitrophenyl)phenoxy | | 81 | >256 | | 0 |
| 264 | 2-benzothienyl | H | 4-(4-fluorophenyl)phenoxy | | 97 | 394 | | 4 |
| 265 | 2-benzothienyl | H | 4-(4-cyanophenyl)phenoxy | | 93 | 359 | | 4 |
| 266 | 2-benzothienyl | H | 4-(phenylcarbamoyl)phenoxy | | 82 | >244 | | 0 |

TABLE 2-continued

β-Lactamase Inhibition and Microbiological Efficacy of
Sulfonamidomethylphosphonate Derivatives.

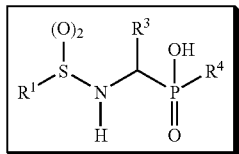

| Cpd. | R¹ | R³ | R⁴ | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 267 | 4,7-diCl-benzothiophen-2-yl | H | 4-(2-methoxyethoxycarbonyl)phenoxy | | 2 | 240 | | 2 |
| 268 | 4-OMe-4,5,6,7-tetrahydrobenzothiophen-2-yl | H | PNP | −0.4 | 3 | >240 | | 2 |
| 269 | 4-OMe-4,5,6,7-tetrahydrobenzothiophen-2-yl | H | 2-CF₃-4-NO₂-phenoxy | −0.2 | 6 | 107 | | 0 |
| 270 | thiazol-2-yl | H | 5-chloropyridin-3-yloxy | | 452 | >200 | | 16 |
| 271 | 4,5,6,7-tetrahydrobenzothiophen-2-yl | H | PNP | 0.3 | 2 | >200 | | 2 |
| 272 | 4-OMe-4,5,6,7-tetrahydrobenzothiophen-2-yl | H | 2-chloropyridin-3-yloxy | | 50 | >200 | | 2 |
| 273 | 4,5,6,7-tetrahydrobenzothiophen-2-yl | H | 2-CF₃-4-NO₂-phenoxy | | 4 | 54 | | 2 |
| 274 | 4,5,6,7-tetrahydrobenzothiophen-2-yl | H | 2-chloropyridin-3-yloxy | | 47 | >200 | | 2 |

TABLE 2-continued

β-Lactamase Inhibition and Microbiological Efficacy of Sulfonamidomethylphosphonate Derivatives.

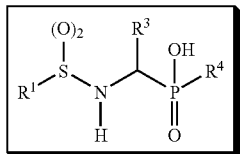

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 275 | 4,7-dichlorobenzothiophen-2-yl | H | 4-cyano-3-nitrophenoxy |  | 0.1 | 21 | | 32/8 |
| 276 | benzothiophen-2-yl | H | 2-(4-phenoxy)-4-CO$_2$Et-thiazoline |  | 63 | >200 | | 4 |
| 277 | benzothiophen-2-yl | H | 4-(thiophen-3-yl)phenoxy |  | 139 | >200 | | 2 |
| 278 | benzothiophen-2-yl | H | 3-fluoro-5-(4-fluorophenyl)phenoxy |  | 137 | >200 | | 2 |
| 279 | benzothiophen-2-yl | H | 3-(4-cyanophenyl)phenoxy |  | 109 | >200 | | 0 |
| 280 | 4,7-dichlorobenzothiophen-2-yl | H | 4-(3,5-difluorophenyl)phenoxy |  | 11 | 68 | | 0 |

TABLE 2-continued

β-Lactamase Inhibition and Microbiological Efficacy of
Sulfonamidomethylphosphonate Derivatives.

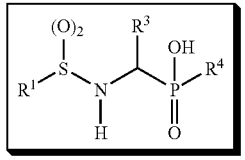

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 281 | 4,7-dichlorobenzothiophen-2-yl | H | 3-fluoro-4'-cyano-biphenyl-4-yloxy | | 4 | 75 | | 4 |
| 282 | 4,7-dichlorobenzothiophen-2-yl | H | 3'-fluoro-4'-cyano-biphenyl-3-yloxy | | 43 | 662 | | 0 |
| 283 | 4,7-dichlorobenzothiophen-2-yl | H | 4'-fluoro-3'-cyano-biphenyl-4-yloxy | | 20 | 74 | | 0 |
| 284 | 5-chlorobenzothiophen-2-yl | H | 2-fluoro-4-cyanophenoxy | −0.3 | 0.4 | 511 | | 8 |
| 285 | 6-ethoxybenzothiophen-2-yl | H | 2-fluoro-4-cyanophenoxy | −0.5 | 0.4 | 356 | | 4 |
| 286 | thien-2-yl | H | 2-fluoro-4-cyanophenoxy | | 2 | >200 | | 16/16 |
| 287 | thien-2-yl | H | 4-cyanophenoxy | | 15 | >200 | | 16/8 |
| 288 | thien-2-yl | H | 5-chloropyridin-3-yloxy | | 375 | >200 | | 8/16 |

TABLE 2-continued

β-Lactamase Inhibition and Microbiological Efficacy of
Sulfonamidomethylphosphonate Derivatives.

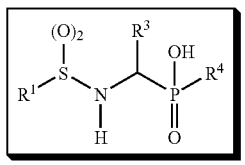

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 289 | 2-methylthiazole | H | 2-F, 4-O, CN-phenyl | | 6 | >200 | | 32/32 |
| 290 | 2-methylthiazole | H | 4-O, CN-phenyl | | 27 | >200 | | 16/32 |
| 291 | 2-methylthiazole | H | 2-CF$_3$, 4-O, NHCOCH$_3$-phenyl | | 666 | | | |
| 292 | 2-methylthiazole | H | 2-CF$_3$, 4-O, NHSO$_2$-(4-methylphenyl)-phenyl | | >240 | >240 | | 0/0 |
| 293 | 2-methylthiazole | H | 2-CF$_3$, 4-O, NHCOPh-phenyl | | 1100 | >300 | | 0/0 |
| 294 | 4,7-dichlorobenzothiophen-2-yl | H | 4-O, NHCOPh-phenyl | | 77 | 149 | | 4 |

TABLE 2-continued

β-Lactamase Inhibition and Microbiological Efficacy of Sulfonamidomethylphosphonate Derivatives.

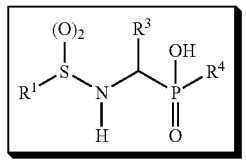

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 295 | 2-methylbenzothiophene | H | 4-O-phenyl-2-CF₃-NHSO₂-(4-methylphenyl) | | 27 | 454 | | 0/0 |
| 296 | 2-methylbenzothiophene | H | 4-O-phenyl-2-CF₃-NHCOPh | | 98 | >200 | | 0/0 |
| 297 | 2-methylthiazole | H | 4-O-phenyl-2-CF₃-NHSO₂Me | | >600 | >200 | | 0/0 |
| 298 | 4,7-dichloro-2-methylbenzothiophene | H | 4-O-phenyl-2-F-CN | | 0.06 | 157 | | 32 |
| 299 | 4,7-dichloro-2-methylbenzothiophene | H | S-phenyl | | 2 | 150 | | 8/8 |
| 300 | 4,7-dichloro-2-methylbenzothiophene | H | 4-O-phenyl-C(O)O-CH₂CH₂OH | | 28 | 130 | | 0/2 |

TABLE 2-continued

β-Lactamase Inhibition and Microbiological Efficacy of Sulfonamidomethylphosphonate Derivatives.

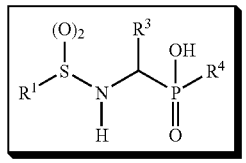

| Cpd. | R¹ | R³ | R⁴ | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 301 | 4,7-dichlorobenzothiophen-2-yl | H | 4-methylphenylthio | 4 | | 74 | | 4/4 |
| 302 | 4,7-dichlorobenzothiophen-2-yl | H | 2-fluoro-4-(trifluoromethyl)phenoxy | 3 | | 141 | | 0/2 |
| 303 | thiophen-2-yl | H | 2-(trifluoromethyl)-4-nitrophenoxy | 9 | | >200 | | 2/2 |
| 304 | thiophen-2-yl | H | 2-fluoro-4-nitrophenoxy | 5 | | >200 | | 16/32 |
| 305 | thiazol-2-yl | H | 2-(trifluoromethyl)-4-cyanophenoxy | 6 | | >200 | | 8/4 |
| 306 | thiazol-2-yl | H | 2-(trifluoromethyl)-4-nitrophenoxy | 7 | | >200 | | 2/4 |
| 307 | thiazol-2-yl | H | 4-((4-(trifluoromethyl)benzyl)oxycarbonyl)phenoxy | 30 | | >200 | | 2/2 |
| 308 | thiazol-2-yl | H | 4-((4-cyanobenzyl)oxycarbonyl)phenoxy | 53 | | >200 | | 0/0 |

TABLE 2-continued

β-Lactamase Inhibition and Microbiological Efficacy of Sulfonamidomethylphosphonate Derivatives.

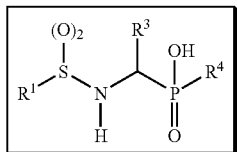

| Cpd. | R[1] | R[3] | R[4] | Log P | IC$_{50}$ (μM) "C"[2] | IC$_{50}$ (μM) "A"[3] | IC$_{50}$ (μM) "B"[4] | Synergy[5] Class C E. Cl[6] 10/1[7] |
|---|---|---|---|---|---|---|---|---|
| 309 | 3-methyl-benzothiophen-2-yl | N(CH$_3$)$_2$ | 4-O-(2-CF$_3$-4-NO$_2$-phenyl) | | 109 | >200 | | 0/0 |
| 310 | 3-methyl-benzothiophen-2-yl | H | 4-O-(2-CF$_3$-4-NO$_2$-phenyl) | 0.7 | 19 | | | 8/8 |
| 311 | 3-methyl-benzothiophen-2-yl | N(CH$_3$)$_2$ | 4-O-(2-F-4-CN-phenyl) | | 170 | >200 | | 0/0 |
| 312 | 3-methyl-benzothiophen-2-yl | H | 4-O-(2-F-4-CN-phenyl) | 0.1 | >200 | | | 16/8 |
| 313 | 2-methyl-thiazol-4-yl | H | 4-S-(4-CH$_3$-phenyl) | | 27 | >200 | | 4/4 |

[2]Class C β-lactamase [P99].
[3]Class A β-lactamase [TEM R+].
[4]Class B β-lactamase [L-1].
[5]Expressed as the ratio of the antibiotic MIC determined in the absence of β-lactamase inhibitor to the antibiotic MIC determined in the presence of β-lactamase inhibitor.
[6]E. Cl = Enterobacter cloacae [ATCC #23355]; H. In. = Haemophilius influenzae [ATCC #43163]; St. A. = Staphylococcus aureus [MGH:MA #50848].
[7]The first value provided was determined at an inhibitor concentration of 10 μg/mL, and the second value was determined at an inhibitor concentration of 1 μg/mL. Where only one value is provided, it was determined at an inhibitor concentration of 10 μg/mL.

EXAMPLE 73

Synergistic Effect of β-Lactamase Inhibitors when Tested Against Highly Resistant β-Lactamase Positive Bacterial Strains Following procedures identical to those described in Example 72, β-lactamase inhibitors were tested for their ability to enhance antibiotic efficacy against β-lactamase positive bacterial strains that are very highly resistant to β-lactam antibiotics. Representative results are presented in Table 3.

Highly Resistant D-Lactamase Positive Strains
Enterobacter cloacae (derepressed)
Pseudomonas aeroginosa [ATCC#12470-resistant]
Stenotrophomonas maltophilia [ATCC#12968-resistant]
Pseudomonas aeroginosa [ATCC#98043010-intermediate resistance]
Stenotrophomonas maltopilia [ATCC#98043029-intermediate resistance]

Successful inhibition of bacterial β-lactamase activity in these assays is expected to be predictive of success in animals and humans. For examples of the successful clinical development of β-lactamase inhibitors identified by in vitro testing, see, e.g., Di Modugno et al., Current Opinion in Anti-Infective Investigational Drugs 1:26-39 (1999); Moellering, J. Antimicrobial Chemotherapy 31 Suppl. A: 1-8 (1993).

TABLE 3

Synergy results from screening against highly resitant microorganisms.

Structure: R¹-S(O)₂-NH-CH(R³)-P(=O)(O⁻)(R⁵)

| Cpd. | R¹ | R³ | R⁵ | IC$_{50}$ (μM) "C"[1] | Resistant Ent. Cloacae[2] 10 μg/mL | 1 μg/mL | Resistant Pseudo. 10 μg/mL | 1 μg/mL |
|---|---|---|---|---|---|---|---|---|
| 15 | 2-thienyl | H | PNP | 18 | 1 | | 1 | |
| 77 | 2-benzothienyl | H | PNP | 0.4 | 5 | | 1 | |
| 72 | 5-(dimethylamino)naphthalen-1-yl (linked via thiophene) | H | PNP | 4 | 1 | 1 | 1 | 1 |
| 76 | 3-furyl | H | 2-chloro-pyridin-3-yloxy | 502 | 5 | | 1 | |
| 82 | 2-benzothienyl | H | 2-fluoro-4-nitrophenoxy | 0.1 | 5 | | 1 | |
| 114 | 4-chloro-2-benzothienyl | H | PNP | 0.3 | 5 | | 1 | |
| 128 | 4,7-dichloro-2-benzothienyl | H | PNP | 0.1 | 5 | 1 | 1 | 1 |

| Cpd. | Resistant Stenotro. 10 μg/mL | 1 μg/mL | Intermed. Pseudo. 10 μg/mL | 1 μg/mL | Intermed. Stenotro. 10 μg/mL | 1 μg/mL |
|---|---|---|---|---|---|---|
| 15 | 1 | | 4 | | 1 | |
| 77 | 5 | | 8 | | 1 | |
| 72 | 1 | 1 | 1 | 1 | 1 | 1 |
| 76 | 5 | | 1 | | 1 | |
| 82 | 5 | | 8 | | 1 | |
| 114 | 4 | | 1 | | 1 | |
| 128 | 1 | 1 | 2 | 1 | 2 | 1 |

[1] Class C β-lactamase [P99].
[2] Enterobacter Cloacae(derepressed), Pseudomonas aeroginosa(#12470-resistant), Stenotrophomonas maltophilia(#12968-resistant), Pseudomonas aeroginosa(#98043010-intermediate resistance), Stenotrophomonas maltophilia(#98043029-intermediate resistance).

TABLE 4
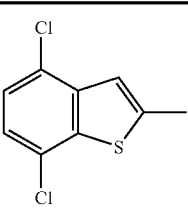
| Cmpd # | R₁ | R | X⁻ | IC$_{50}$ (μM) "C" | IC$_{50}$ (μM) TEM1 "A" | IC$_{50}$ (μM) L-1 "B" | Synergy at 10 μg/ml | | | | LogP or pKa |
|---|---|---|---|---|---|---|---|---|---|---|---|
| | | | | | | | Ent. Cl. | Ent. Faec. | Stap. Aureus | P99 Ent. Bact. | |
| 501 | 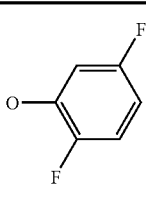 | H | 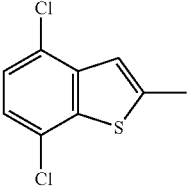 | 6 | 380 | | 2 | 0 | 0 | 0 | |
| 502 | 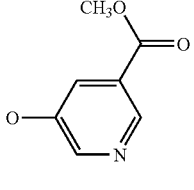 | H | 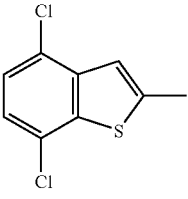 | 12 15 | 12K | | 0 | 2 | 0 | 0 | |
| 503 | 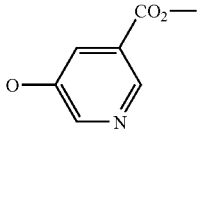 | H | 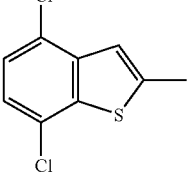 | 30 | >250 | | 4 | 0 | 0 | 0 | |
| 504 | 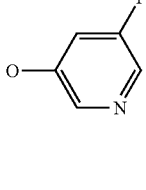 | H | 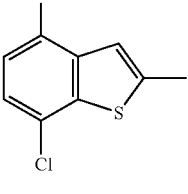 | 1 1 | 3K | | 8 | 2 | 0 | 2 | |
| 505 | 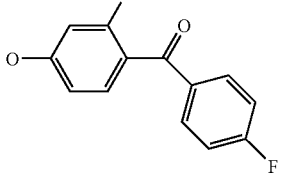 | H | 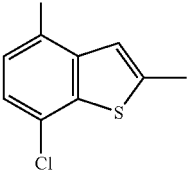 | 109 149 | 126 | | 4 | 2 | 0 | 0 | |
| 506 | 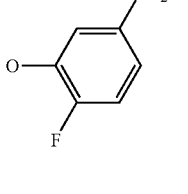 | H | | 37 | >250 | | 2 | 2 | 0 | — | |

TABLE 4-continued

Structure: R¹—SO₂—NH—CHR—P(=O)(X)(O⁻)

| Cmpd # | R₁ | R | X⁻ | IC₅₀ (μM) "C" | IC₅₀ (μM) TEM1 "A" | IC₅₀ (μM) L-1 "B" | Ent. Cl. | Ent. Faec. | Stap. Aureus | P99 Ent. Bact. | LogP or pKa |
|---|---|---|---|---|---|---|---|---|---|---|---|
| 507 | 4,7-dichlorobenzothiophene-2-yl | H | O-pyridin-3-yl with 5-CF₃ | 11 | 585 | | 4 | 2 | 2 | — | |
| 508 | 4,7-dichlorobenzothiophene-2-yl | H | O-(5-pyridyl)-C(=O)NH-CH(CO₂CH₃)-CH₂CH₂-CO₂CH₃ | 153 250 | >250 | | 2 | 2 | 0 | 0 | |
| 509 | 4,7-dichlorobenzothiophene-2-yl | H | O-phenyl (2-OMe, 4-Br... 2-Br, OMe) | 35 | 69 | | 0 | 0 | 0 | 0 | |
| 510 | 4,7-dichlorobenzothiophene-2-yl | H | O-phenyl (2-CF₃, 4-F... with F) | 75 | 140 | | 8 | 0 | 0 | 0 | |
| 511 | 4,7-dichlorobenzothiophene-2-yl | H | O-phenyl (2-CH₃, 4-Br) | 45 | 94 | | 4 | 0 | 0 | 0 | |
| 512 | 4,7-dichlorobenzothiophene-2-yl | H | O-pyridyl (CF₃, Cl) | 9 | 170 | | 4 | 2 | 0 | 0 | |

TABLE 4-continued
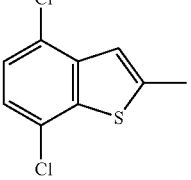
| Cmpd # | R₁ | R | X⁻ | IC₅₀ (μM) "C" | IC₅₀ (μM) TEM1 "A" | IC₅₀ (μM) L-1 "B" | Synergy at 10 μg/ml | | | | LogP or pKa |
|---|---|---|---|---|---|---|---|---|---|---|---|
| | | | | | | | Ent. Cl. | Ent. Faec. | Stap. Aureus | P99 Ent. Bact. | |
| 513 | 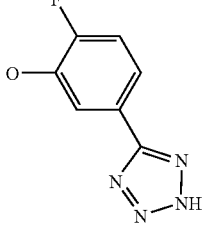 | H | 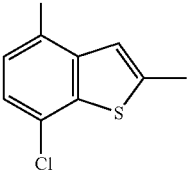 | 19 | >250 | | 4 | 0 | 0 | 0 | |
| 514 | 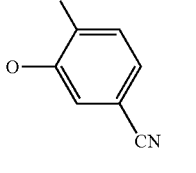 | H | 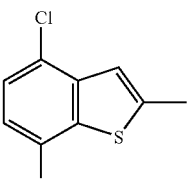 | 2 | 259 | | 16 | 0 | 0 | 2 | |
| 515 |  | H | 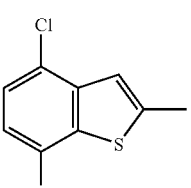 | 8 | 66 | | 4 | 2 | 2 | 0 | |
| 516 | 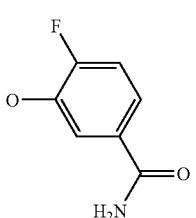 | H | 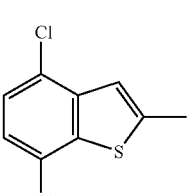 | 46 | 628 | | 16 | 0 | 0 | 0 | |
| 517 | 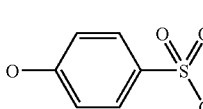 | H | 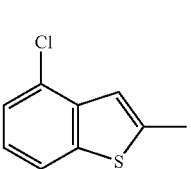 | 9 | 117 | | 8 | 0 | 2 | 0 | |
| 518 | 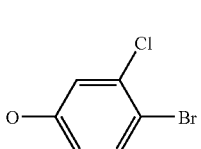 | H | | 5 10 | 227 94 | | 4 | 0 | 0 | 0 | |

TABLE 4-continued $$R^1-SO_2-NH-C(R)(H)-P(=O)(X)(O^-)$$

| Cmpd # | R₁ | R | X⁻ | IC₅₀ (µM) "C" | IC₅₀ (µM) TEM1 "A" | IC₅₀ (µM) L-1 "B" | Ent. Cl. | Ent. Faec. | Stap. Aureus | P99 Ent. Bact. | LogP or pKa |
|---|---|---|---|---|---|---|---|---|---|---|---|
| 519 | 4,7-diCl-2-methylbenzothiophene | H | 4-O-2-Br-nitrophenyl (O-phenyl with Br and NO₂) | 2; 1(MD) | 174; 98-MD | | 2 | 4 | 4 | 4 | 4(oxy) |
| 520 | 4,7-diCl-2-methylbenzothiophene | H | O-CH(CF₃)-(3-OMe-4-F-phenyl) | >500 | — | | 4 | 0 | 0 | 0 | |
| 521 | 4,7-diCl-2-methylbenzothiophene | H | O-(5-(CF₂·CF₃)pyridin-3-yl) | 12; 20-MD | 407; ≧664 | | 8 | 2 | 2 | 0 | |
| 522 | 4,7-diCl-2-methylbenzothiophene | H | O-(4-SO₂CF₃-phenyl) | 4; 8-MD; 1 | 184; ≧57; 26; 34 | | 8 | 2 | 8 | — | 2(oxy) |
| 523 | 4,7-diCl-2-methylbenzothiophene | H | O-(2-Br-5-(C(=O)NH-(3-Cl-5-Me-phenyl))phenyl) | 4; 12-MD | 62; 81 | | 4 | 2 | 4 | — | |
| 524 | 4,7-diCl-2-methylbenzothiophene | H | O-(2-Br-5-(C(=O)OMe)phenyl) | 14 | 175 | | 2 | 0 | 0 | — | |

TABLE 4-continued
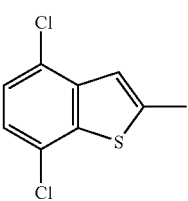
| Cmpd # | R₁ | R | X⁻ | IC₅₀ (μM) "C" | IC₅₀ (μM) TEM1 "A" | IC₅₀ (μM) L-1 "B" | Ent. Cl. | Ent. Faec. | Stap. Aureus | P99 Ent. Bact. | LogP or pKa |
|---|---|---|---|---|---|---|---|---|---|---|---|
| 525 | 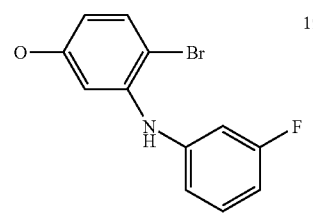 | H | 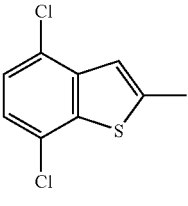 | 19 6 | 172 | | 0 | 2 | 0 | — | |
| 526 | 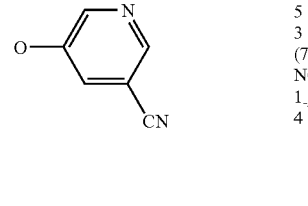 | H | 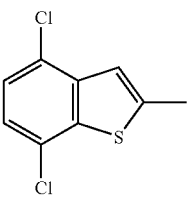 | 5 3 (75 μM NC) 1-MD 4 | 1K ≧3K 1K | | 8 | 4 | 8 | — | — |
| 527 | 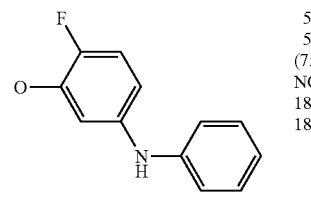 | H | 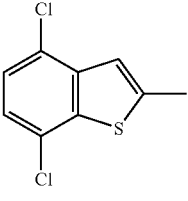 | 55 50 (75 uM NC) 183 181 | 60 | | 4 | 2 | 0 | — | |
| 528 | 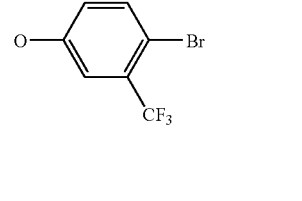 | H | 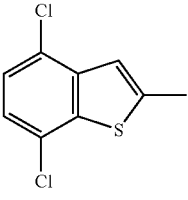 | 5 | 162 234 | | 8 | 2 | 0 | — | |
| 529 | 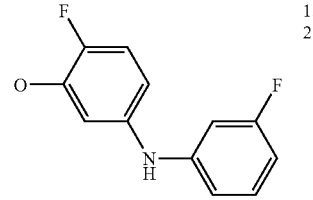 | H | 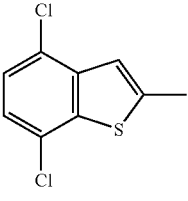 | 15 21 | 128 | | 4 | 2 | 2 | 0 | |
| 530 | 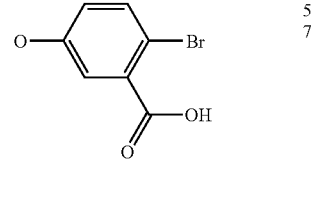 | H | | 56 76 | >250 | | 4 | 2 | — | 0 | |

TABLE 4-continued

| Cmpd # | R₁ | R | X⁻ | IC₅₀ (μM) "C" | IC₅₀ (μM) TEM1 "A" | IC₅₀ (μM) L-1 "B" | Synergy at 10 μg/ml | | | | LogP or pKa |
|---|---|---|---|---|---|---|---|---|---|---|---|
| | | | | | | | Ent. Cl. | Ent. Faec. | Stap. Aureus | P99 Ent. Bact. | |
| 531 | 4,7-diCl-2-Me-benzothiophene | H | 2-Br-5-O-phenyl-N-(2,4-difluorophenyl)carboxamide | 12 | 289 | | 4 | 0 | 0 | 0 | 2oxy |
| 532 | 4,7-diCl-2-Me-benzothiophene | H | 5-bromo-pyridin-3-yloxy | 19 xx-MD | 743 ≧752 | | 64 | 8 | 2 | 2 | |
| 533 | 4,7-diCl-2-Me-benzothiophene | H | 2-Br-5-O-phenyl-N-(2,6-difluorophenyl)carboxamide | 7 | 226 | | 4 | 4 | 8 | 0 | |
| 534 | 4,7-diCl-2-Me-benzothiophene | H | 6-methyl-pyridin-3-yloxy | 7 | 260 557 | | 16 | 2 | 2 | 0 | Insol. stock |
| 535 | 4,7-diCl-2-Me-benzothiophene | H | 3-F-4-O-phenyl-CH(OH)CF₃ | 28 | 123 | | 4 | 4 | 0 | 0 | |
| 536 | 4,7-diCl-2-Me-benzothiophene | H | 6-fluoro-pyridin-3-yloxy | 4 | 327 | | 4 | 4 | 2 | 2 | |

TABLE 4-continued
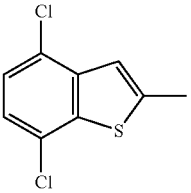
| Cmpd # | R₁ | R | X⁻ | IC₅₀ (μM) "C" | IC₅₀ (μM) TEM1 "A" | IC₅₀ (μM) L-1 "B" | Synergy at 10 μg/ml | | | | LogP or pKa |
|---|---|---|---|---|---|---|---|---|---|---|---|
| | | | | | | | Ent. Cl. | Ent. Faec. | Stap. Aureus | P99 Ent. Bact. | |
| 537 | 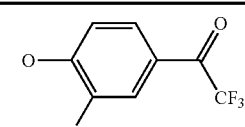 | H | 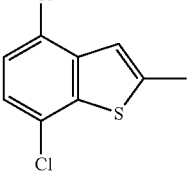 | 22 | 150 | | 0 | 4 | 0 | 0 | |
| 538 | 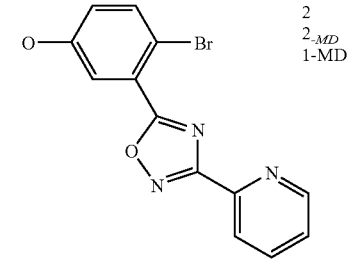 | H | 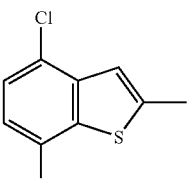 | 2<br>2-MD<br>1-MD | 272<br>≧247<br>>333 | | 64 | 4 | 4 | 0 | |
| 539 | 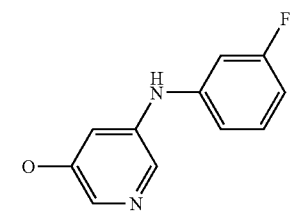 | H | 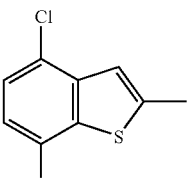 | 69 | 272 | | 4 | 4 | 0 | 0 | |
| 540 | 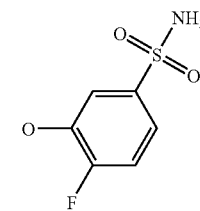 | H | 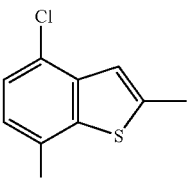 | 20 | >250 | | 16 | 4 | 4 | 0 | |
| 541 | 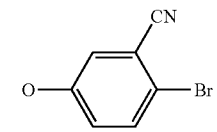 | H | 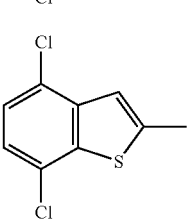 | 1 | 230 | | 16 | 4 | 4 | 0 | |
| 542 | 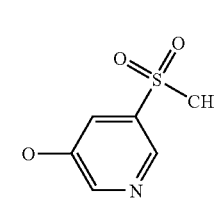 | H | | 11<br>4 | 37<br>57 | | 0 | 4 | — | 0 | |

TABLE 4-continued

| Cmpd # | R₁ | R | X⁻ | IC₅₀ (μM) "C" | IC₅₀ (μM) TEM1 "A" | IC₅₀ (μM) L-1 "B" | Synergy at 10 μg/ml | | | | LogP or pKa |
|---|---|---|---|---|---|---|---|---|---|---|---|
| | | | | | | | Ent. Cl. | Ent. Faec. | Stap. Aureus | P99 Ent. Bact. | |
| 543 | 4,7-dichlorobenzothiophen-2-yl | H | 4-(4-fluorobenzoyl)-3-(trifluoromethyl)phenoxy | >250 | >250 | | | | | | |
| 544 | 4,7-dichlorobenzothiophen-2-yl | H | 5-(phenylamino)pyridin-3-yloxy | | | | 4 | 0 | 8 | 0 | |
| 545 | 4,7-dichlorobenzothiophen-2-yl | H | phenoxy | | | | | | | | |
| 546 | 4,7-dichlorobenzothiophen-2-yl | H | 2-bromo-5-(cyclopropylcarbamoyl)phenoxy | 132 125 | 142 215 | | 2 | 0 | 2 | 0 | |
| 547 | 4,7-dichlorobenzothiophen-2-yl | H | 2-bromo-5-(pyridin-3-ylcarbamoyl)phenoxy | 12 8 | 115 229 | | 16 | 0 | 0 | 0 | |

TABLE 4-continued

| Cmpd # | R₁ | R | X⁻ | IC$_{50}$ (μM) "C" | IC$_{50}$ (μM) TEM1 "A" | IC$_{50}$ (μM) L-1 "B" | Ent. Cl. | Ent. Faec. | Stap. Aureus | P99 Ent. Bact. | LogP or pKa |
|---|---|---|---|---|---|---|---|---|---|---|---|
| 548 | 4,7-dichloro-2-methylbenzothiophene | H | 5-O-, 2-Br benzamide N-ethyl | 11 10 | 112 185 | | 4 | 0 | 0 | 0 | |
| 549 | 4,7-dichloro-2-methylbenzothiophene | H | 4-F, 3-O- benzyl NHCOCF₃ | 60 34 | 198 148 | | | | | | |
| 550 | 4,7-dichloro-2-methylbenzothiophene | H | 5-O-, 2-Br benzamide N-CH₂-thiophene | | | | 2 | 0 | 0 | 0 | |
| 551 | 4,7-dichloro-2-methylbenzothiophene | H | 4-F, 3-O- benzyl NH₂ | | | | 2 | 0 | 0 | 0 | |
| 552 | 4,7-dichloro-2-methylbenzothiophene | H | 5-O-, 2-Br benzamide N-(4-CF₃-phenyl) | 22$_{-MD}$ | 50 | | 2 | 0 | >16 | 0 | |

TABLE 4-continued

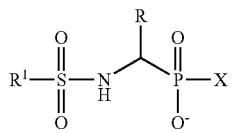

| Cmpd # | R₁ | R | X⁻ | IC$_{50}$ (μM) "C" | IC$_{50}$ (μM) TEM1 "A" | IC$_{50}$ (μM) L-1 "B" | Ent. Cl. | Ent. Faec. | Stap. Aureus | P99 Ent. Bact. | LogP or pKa |
|---|---|---|---|---|---|---|---|---|---|---|---|
| 553 | 4,7-dichloro-2-methylbenzothiophene | H | 2-bromo-5-O-,N-(2-trifluoromethoxyphenyl)benzamide | | | | 2 | 0 | 0 | 0 | |
| 554 | 4,7-dichloro-2-methylbenzothiophene | H | 2-bromo-5-O-,(4-fluorophenyl)ketone benzene | | | | 2 | 0 | 2 | 0 | |
| 555 | 4,7-dichloro-2-methylbenzothiophene | H | 2-bromo-5-O-,N-(3,4-difluorophenyl)benzamide | | | | 8 | 0 | 0 | 0 | |
| 556 | 4,7-dichloro-2-methylbenzothiophene | H | 4-O-phenyl-SO₂CF₂CF | 5$_{MD}$ | 32 | | >16 | 0 | >16 | 0 | |

TABLE 4-continued

| Cmpd # | R₁ | R | X⁻ | IC₅₀ (μM) "C" | IC₅₀ (μM) TEM1 "A" | IC₅₀ (μM) L-1 "B" | Ent. Cl. | Ent. Faec. | Stap. Aureus | P99 Ent. Bact. | LogP or pKa |
|---|---|---|---|---|---|---|---|---|---|---|---|
| 557 | 4,7-dichloro-2-methylbenzothiophene | H | 5-O-, 2-Br-benzamide-N-(2-trifluoromethylphenyl) | | | | | 0 | 0 | | |
| 558 | 4,7-dichloro-2-methylbenzothiophene | H | 5-O-, 2-Br-benzamide-N-(2,4,6-trifluorophenyl) | | | | | 0 | 0 | | |
| 559 | 4,7-dichloro-2-methylbenzothiophene | H | 5-O-, 2-Br-benzamide-N-(3-CF₃, 4-NO₂-phenyl) | 6₋MD | 65 | | | 0 | >16 | | |
| 560 | 4,7-dichloro-2-methylbenzothiophene | H | 5-O-, 2-Br-phenyl-1,3,4-oxadiazole-(2-nitrophenyl) | | | | | | | | |
| 561 | 4,7-dichloro-2-methylbenzothiophene | H | 4-O-, 3-methyl-6-NO₂-phenyl | 61 | 98 | | | | | | |

TABLE 4-continued

[Structure: R¹−S(O)₂−NH−CH(R)−P(=O)(X)(O⁻)]

| Cmpd # | R₁ | R | X⁻ | IC₅₀ (μM) "C" | IC₅₀ (μM) TEM1 "A" | IC₅₀ (μM) L-1 "B" | Synergy at 10 μg/ml Ent. Cl. | Ent. Faec. | Stap. Aureus | P99 Ent. Bact. | LogP or pKa |
|---|---|---|---|---|---|---|---|---|---|---|---|
| 562 | 2-thienyl | —CO₂Et | O-C₆H₄-NO₂ (4-nitrophenoxy) | >250 | >250 | | | | | | |
| 563 | 2-thienyl | —CO₂Et | O-C₆H₅ (phenoxy) | >250 | >250 | | | | | | |

TABLE 5

[Structure: R¹−C(=O)−NH−CH₂−P(=O)(X)(O⁻)]

| CMPD # | R¹ | X⁻ | IC₅₀ (μM) "C" | Synergy (at μg/mL) Class C E. Cl 10/1 | Ps. 100 | Class A H. In. 10/1 | St.A 10 |
|---|---|---|---|---|---|---|---|
| 221 | benzyl-CH₂—O— | F | 151 | 8/8 | | 0/0 | |
| 221A.2 | benzyl-CH₂—O— | F | 154 | 32/4 16/8 32/4 | 2 | 0 0 0 | 0 0 |
| 223 | benzyl-CH₂— | O-C₆H₄-NO₂ (3-nitrophenoxy) | | 4/2 | | | |
| 245 | phenyl-CH₂ | PNP | 19 | | | | |
| 253 | benzyl-CH₂— | O-C₆H₄-CO₂— (4-carboxyphenoxy) | | 2/0 | | 0 | |
| 255 | benzyl-CH₂— | O-C₆H₄-CO₂— (3-carboxyphenoxy) | | 4/2 | | | |

TABLE 5-continued
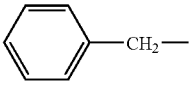
| CMPD # | R¹ | X⁻ | IC₅₀ (μM) "C" | Synergy (at μg/mL) | | | |
|---|---|---|---|---|---|---|---|
| | | | | Class C | | Class A | |
| | | | | E. Cl 10/1 | Ps. 100 | H. In. 10/1 | St.A 10 |
| 276 | 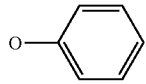 | 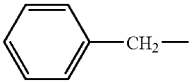 | | 2/0 | | | |
| 280 | 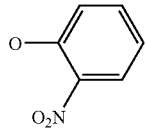 | 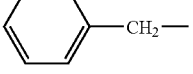 | | 2/2 | | 0 | 0 |
| 298 | 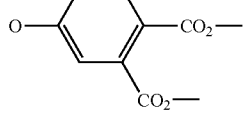 | 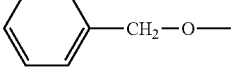 | | 0/0 | | 0/0 | |
| 701 | 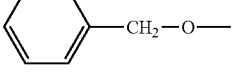 | PNP | 1 | 8/2 | | (2) | (2) |
| 702 | 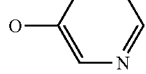 | 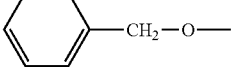 | >100 | 4/2 | | (4) | (0) |
| 703 | 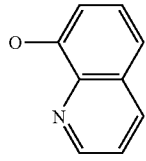 | 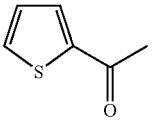 | >100 | 2/2 | | (8) | (4) |
| 704 | 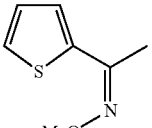 | PNP | | 0/0 | | 0 | 0 |
| 705 | 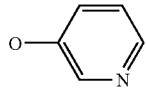 | 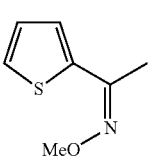 | 255 | 2/2 | | (2) | (0) |
| 706 | 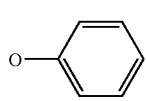 | 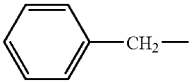 | >3K | 0/0 | | (0) | (0) |

TABLE 5-continued

R¹−C(O)−NH−CH₂−P(O)(O⁻)−X

| CMPD # | R¹ | X⁻ | IC₅₀ (μM) "C" | Synergy (at μg/mL) | | | |
|---|---|---|---|---|---|---|---|
| | | | | Class C | | Class A | |
| | | | | E. Cl 10/1 | Ps. 100 | H. In. 10/1 | St.A 10 |
| 707 | 2-thienyl-C(=N-OMe)-CH₃ | 2-fluorophenoxy | >1K | 2/0 | | (0) | (0) |
| 708 | 2-thienyl-C(=N-OMe)-CH₃ | PNP | 32 | 0/0 | | 2 | 0 |
| 709 | PhCH₂-O- | 4-fluorophenylthio | 41 | 2/0 | | 0 | 0 |
| 710 | PhCH₂-O- | 4-(1-imidazolyl)phenoxy | 172 | 2/0 | | 0 | 0 |
| 711 | 2-thienyl-CH₃ | PNP | 207 | 0/0 | | 0 | 0 |
| 712 | 2-thienyl-C(=N-OMe)-CH₃ | pentafluorophenoxy | >1K | 2/0 | | 0 | 0 |
| 713 | PhCH₂-O- | 2-chloro-3-pyridyloxy | 9 | 8/2 | | 0 | 2 |
| 714 | 2-thienyl-CH₃ | pentafluorophenoxy | | 0/0 | | 0 | 0 |
| 715 | 2-thienyl-C(=N-OMe)-CH₃ | 2,4,6-trifluorophenoxy | 2.2K | 2/2 | | 0 | 0 |

TABLE 5-continued

[structure: R¹—C(O)—NH—CH₂—P(=O)(O⁻)—X]

| CMPD # | R¹ | X⁻ | IC₅₀ (μM) "C" | Synergy (at μg/mL) Class C E. Cl 10/1 | Class C Ps. 100 | Class A H. In. 10/1 | Class A St.A 10 |
|---|---|---|---|---|---|---|---|
| 716 | benzyl-CH₂—O— | 2,4,6-trifluorophenoxy | 316 | 8/0 | | 0 | 0 |
| 717 | 2-thienyl-C(O)— | 2-chloropyridin-3-yloxy | | 8/0 | | 0 | 0 |
| 718 | 2-thienyl-C(=N-OMe)— | OH | 1.6K | 4/0 | | 0 | 0 |

We claim:

1. A compound of the following formula:

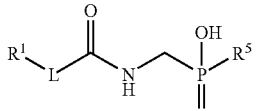

or a pharmaceutically acceptable salt thereof, wherein
R¹ is optionally substituted phenyl;
L is a covalent bond, —CH₂O—, —C(O)—, or —C(=N—OCH₃)—; and
R⁵ is -halo or —OR¹⁰ wherein R¹⁰ is phenyl, pyridinyl, or quinolinyl, each optionally substituted,
provided that when L is —CH₂O—, R⁵ is not —F or p-nitrophenyl.

2. The compound according to claim 1 wherein the substituents of the optionally substituted phenyl of R¹ and the optionally substituted phenyl, pyridinyl, and quinolinyl of R¹⁰ are independently selected from —NO₂, —CO₂H, and halo.

3. The compound according to claim 1 wherein R¹ is unsubstituted.

4. The compound according to claim 1 wherein R⁵ is selected from:

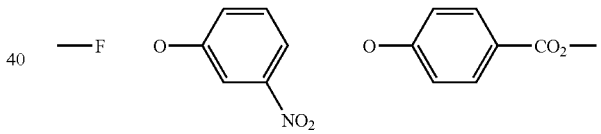

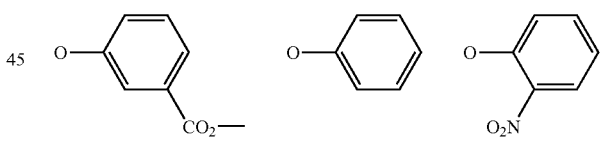

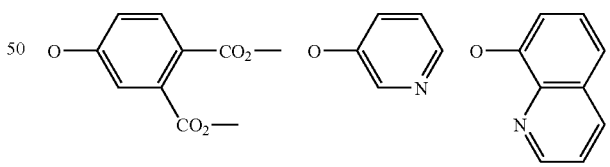

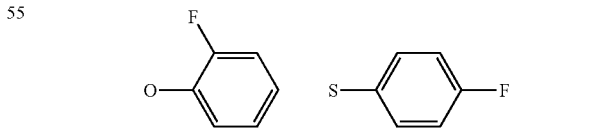

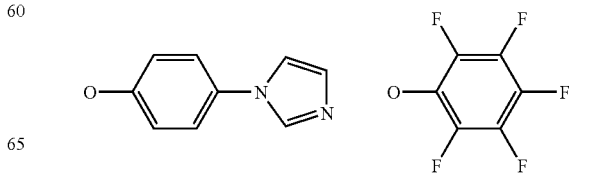

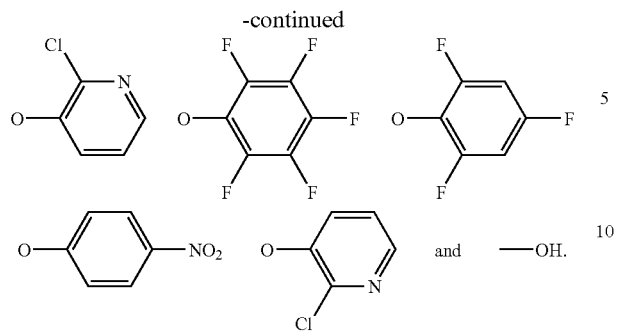

5. The compound according to claim 1 wherein R¹—L and R⁵ are selected from the following combinations:

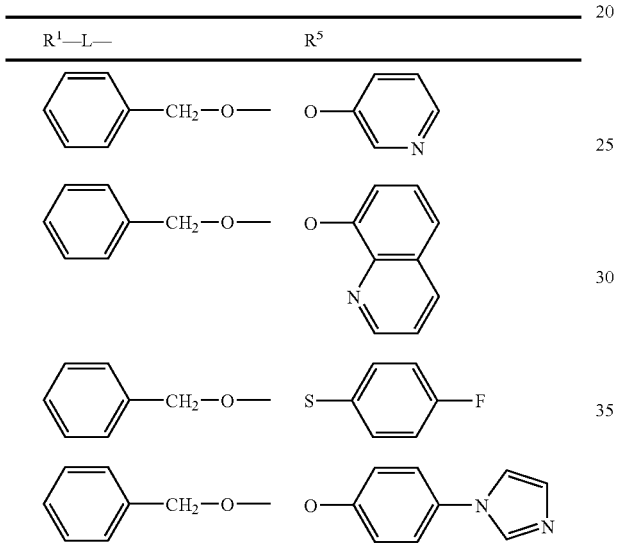

6. A compound of the following formula:

$$R^1-L-\overset{O}{\underset{}{C}}-N(H)-CH_2-\overset{OH}{\underset{O}{P}}-R^5$$

or a pharmaceutically acceptable salt thereof, wherein
  R¹ is optionally substituted phenyl;
  L is a covalent bond, —CH₂O—, —C(O)—, or —C(=N—OCH₃)—; and
  R⁵ is -halo or —OR¹⁰ wherein R¹⁰ is —H, phenyl, pyridinyl, or quinolinyl, each optionally substituted,
  provided that when L is —CH₂O—, R⁵ is not —F or p-nitrophenyl, and when R¹—L— s benzyloxy, R⁵ is not PNP.

* * * * *

UNITED STATES PATENT AND TRADEMARK OFFICE
CERTIFICATE OF CORRECTION

PATENT NO. : 7,514,556 B2
APPLICATION NO. : 11/830305
DATED : April 7, 2009
INVENTOR(S) : Besterman et al.

It is certified that error appears in the above-identified patent and that said Letters Patent is hereby corrected as shown below:

Please delete the structure " 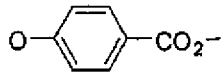 " at Column 166, line 40, and replace it with 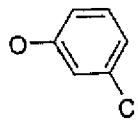

Please delete the structure " 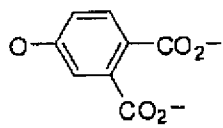 " at Column 166, line 45, and replace it with 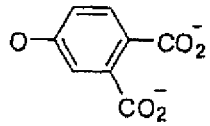

Please delete the structure " 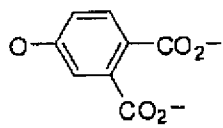 " at Column 166, line 50, and replace it with 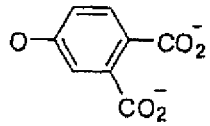

UNITED STATES PATENT AND TRADEMARK OFFICE
CERTIFICATE OF CORRECTION

PATENT NO. : 7,514,556 B2
APPLICATION NO. : 11/830305
DATED : April 7, 2009
INVENTOR(S) : Besterman et al.

It is certified that error appears in the above-identified patent and that said Letters Patent is hereby corrected as shown below:

Please delete the structure " 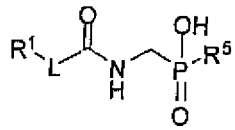 " at Column 168, line 25, and replace it with 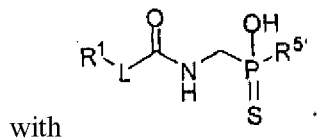 .

Signed and Sealed this

Twentieth Day of October, 2009

David J. Kappos
*Director of the United States Patent and Trademark Office*